US012201723B2

(12) United States Patent
Komori et al.

(10) Patent No.: US 12,201,723 B2
(45) Date of Patent: *Jan. 21, 2025

(54) COMBINED PHARMACEUTICAL FORMULATION COMPRISING GEMCITABINE-CONTAINING LIPOSOME COMPOSITION AND IMMUNE CHECKPOINT INHIBITOR

(71) Applicant: FUJIFILM Corporation, Tokyo (JP)

(72) Inventors: Takashi Komori, Ashigarakami-gun (JP); Tadaaki Ioroi, Ashigarakami-gun (JP); Takeshi Matsumoto, Ashigarakami-gun (JP); Yasuyuki Izumi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/125,291

(22) Filed: Dec. 17, 2020

(65) Prior Publication Data

US 2021/0106528 A1    Apr. 15, 2021

Related U.S. Application Data

(63) Continuation of application No. PCT/JP2019/024499, filed on Jun. 20, 2019.

(30) Foreign Application Priority Data

| Jun. 20, 2018 | (JP) | ................................. | 2018-116706 |
| Nov. 9, 2018 | (JP) | ................................. | 2018-211290 |
| May 15, 2019 | (JP) | ................................. | 2019-092245 |

(51) Int. Cl.
    *A61K 9/127*    (2006.01)
    *A61K 31/7068*  (2006.01)
    (Continued)

(52) U.S. Cl.
    CPC .......... *A61K 9/127* (2013.01); *A61K 31/7068* (2013.01); *A61P 35/00* (2018.01); *A61K 45/06* (2013.01)

(58) Field of Classification Search
    CPC .......... A61K 2300/00; A61K 2039/505; A61K 39/395; A61K 39/0011; A61K 39/39558;
    (Continued)

(56) References Cited

U.S. PATENT DOCUMENTS

| 4,970,074 A | 11/1990 | Flechtner et al. |
| 5,049,392 A | 9/1991 | Weiner et al. |

(Continued)

FOREIGN PATENT DOCUMENTS

| CN | 1960732 A | 5/2007 |
| CN | 101002733 A | 7/2007 |

(Continued)

OTHER PUBLICATIONS

Office Action issued Mar. 8, 2022 in Japanese Application No. 2020-525794.

(Continued)

*Primary Examiner* — Gollamudi S Kishore
(74) *Attorney, Agent, or Firm* — Sughrue Mion, PLLC

(57) ABSTRACT

An object of the present invention is to provide a combined pharmaceutical formulation obtained by combining a liposome composition and an immune checkpoint inhibitor, in which gemcitabine is encapsulated in a dissolved state in liposomes in the liposome composition. According to the present invention, there is provided a pharmaceutical formulation including (A) a liposome composition in combination with (B) an immune checkpoint inhibitor, in which the liposome composition includes liposomes each having an inner water phase, and an aqueous solution constituting an outer water phase and having the liposomes dispersed (Continued)

therein, gemcitabine is encapsulated in a dissolved state in the liposomes, and the liposome composition and the immune checkpoint inhibitor are administered simultaneously or sequentially.

6 Claims, 35 Drawing Sheets

(51) Int. Cl.
  *A61P 35/00* (2006.01)
  *A61K 45/06* (2006.01)

(58) Field of Classification Search
  CPC ... A61K 2039/6018; A61P 35/00; A61P 35/04
  USPC .......................................................... 424/450
  See application file for complete search history.

(56) References Cited

U.S. PATENT DOCUMENTS

| | | | |
|---|---|---|---|
| 5,077,056 A | 12/1991 | Bally et al. | |
| 5,094,854 A | 3/1992 | Ogawa et al. | |
| 5,227,170 A | 7/1993 | Sullivan | |
| 5,328,678 A | 7/1994 | Fujii et al. | |
| 5,393,530 A | 2/1995 | Schneider et al. | |
| 5,540,935 A | 7/1996 | Miyazaki et al. | |
| 5,567,433 A | 10/1996 | Collins | |
| 6,132,789 A | 10/2000 | Sprott et al. | |
| 6,261,597 B1 | 7/2001 | Kurtz | |
| 8,231,895 B2 | 7/2012 | de Almeida Moreira et al. | |
| 9,370,489 B2 | 6/2016 | Yang et al. | |
| 10,391,057 B2 | 8/2019 | Ono et al. | |
| 10,646,442 B2 | 5/2020 | Matsumoto et al. | |
| 10,898,435 B2 | 1/2021 | Ono et al. | |
| 11,166,913 B2 | 11/2021 | Kitahashi et al. | |
| 11,166,914 B2 | 11/2021 | Kitahashi et al. | |
| 2005/0169980 A1 | 8/2005 | Allen et al. | |
| 2005/0249795 A1 | 11/2005 | Zhang et al. | |
| 2005/0272688 A1 | 12/2005 | Higgins et al. | |
| 2007/0116753 A1 | 5/2007 | Hong et al. | |
| 2007/0166368 A1 | 7/2007 | Singh | |
| 2007/0178147 A1 | 8/2007 | Desai et al. | |
| 2008/0213183 A1 | 9/2008 | Bally et al. | |
| 2009/0217401 A1 | 8/2009 | Korman et al. | |
| 2010/0021531 A1 | 1/2010 | Yoshino et al. | |
| 2010/0239652 A1 | 9/2010 | Rochlitz et al. | |
| 2010/0292454 A1 | 11/2010 | Mishina et al. | |
| 2011/0002977 A1 | 1/2011 | Li et al. | |
| 2011/0064796 A1 | 3/2011 | Cipolla et al. | |
| 2011/0281815 A1 | 11/2011 | Ahrabi et al. | |
| 2012/0171283 A1 | 7/2012 | Hong et al. | |
| 2012/0282325 A1 | 11/2012 | Tong et al. | |
| 2013/0121912 A1 | 5/2013 | Yao et al. | |
| 2013/0122081 A1 | 5/2013 | Hong et al. | |
| 2013/0259922 A1 | 10/2013 | Haas et al. | |
| 2013/0302400 A1 | 11/2013 | Maneval et al. | |
| 2014/0154298 A1 | 6/2014 | Hong et al. | |
| 2015/0182460 A1 | 7/2015 | Hong et al. | |
| 2015/0209381 A1* | 7/2015 | Jimeno ................... A61P 35/02 514/47 | |
| 2016/0008283 A1 | 1/2016 | Nel et al. | |
| 2016/0030341 A1 | 2/2016 | Hong et al. | |
| 2016/0030342 A1 | 2/2016 | Hong et al. | |
| 2016/0051500 A1 | 2/2016 | Wanebo et al. | |
| 2016/0081928 A1 | 3/2016 | Hong et al. | |
| 2016/0095817 A1 | 4/2016 | Hong et al. | |
| 2016/0095852 A1 | 4/2016 | Hong et al. | |
| 2016/0106672 A1 | 4/2016 | Hong et al. | |
| 2016/0310453 A1 | 10/2016 | Mathios et al. | |
| 2016/0338956 A1 | 11/2016 | Hong et al. | |
| 2016/0339014 A1 | 11/2016 | Hong et al. | |
| 2017/0042810 A1 | 2/2017 | Matsumoto et al. | |
| 2017/0042811 A1 | 2/2017 | Ono et al. | |
| 2017/0042812 A1 | 2/2017 | Ono et al. | |
| 2017/0042813 A1 | 2/2017 | Ono et al. | |
| 2017/0071858 A1 | 3/2017 | Hong et al. | |
| 2017/0079912 A1 | 3/2017 | Hong et al. | |
| 2017/0079913 A1 | 3/2017 | Hong et al. | |
| 2017/0079914 A1 | 3/2017 | Hong et al. | |
| 2017/0158776 A1* | 6/2017 | Feltquate ............... C07K 16/32 |
| 2017/0202774 A1 | 7/2017 | Ono et al. | |
| 2017/0340624 A1 | 11/2017 | Hong et al. | |
| 2018/0169014 A1 | 6/2018 | Hong et al. | |
| 2018/0235954 A1 | 8/2018 | Hong et al. | |
| 2018/0243214 A1 | 8/2018 | Kitahashi et al. | |
| 2018/0243215 A1 | 8/2018 | Sekiguchi et al. | |
| 2019/0015507 A1 | 1/2019 | Xu et al. | |
| 2019/0336447 A1 | 11/2019 | Ono et al. | |
| 2021/0275453 A1 | 9/2021 | Kitahashi et al. | |
| 2023/0285295 A1 | 9/2023 | Komori et al. | |

FOREIGN PATENT DOCUMENTS

| | | | |
|---|---|---|---|
| CN | 101444485 A | 6/2009 | |
| CN | 101822669 A | 9/2010 | |
| CN | 101926779 A | 12/2010 | |
| CN | 102716089 A | 10/2012 | |
| CN | 102740833 A | 10/2012 | |
| CN | 102784107 A | 11/2012 | |
| CN | 104411324 A | 3/2015 | |
| CN | 105012966 A | 11/2015 | |
| EP | 0 565 361 A1 | 10/1993 | |
| EP | 0 565 361 B1 | 7/1996 | |
| EP | 2 656 835 A1 | 10/2013 | |
| EP | 3138557 A1 | 3/2017 | |
| JP | 2-1404 A | 1/1990 | |
| JP | 6-9374 A | 1/1994 | |
| JP | 2006-522026 A | 9/2006 | |
| JP | 2006-340714 A | 12/2006 | |
| JP | 2007-536247 A | 12/2007 | |
| JP | 4971142 B2 | 7/2012 | |
| JP | 2013-22482 A | 2/2013 | |
| JP | 2013-508315 A | 3/2013 | |
| JP | 2013-512262 A | 4/2013 | |
| JP | 2013-126953 A | 6/2013 | |
| JP | 2013-526563 A | 6/2013 | |
| JP | 2015-514109 A | 5/2015 | |
| RU | 2494729 C2 | 10/2013 | |
| WO | 2004/087115 A2 | 10/2004 | |
| WO | 2004/087115 A3 | 10/2004 | |
| WO | 2005/000266 A1 | 1/2005 | |
| WO | 2005/021012 A1 | 3/2005 | |
| WO | 2005/107712 A1 | 11/2005 | |
| WO | 2006/121168 A1 | 11/2006 | |
| WO | 2007/005754 A2 | 1/2007 | |
| WO | 2010/095964 A1 | 8/2010 | |
| WO | 2011/047689 A2 | 4/2011 | |
| WO | 2011/047689 A3 | 4/2011 | |
| WO | 2011/144745 A2 | 11/2011 | |
| WO | 2011/144745 A3 | 11/2011 | |
| WO | 2012/055020 A1 | 5/2012 | |
| WO | 2013/087791 A1 | 6/2013 | |
| WO | 2013/151774 A1 | 10/2013 | |
| WO | 2014/092858 A1 | 6/2014 | |
| WO | 2014/110555 A1 | 7/2014 | |
| WO | 2015/061752 A1 | 4/2015 | |
| WO | 2015/166985 A1 | 11/2015 | |
| WO | 2015/166986 A1 | 11/2015 | |
| WO | 2015/166987 A1 | 11/2015 | |
| WO | 2015/166988 A1 | 11/2015 | |
| WO | WO-2017004092 A1 * | 1/2017 | ......... A61K 31/4406 |
| WO | 2017/078008 A1 | 5/2017 | |
| WO | 2017/078009 A1 | 5/2017 | |
| WO | 2017/192863 A1 | 11/2017 | |
| WO | 2018/071668 A1 | 4/2018 | |
| WO | 2018/106729 | 6/2018 | |
| WO | 2019/244978 A1 | 12/2019 | |

OTHER PUBLICATIONS

Lindau et al., "The immunosuppressive tumour network: myeloid-derived suppressor cells, regulatory T cells and natural killer T

(56) References Cited

OTHER PUBLICATIONS cells", Immunology, vol. 138, No. 2, pp. 105-115, 2012 (11 pages total).
Sica et al., "Macrophage plasticity and polarization: in vivo veritas", The Journal of Clinical Investigation, vol. 122, No. 3, pp. 787-795, Mar. 2012 (10 pages total).
Eriksson et al., "Gemcitabine reduces MDSCs, tregs and TGFβ-1 while restoring the teff/treg ratio in patients with pancreatic cancer", Journal of Translational Medicine, vol. 14, No. 282, 2016 (12 pages total).
Chikamatsu, "Characterization and clinical implications of myeloid-derived suppressor cells in head and neck cancer", Journal of Japan Society of Immunology & Allergology in Otolaryngology (JJIAO), vol. 30, No. 4 pp. 271-278, 2012 (8 pages total).
Wang et al., "In situ formed reactive oxygen species-responsive scaffold with gemcitabine and checkpoint inhibitor for combination therapy", Science Translational Medicine, vol. 10, Issue 429, eaan3682, 2018 (13 pages total).
Extended European Search Report dated Jan. 2, 2017, from the European Patent Office in European application No. 15786062.8 corresponding to U.S. Appl. No. 15/335,640.
Office Action dated Jun. 27, 2017, from the Japanese Patent Office in JP Application No. 2016-516405, corresponding to U.S. Appl. No. 15/335,640.
International Preliminary Report on Patentability with the translation of Written Opinion dated Nov. 10, 2016, issued by the International Bureau in Application No. PCT/JP2015/062982, corresponding to U.S. Appl. No. 15/335,640.
International Search Report for PCT/JP2015/062982 dated Jun. 9, 2015, corresponding to U.S. Appl. No. 15/335,640.
Written Opinion for PCT/JP2015/062982 dated Jun. 9, 2015, corresponding to U.S. Appl. No. 15/335,640.
Federico et al., "Gemcitabine-loaded liposomes: rationale, potentialities and future perspectives", International Journal of Nanomedicine, vol. 7, pp. 5423-5436, 2012 (14 pages total).
May et al., "Thermosensitive Liposomes for the Delivery of Gemcitabine and Oxaliplatin to Tumors", Mol. Pharmaceutics, vol. 10, pp. 4499-4508, 2013 (10 pages total).
Zhou et al., "Preparation and characterization of gemcitabine liposome injections", Pharmazie, vol. 67, pp. 844-847, 2012 (4 pages total).
Gravem, "Gemcitabine-Containing Liposomes", Thesis for the degree Master of Pharmacy, May 2006 (86 pages total).
Paolino et al. "Gemcitabine-loaded PEGylated unilamellar liposomes vs GEMZAR®: Biodistribution, pharmacokinetic features and in vivo antitumor activity", Journal of Controlled Release, vol. 144, pp. 144-150, 2010 (7 pages total).
Bornmann et al., "A new liposomal formulation of Gemcitabine is active in an orthotopic mouse model of pancreatic cancer accessible to bioluminescence imaging", Cancer Chemother Pharmacol, vol. 61, pp. 395-405, 2008 (11 pages total).
Arpicco et al., "Hyaluronic acid-coated liposomes for active targeting of gemcitabine", European Journal of Pharmaceutics and Biopharmaceutics, vol. 85, pp. 373-380, 2013 (8 pages total).
Office Action dated Aug. 1, 2017, from the Japanese Patent Office in JP application No. 2016-516406, corresponding to U.S. Appl. No. 15/336,057.
Extended European Search Report Jan. 2, 2017 from the European Patent Office in Application No. 15785362.3, corresponding to U.S. Appl. No. 15/336,057.
International Preliminary Report on Patentability with the translation of Written Opinion dated Nov. 10, 2016, issued by the International Bureau in Application PCT/JP2015/062983, corresponding to U.S. Appl. No. 15/336,057.
International Search Report for PCT/JP2015/062983, Form PCT/ISA/210 mailed Jun. 9, 2015, corresponding to U.S. Appl. No. 15/336,057.
Written Opinion for PCT/JP2015/062983, Form PCT/ISA/237 mailed Jun. 9, 2015, corresponding to U.S. Appl. No. 15/336,057.

Office Action dated Apr. 19, 2017 in U.S. Appl. No. 15/335,640.
Office Action dated Sep. 1, 2017 in U.S. Appl. No. 15/335,640.
Office Action dated Jun. 29, 2018 in U.S. Appl. No. 15/335,640.
Office Action dated Feb. 8, 2019 in U.S. Appl. No. 15/335,640.
Office Action dated Jun. 5, 2019 in U.S. Appl. No. 15/335,640.
Office Action dated Oct. 22, 2019 in U.S. Appl. No. 15/335,640.
Notice of Allowance dated Jan. 31, 2020 in U.S. Appl. No. 15/335,640.
Office Action dated Apr. 14, 2017 in U.S. Appl. No. 15/336,057.
Office Action dated Sep. 1, 2017 in U.S. Appl. No. 15/336,057.
Office Action dated Jun. 29, 2018 in U.S. Appl. No. 15/336,057.
Office Action dated Feb. 11, 2019 in U.S. Appl. No. 15/336,057.
Notice of Allowance dated Apr. 19, 2019 in U.S. Appl. No. 15/336,057.
International Search Report dated Aug. 27, 2019 for PCT/JP2019/024499, corresponding to the present application.
Written Opinion dated Aug. 27, 2019 for PCT/JP2019/024499, corresponding to the present application.
International Preliminary Report on Patentability dated Dec. 22, 2020 from the International Bureau in International Application PCT/JP2019/024499, corresponding to the present application.
Extended European Search Report dated Jul. 1, 2021 in European Application No. 19821941.2.
U.S. Appl. No. 17/125,291, Pending.
U.S. Appl. No. 15/335,640, U.S. Pat. No. 10,646,442.
U.S. Appl. No. 15/336,057, U.S. Pat. No. 10,391,057.
Office Action dated Sep. 10, 2021, from the Australian Patent Office in AU Application No. 2019288048.
Office Action dated Nov. 9, 2021 from the Japanese Patent Office in JP Application No. 2020-525794.
Office Action issued Apr. 11, 2022 in Australian Application No. 2019288048.
Office Action dated Apr. 26, 2022 in Canadian Application No. 3,104,084.
Office Action issued Nov. 28, 2022 in U.S. Appl. No. 17/121,870.
Immordino et al., "Stealth liposomes: review of the basic science, rationale, and clinical applications, existing and potential", International Journal of Nanomedicine, 2006, vol. 1, No. 3, pp. 297-315 (19 pages total).
Anne-Laure Papa et al., "PEGylated liposomal Gemcitabine: insights into a potential breast cancer therapeutic", Cellular Oncology, vo. 36, No. 6, pp. 449-457, XP055511227, Oct. 1, 2013 (9 pages total).
Communication dated Jul. 26, 2019, from the European Patent Office in European Application No. 16862068.0.
Communication dated Jun. 24, 2020, from The State Intellectual Property Office of the P.R. of China in Chinese Application No. 201680064060.7.
Communication dated Mar. 2, 2020 from European Patent Office in EP Application No. 16 862 068.0.
Cosco, Donato et al., "Liposomes as multicompartmental carriers for multidrug delivery in anticancer chemotherapy", Drug Delivery and Translational Research, 2011, pp. 66-75, vol. 1 (10 pages total).
D. Cosco et al "In vivo activity of gemcitabine-loaded PEGylated small unilamellar liposomes against pancreatic cancer", Cancer Chemother Pharmacol., vol. 64, pp. 1009-1020, 2009.
D.D. Von Hoff et al., "Gemcitabine Plus nab-Paclitaxel Is an Active Regimen in Patients With Advanced Pancreatic Cancer: A Phase I/II Trial", Journal of Clinical Oncology, vol. 29, No. 34, Dec. 1, 2011, pp. 4548-4554.
"Efficiency of a combination of nab-paclitaxel with gemcitabine in the metastatic pancreatic cancer", Oncology News, http://rosoncoweb.ru/news/oncology/2013/02/05/, Feb. 5, 2013, (2 pages total).
English translation of CN 1012784107 A. Obtained from https://patents.google.com/patent/CN102784107A/enQoq=gemcitabine+liposome on Jun. 12, 2018. 7 printed pages. Originally published Nov. 12, 2012 (Year 2012).
English translation of CN 101444485 A. Google Translate. https://patent.google.com/patent/CN01444485/en?oq=gemcitabine+liposome accessed on Apr. 16, 2019, document originally published in Chinese on Jun. 3, 2008, 8 printed page. (Year: 2008).
English translation of CN 102716089 A. Obtained from https://oatents.google.com/patent/CN102716089A/en?oq=gemcitabine+liposome on Jun. 12, 2018. 12 printed pages. Originally published Oct. 10, 2012 (Year: 2012).

(56) References Cited

OTHER PUBLICATIONS

Extended European Search Report dated Oct. 15, 2018, issued by the European Patent Office in European application No. 16862068.0.
F. de Meyer et al., "Effect of cholesterol on the structure of a phospholipid bilayer, " Proceedings of the National Academy of Sciences, vol. 106, No. 10, 2009, pp. 3654-3658, published Mar. 10, 2009. (Year: 2009).
Final Office Action dated Dec. 22, 2020 issued in U.S. Appl. No. 15/967,970.
Final Office Action dated Mar. 13, 2020 in U.S. Appl. No. 15/967,970.
Frese et al., "nab-Paclitaxel Potentiates Gemcitabine Activity by Reducing Cytidine Deaminase Levels in a Mouse Model of Pancreatic Cancer", Cancer Discovery, 2012, vol. 2, No. 3, pp. 260-269 (11 pages total).
Hearing Notice dated Feb. 10, 2022 from the Intellectual Property Office of India in IN Application No. 202048043283.
Hideki Ueno et al., "Systemic chemotherapy for advanced pancreatic cancer", Journal of Clinical and Experimental Medicine, Feb. 21, 2015, pp. 887-892, vol. 252, No. 8 (6 pages total).
International Preliminary Report on Patentability dated May 8, 2018 issued by the International Bureau in PCT/JP2016/082415.
International Search Report of PCT/JP2016/082415 dated Dec. 27, 2016 [PCT/ISA/210].
Jing, Y., "Application Directory of Pharmaceutical Excipients", China Medical Science Press, Aug. 31, 2011, p. 264 (2 pages).
JN Israelachvili, S Marcelja, and RG Horn, "Physical principles of membrane organization," Quarterly Reviews of Biophysics, vol. 13 No. 2, 1980, pp. 121-200. (Year: 1980).
Kathy S. Albain et al., "Gemcitabine Plus Paclitaxel Versus Paclitaxel Monotherapy in Patients With Metastatic Breast Cancer and Prior Anthracycline Treatment", Journal of Clinical Oncology, Aug. 20, 2008, pp. 3950-3957, vol. 26, No. 24.
Kazuo Maruyama, "Passive targeting with liposomal drug carriers", Drug Delivery System, 1999, pp. 433-447, vol. 14, No. 6 (15 pages total).
Liboiron, Barry D. et al., "Nanoscale delivery systems for combination chemotherapy", Drug Delivery in Oncology, 2012, pp. 1013-1050, vol. 2 (38 pages total).
M. Celano et al., "Cytotoxic effects of Gemcitabine-loaded liposomes in human anaplastic thyroid carcinoma cells", in BMC Cancer, vol. 4, pp. 1-5, 2004.
N. A. Oborotova et al., "Thermosensitive Liposome Drug Forms in the Experimental Oncology", Russian Biotherapeutic Journal, vol. 5, No. 1, 2006, pp. Oncology, Rossiiskii terapeuticheskii zhurnal (Russian Biotherapeutic Journal), vol. 5, No. 1, 2006, pp. 62-70, 9 pages total.
N.B. Demina et al., Development Strategy and Biopharmaceutical Aspects of Drug Delivery Systems // Russian Chemistry Journal, 2012, vol. 56, N.3-4, pp. 5-10, p. 8 (6 pages).
Notice of Allowance issued Jul. 6, 2021 in U.S. Appl. No. 15/967,970.
Notice of Allowance issued Jul. 8, 2021 in U.S. Appl. No. 16/808,004.
Notification of Reasons for Refusal dated Feb. 12, 2019 from the Japanese Patent Office in Japanese Application No. 2017-548769.
Notification of the results of patentability assessment from the Federal Service for Intellectual Property of Russia dated Feb. 25, 2020 in No. 2018119680/04.
Office Action dated Aug. 20, 2020 issued in U.S. Appl. No. 15/967,970.
Office Action dated Apr. 19, 2022 from the China National Intellectual Property Administration in CN Application No. 202010466892.X.
Office Action dated Apr. 2, 2022 from the China National Intellectual Property Administration in CN Application No. 202010466486.3.
Office Action dated Aug. 18, 2022 from The State Intellectual Property Office of People's Republic of China in Application No. 202010466892.X.
Office Action dated Feb. 9, 2021, from the Indian Patent Office in Indian Application No. 202048043283.
Office Action dated Jul. 26, 2019 from the Indian Patent Office in Indian Application No. 201847016588.
Office Action dated Jun. 18, 2019, from the Japanese Patent Office in Japanese Application No. 2017-548769.
Office Action dated Mar. 2, 2021, from the Intellectual Property Office of India in Indian Application No. 202048043278.
Office Action dated Mar. 31, 2021 issued by the Russian Patent Office in Russian Application No. 2020137384/04.
Office Action dated Mar. 31, 2021 issued by the Russian Patent Office in Russian Application No. 2020137385/04.
Office Action dated May 21, 2019, from the Russian Federal Service for Intellectual Property in Russian Application No. 2018119680/04.
Office Action dated Nov. 13, 2019 from the State Intellectual Property Office of the P.R.C. in Chinese Application No. 201680064060.7.
Office Action dated Sep. 26, 2019, from the Russian Federal Service for Intellectual Property in Russian Application No. 2018119680/04.
Office Action dated Sep. 3, 2019, from the Korean Intellectual Property Office in Korean application No. 10-2018-7012568.
Office Action issued Aug. 26, 2021 in Russian Application No. 2020137385.
Office Action issued Sep. 3, 2021 in Chinese Application No. 202010466486.3.
P.K. Working et al., "Pharmacokinetics, Biodistribution and Therapeutic Efficacy of Doxorubicin Encapsulated in Stealth® Liposomes (Doxil®)", Journal of Liposome Research, 1994, pp. 667-687, vol. 4. No. 1 (21 pages total).
Pandet et al, "Industrial Pharmacy", Chinese Pharmaceutical Science Press, Jun. 30, 2010, pp. 477-478 (3 pages total).
Pharmaceutical Technology: Pharmaceutics, Textbook for University Students, I.I. Krosniuk, G.V. Mikhaylova, 2nd edition, stereotyped, Moscow, Academia Publishing Center, 2006, pp. 297-299 (4 pages).
Qinmei Zhou et al., "Analysis of gemcitabine liposome injection by HPLC with evaporative light scattering detection", Journal of Liposome Research, vo. 22, No. 4, Jan. 1, 2002, XP009508406 (7 pages total).
Soema et al., "Predicting the influence of liposomal lipid composition on liposome size, zeta potential and liposome-induced dendritic cell maturation using a design of experiments approach", European Journal of Pharmaceutics and Biopharmaceutics, 2015, vol. 94, pp. 427-435 (9 pages total).
ST. et al, "Pharmacy", Pekin University Medical Press, Jan. 31, 2005, p. 493 (2 pages total).
Trosko et al., "Mechanism of up-regulated gap junctional intercellular communication during chemoprevention and chemotherapy of cancer", Mutation Research, vol. 480-481, pp. 219-229 (2001).
Von Hoff, Daniel D. et al., "Increased Survival in Pancreatic Cancer with nab-Paclitaxel plus Gemcitabine", The New England Journal of Medicine, 2013, pp. 1691-1703, vol. 369, No. 18 (13 pages total).
William J. Gradishar et al., "Phase III Trial of Nanoparticle Albumin-Bound Paclitaxel Compared With Polyethylated Castor Oil-Based Paclitaxel in Women With Breast Cancer", Journal of Clinical Oncology, 2005, Nov. 1, 2005, pp. 7794-7803, vol. 23, No. 31 (10 pages total).
Written Opinion of PCT/JP2016/082415 dated Dec. 27, 2016 [PCT/ISA/237].
Extended European Search Report dated Jan. 2, 2017 from the European Patent Office in European Application No. 15785362.3.
International Search Report for PCT/JP2015/062983, Form PCT/ISA/210 mailed Jun. 9, 2015.
Written Opinion for PCT/JP2015/062983, Form PCT/ISA/237 mailed Jun. 9, 2015.
Office Action dated Aug. 1, 2017, from the Japanese Patent Office in Japanese application No. 2016-516406.
International Preliminary Report on Patentability dated Nov. 10, 2016, issued by the International Bureau in International Application PCT/JP2015/062983.
Daryl C. Drummond, "Pharmacokinetics and In Vivo Drug Release Rates in Liposomal Nanocarrier Development", Journal of Pharmaceutical Sciences, vol. 97, No. 11, Nov. 2008, pp. 4696-4740.

(56) References Cited

OTHER PUBLICATIONS

A phase I dose-escalation and immune biomarker study of intravenous FF-10832, liposomal gemcitabine, in patients with advanced solid tumors. published at https://ascopubs.org/doi/abs/10.1200/JCO.2019.37.15_suppl.TPS3163, May 26, 2019.
A Phase 1 Dose-Escalation and Immune Biomarker Study of Intravenous FF-10832, Liposomal Gemcitabine, in Patients with Advanced Solid Tumors ASCO 2019 : 55th Annual Meeting of the American Society of Clinical Oncology, Jun. 1, 2019.
International Search Report issued May 11, 2021 in International Application No. PCT/JP2021/014285.
Written Opinion of the International Searching Authority issued May 11, 2021 in International Application No. PCT/JP2021/014285.
Office Action issued Jun. 23, 2020 in U.S. Appl. No. 16/511,380.
Notice of Allowance issued Oct. 21, 2020 in U.S. Appl. No. 16/511,380.
Fujifilm Corporation News Release, https://www.fujifilm.co/jp/corporate/news/articleffnr_1366.html, Nov. 2, 2018 (2 pages total).
Eli Lilly Japan, K.K., "Gemzar Injection", 2019 (6 pages total).
"Clinical Practice Guidelines for Pancreatic Cancer", 2019 https://minds.jcqhc.or.jp/n/med/4/med0037/G0001105/0062 (2 pages total).
Borazanci et al., "A phase I dose-escalation and immune biomarker study of intravenous FF-10832, liposimal gemcitabine, in patients with advanced solid tumors", Journal of Clinical Oncology, May 26, 2019, vol. 37 (15_suppl) (3 pages total).
Office Action issued Jul. 15, 2022 in U.S. Appl. No. 17/121,870.
C. Federico et al, "Gemcitabine-loaded liposomes: rationale, potentialities and future perspectives", International Journal of Nanomedicine, vol. 7, pp. 5423-5436, 2012.
Office Action issued Jun. 12, 2020 in U.S. Appl. No. 16/808,004.
Office Action issued Oct. 8, 2020 in U.S. Appl. No. 16/808,004.
Office action issued Aug. 15, 2019 in U.S. Appl. No. 15/967,970.
Office action issued Jul. 12, 2018 in U.S. Appl. No. 15/967,970.
Office action issued Feb. 15, 2019 in U.S. Appl. No. 15/967,970.
Advisory Action issued Jan. 21, 2021 in U.S. Appl. No. 16/808,004.
Office Action issued Nov. 1, 2021 in Chinese Application No. 202010466892.X.
Extended European Search Report issued Jan. 2, 2017 in European Application No. 15786541.1.
International Search Report issued Jun. 9, 2015 in International Application No. PCT/JP2015/062984.
Written Opinion of the International Searching Authority issued Jun. 9, 2015 in International Application No. PCT/JP2015/062984.
International Preliminary Report on Patentability issued Nov. 1, 2016 in International Application No. PCT/JP2015/062984.
Office Action issued Jun. 27, 2017 in Japanese Application No. 2016-516407.
Hongtao Xu et al., "Development of High-Content Gemcitabine PEGylated Liposomes and Their Cytotoxicity on Drug-Resistant Pancreatic Tumour Cells", Pharm Res, 2014, vol. 31, pp. 2583-2592 (10 pages total).
Celia et al., "Improved In Vitro Anti-Tumoral Activity, Intracellular Uptake and Apoptotic Induction of Gemcitabine-Loaded Pegylated Unilamellar Liposomes", Journal of Nanoscience and Nanotechnology, 2008, vol. 8, pp. 2102-2113 (12 pages total).
Cortesi, "Preparation of liposomes by reverse-phase evaporation using alternative organic solvents", Journal of Microencapsulation, 1999, vol. 16, No. 2, pp. 251-256 (7 pages total).
Office Action issued May 13, 2020 in European Application No. 15786541.1.
Office Action issued Apr. 4, 2018 in U.S. Appl. No. 15/474,644.
Office Action issued Sep. 19, 2018 in U.S. Appl. No. 15/474,644.
Office Action issued Feb. 12, 2019 in U.S. Appl. No. 15/474,644.
Office Action issued Jun. 17, 2019 in U.S. Appl. No. 15/474,644.
Office Action issued Mar. 30, 2020 in U.S. Appl. No. 15/474,644.
Notice of Allowance issued May 14, 2020 in U.S. Appl. No. 15/474,644.
Office Action issued Apr. 7, 2017 in U.S. Appl. No. 15/336,158.

"Guidance for Industry: Estimating the Maximum Safe Stalting Dose in Initial Clinical Trials for Therapeutics in Adult Healthy volunteers", FDA (US), CDER, Jul. 1, 2005, pp. 1-27 (30 pages total)
Clinical Trials NCT03440450: "A Phase 1 Dose-escalation Study of FF-10832 for Treatment of Solid Tumors-Full Text View-Clinicals Trials.gov", ClinicalTrials.gov, Jan. 1, 2018, pp. 1-9.
Extended European Search Report dated May 8, 2023 issued by European Patent Office in EP application No. 21781882.2, corresponding to U.S. Appl. No. 17/937,126.
Higuchi, T., et al., "FF-10832 enables long survival via effective gemcitabine accumulation in a lethal murine peritoneal dissemination model", Cancer Science, vol. 110, No. 9, Sep. 1, 2019, pp. 2933-2940.
Qiang Tong et al., "Distribution of Magnetic Gemcitabine Stealth Nano-Liposomes in Vivo and Its Antitumor Effects on Human Breast Cancer Xenografts in Nude Mice" Chin Pharm J., Oct. 2009, vol. 44, No. 19, pp. 1487-1491 (5 pages total).
Office Action dated Feb. 18, 2023 issued in the Chinese patent application No. 201980041037.X.
Office Action dated Mar. 2, 2023 issued in the European patent application No. 19 821 941.2.
Office Action issued Jun. 6, 2023 in Japanese Application No. 2022-090689.
Mamta Parikh, et al., "Combination checkpoint immunotherapy and cytotoxic chemotherapy: Further results from phase Ib/II trial of pembrolizumab and docetaxel or gemcitabine in patients with advanced or metastatic urothelial cancer", Journal of Clinical Oncology, 2018, vol. 36, No. 6 p. 525 (5 pages).
Office Action issued Jun. 27, 2023 in Japanese Application No. 2021-063269.
History of Changes for Study: NCT03440450, ClinicalTrials.gov, 2019 (7 pages).
Notice of Allowance issued Feb. 10, 2023 in U.S. Appl. No. 17/121,870.
Office Action dated Mar. 9, 2023 in corresponding Taiwanese Application No. 108121529.
Abul Azad, et al., "PD-L1 blockade enhances response of pancreatic ductal adenocarcinoma to radiotherapy", EMBO Molecular Medicine, 2017, vol. 9, No. 2, pp. 167-180 (14 pages total).
W. Joost Lesterhuis, et al., "Synergistic Effect of CTLA-4 Blockade and Cancer Chemotherapy in the Induction of Anti-Tumor Immunity", PLOS One, Apr. 2013, vol. 8, Issue 4, e61895, pp. 1-8 (8 pages total).
Office Action issued Aug. 21, 2023 in U.S. Appl. No. 17/184,928.
Office Action issued Jul. 26, 2023 in Chinese Application No. 202180026552.8, U.S. Appl. No. 17/937,126.
Office Action issued Jul. 1, 2023 in corresponding Chinese Application No. 201980041037.X.
Office Action issued Aug. 15, 2023 in corresponding Taiwanese Application No. 108121529.
Office Action issued Sep. 18, 2023 in Australian Application No. 2021249949, corresponding to U.S. Appl. No. 17/937,126.
Office Action issued Oct. 10, 2023 in Japanese Application No. 2021-063269, corresponding to U.S. Appl. No. 17/937,126.
Office Action dated Sep. 28, 2023 in Chinese Application No. 201980041037.X.
U.S. Appl. No. 17/937,126, filed Sep. 30, 2022 (Matsumoto et al.).
Office Action dated Jan. 4, 2024 in Australian Application No. 2021249949.
Office Action issued Feb. 3, 2024 in Chinese Application No. 202180026552.8, corresponding to U.S. Appl. No. 17/937,126.
Cu Centit et al., "New Practical Drug Manual", Hionan Scientific Technical Press, 4th Edition, Aug. 2018, p. 1213 (2 pages total).
Korrupin et al., "Oncology Medication Manual", Foku Scientific Technical Press, 1st Edition, Aug. 2003, p. 150 (2 pages total).
Olivier Rixe, et al., "Phase I dose-escalation study of cabazitaxel administered in combination with gemcitabine in patients with metastatic or unresectable advanced solid malignancies", Anti-Cancer Drugs, 2015, vol. 26, No. 7, pp. 785-792 (8 pages total).

(56) References Cited

OTHER PUBLICATIONS

Office Action issued Feb. 9, 2024 in Canadian Application No. 3,173,715, corresponding to U.S. Appl. No. 17/937,126.

* cited by examiner

COMBINED PHARMACEUTICAL FORMULATION COMPRISING GEMCITABINE-CONTAINING LIPOSOME COMPOSITION AND IMMUNE CHECKPOINT INHIBITOR

CROSS-REFERENCE TO RELATED APPLICATIONS

This application is a Continuation of PCT International Application No. PCT/JP2019/024499 filed on Jun. 20, 2019, which claims priority under 35 U.S.C § 119(a) to Japanese Patent Application No. 2018-116706 filed on Jun. 20, 2018, Japanese Patent Application No. 2018-211290 filed on Nov. 9, 2018 and Japanese Patent Application No. 2019-092245 filed on May 15, 2019. Each of the above application(s) is hereby expressly incorporated by reference, in its entirety, into the present application.

BACKGROUND OF THE INVENTION

1. Field of the Invention

The present invention relates to a pharmaceutical formulation in which an immune checkpoint inhibitor and a gemcitabine-containing liposome composition are combined and administered simultaneously or sequentially.

2. Description of the Related Art

In recent years, it has become known that cancer utilizes a system that evades the immune surveillance. Cancer immunotherapy is a therapy that acts on the immune surveillance of cancer patients to strengthen the immunity against cancer, thereby suppressing the progression of cancer or treating cancer. Immune checkpoint molecules such as CTLA-4 and PD-1 or a ligand thereof, PD-L1 are known as molecules used in such an evasion system (WO2006/121168A and JP2006-340714A).

In addition, it is disclosed that co-administration of human anti-PD-1 or an antigen-binding moiety thereof with a chemotherapeutic agent is endowed with two anticancer agents that act by different mechanisms, which have cytotoxic effects on human tumor cells (WO2006/121168A and JP2006-340714A). However, WO2006/121168A and JP2006-340714A do not disclose an anticancer agent using a liposome in co-administration of human anti-PD-1 or an antigen-binding moiety thereof and a chemotherapeutic agent.

In addition, at the Opdivo Q&A site, in response to the question of whether Opdivo can be used in combination with chemotherapeutic agents, it has been disclosed that Opdivo cannot be used in combination because the efficacy and safety thereof in combination with cancer chemotherapeutic agents have not been established ("ONO ONCOLOGY Opdivo Q&A, Can Opdivo be used in combination with chemotherapeutic agents?", [online], publication date unknown, Ono Pharmaceutical Co., Ltd., [Search on May 2, 2018], Internet <URL: https://www.ono-oncology.jp/contents/patient/opdivo_faq/11.html>).

On the other hand, in chemotherapy, the attack on cancer cells is greatly affected by the exposure time of the drug. For example, a drug such as an antimetabolite which inhibits DNA synthesis attacks only a part of cells in the DNA synthesis phase, and therefore effective cell killing cannot be obtained in a case where the exposure time is short. In such a drug, in a case where in vivo metabolism thereof after administration is fast, sufficient exposure time at the tumor cannot be obtained and therefore an expected drug efficacy is often not obtained (WO2015/166985A and WO2015/166986A).

It is known that, by a configuration such that a drug is encapsulated in a dissolved state in an inner water phase of a liposome and a liposome composition is made hypertonic, release of the drug from the liposome composition can be promoted and therefore more suitable drug delivery can be realized (WO2015/166985A and WO2015/166986A).

SUMMARY OF THE INVENTION

An object according to an aspect of the present invention is to provide a combined pharmaceutical formulation obtained by combining an immune checkpoint inhibitor and an anticancer agent-containing liposome composition, and a method for administering the same. Another object according to the aspect of the present invention is to provide a combined pharmaceutical formulation obtained by combining an immune checkpoint inhibitor and an anticancer agent-containing liposome composition, and a therapeutic method using the same.

As a result of extensive studies, the present inventors have found that the foregoing objects can be achieved by a pharmaceutical formulation including (A) a liposome composition in combination with (B) an immune checkpoint inhibitor, in which the liposome composition includes liposomes each having an inner water phase, and an aqueous solution constituting an outer water phase and having the liposomes dispersed therein, gemcitabine is encapsulated in a dissolved state in the liposomes, and the liposome composition and the immune checkpoint inhibitor are administered simultaneously or sequentially.

The present invention provides the following.

[1] A pharmaceutical formulation comprising:
(A) a liposome composition in combination with (B) an immune checkpoint inhibitor, in which the liposome composition includes liposomes each having an inner water phase, and an aqueous solution constituting an outer water phase and having the liposomes dispersed therein, gemcitabine is encapsulated in a dissolved state in the liposomes, and the liposome composition and the immune checkpoint inhibitor are administered simultaneously or sequentially.

[2] The pharmaceutical formulation according to [1], in which the liposome composition is a liposome composition in which an osmotic pressure of the inner water phase of the liposome is 2 times or more and 8 times or less an osmotic pressure of the outer water phase, and a release rate of gemcitabine from the liposome is 10% by mass/24 hr or more and 70% by mass/24 hr or less at 37° C. in human plasma.

[3] The pharmaceutical formulation according to [1], in which the liposome composition is a liposome composition in which a content of cholesterols is 10 mol % or more and 35 mol % or less with respect to a total amount of lipid components of the liposome composition, and an osmotic pressure of the inner water phase is 2 times or more and 8 times or less an osmotic pressure of the outer water phase.

[4] The pharmaceutical formulation according to any one of [1] to [3], in which the immune checkpoint inhibitor includes at least one selected from a PD-1 inhibitor, a PD-L1 inhibitor, a PD-L2 inhibitor, or a CTLA-4 inhibitor.

[5] The pharmaceutical formulation according to [4], in which the immune checkpoint inhibitor includes at least one selected from a PD-1 inhibitor, a PD-L1 inhibitor, or a CTLA-4 inhibitor.

[6] The pharmaceutical formulation according to any one of [1] to [5], in which the administration is carried out at an effective dose and for an effective dosing period that exhibit a therapeutic synergistic effect.

[7] The pharmaceutical formulation according to any one of [1] to [6], in which a subject of administration has resistance to gemcitabine.

[8] A method for treating a subject suffering from cancer, the method comprising:
simultaneously or sequentially administering (A) a liposome composition and (B) an immune checkpoint inhibitor in combination to the subject at an effective dose and for an effective dosing period that exhibit a therapeutic synergistic effect,
in which the liposome composition includes liposomes each having an inner water phase, and an aqueous solution constituting an outer water phase and having the liposomes dispersed therein, and gemcitabine is encapsulated in a dissolved state in the liposomes.

[9] The treatment method according to [8], in which the liposome composition is a liposome composition in which an osmotic pressure of the inner water phase of the liposome is 2 times or more and 8 times or less an osmotic pressure of the outer water phase, and a release rate of gemcitabine from the liposome is 10% by mass/24 hr or more and 70% by mass/24 hr or less at 37° C. in human plasma.

[10] The treatment method according to [8], in which the liposome composition is a liposome composition in which a content of cholesterols is 10 mol % or more and 35 mol % or less with respect to a total amount of lipid components of the liposome composition, and an osmotic pressure of the inner water phase is 2 times or more and 8 times or less an osmotic pressure of the outer water phase.

[11] The treatment method according to any one of [8] to [10], in which the immune checkpoint inhibitor includes at least one selected from a PD-1 inhibitor, a PD-L1 inhibitor, a PD-L2 inhibitor, or a CTLA-4 inhibitor.

[12] The treatment method according to [11], in which the immune checkpoint inhibitor includes at least one selected from a PD-1 inhibitor, a PD-L1 inhibitor, or a CTLA-4 inhibitor.

[13] The treatment method according to any one of [8] to [12], in which a subject of administration has resistance to gemcitabine.

[14] A pharmaceutical formulation for use in the treatment method according to any one of [8] to [12], comprising:
a liposome composition for administration in combination with an immune checkpoint inhibitor,
in which the liposome composition includes liposomes each having an inner water phase, and an aqueous solution constituting an outer water phase and having the liposomes dispersed therein, and gemcitabine is encapsulated in a dissolved state in the liposomes.

The pharmaceutical formulation according to an aspect of the present invention is a pharmaceutical formulation including a liposome composition in combination with an immune checkpoint inhibitor, in which gemcitabine is encapsulated in a dissolved state in liposomes, and the liposome composition and the immune checkpoint inhibitor are administered simultaneously or sequentially, and has at least one effect of treating or preventing cancer.

In addition, the pharmaceutical formulation according to the aspect of the present invention has a long blood half-life of a liposome composition including gemcitabine in a dissolved state, maintains excellent properties of having a strong antitumor activity even in a small amount, and by administering a liposome composition and an immune checkpoint inhibitor in combination simultaneously or sequentially, has a significant and unexpected tumor growth inhibitory effect, which is superior to the effect in a case of either a liposome composition having gemcitabine encapsulated in a dissolved state in liposomes alone or an immune checkpoint inhibitor alone.

Furthermore, the pharmaceutical formulation according to the aspect of the present invention has a tumor growth inhibitory effect even at a low dose, which enables a desirable treatment that is highly safe, has a low physical burden, and is highly convenient for subjects including patients.

DESCRIPTION OF THE PREFERRED EMBODIMENTS

Figure 1:
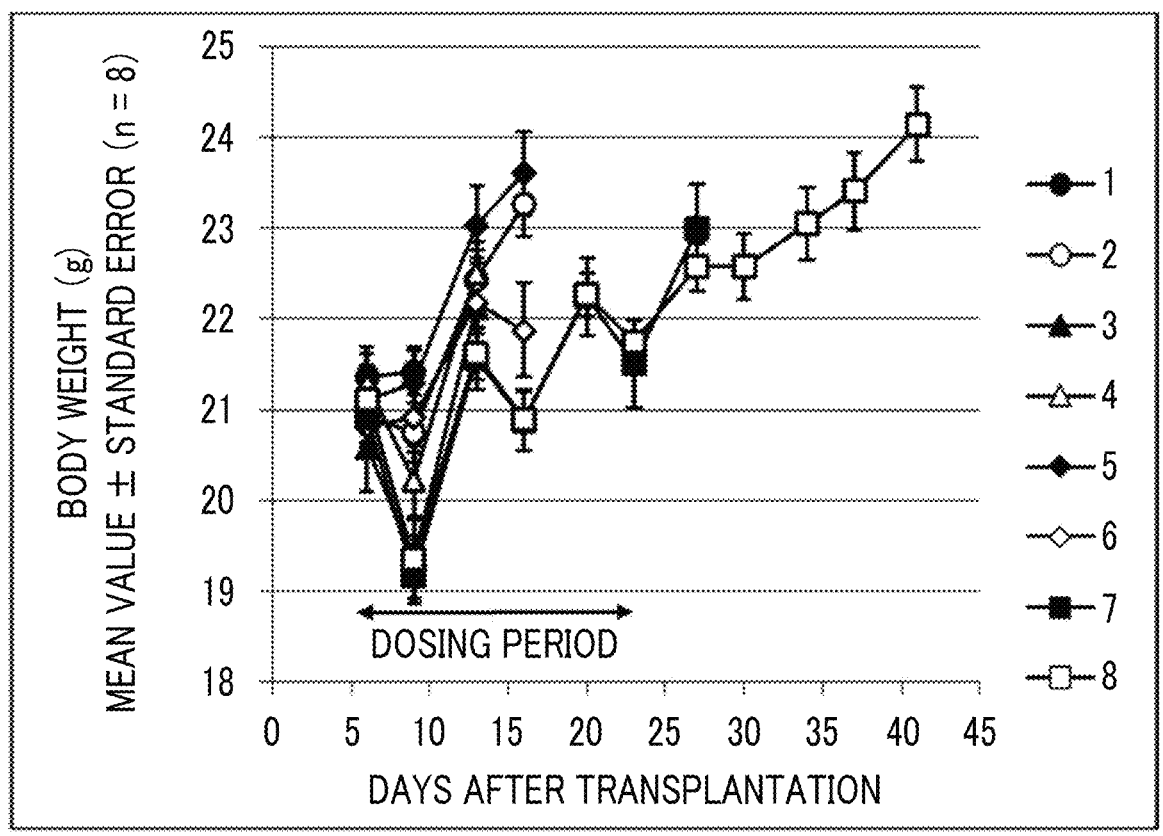
FIG. 1 shows changes in body weight in a drug efficacy test using a tumor-bearing model mouse with subcutaneous transplantation of EMT6.

Hereinafter, the present invention will be described in detail.

In the present specification, % means mass percentage unless otherwise specified. In the present specification, in a case where a plurality of substances corresponding to components are present in a composition, the amount of each component in the composition means a total amount of the plurality of substances present in the composition, unless otherwise specified.

In the present specification, each term has the following meaning unless otherwise specified.

The term "to" indicates a range including the numerical values described before and after "to" as a minimum value and a maximum value, respectively.

The subject includes humans and mammals other than humans. Examples of mammals other than humans include monkeys, dogs, cats, cows, horses, mice, and rats.

The treatment may be any treatment or therapy that achieves a desired therapeutic effect, for example, inhibition or delay of progression of a condition, and includes slowing down a rate of progression, pausing the rate of progression, improving the condition, healing or remitting the condition (whether partial or complete), preventing, delaying, reducing, or arresting one or a plurality of symptoms and/or signs of the condition, and prolonging a subject's survival over that expected in the absence of treatment.

The treatment also includes prevention. For example, treating a subject who is susceptible to or at risk of onset or recurrence of cancer may prevent or delay the onset or recurrence of cancer in the subject.

The treatment includes inhibition of cancer growth including complete remission of cancer, and/or inhibition of cancer metastasis. The cancer growth refers to the transformation of cancer into a more developed form. Examples of an index for measuring the inhibition of cancer growth include decreased survival of cancer cells, decreased tumor volume or morphology (for example, determined using computed tomography (CT), ultrasonography, or other diagnostic imaging methods), delayed tumor growth, destruction of tumor vasculature, improved scores of delayed hypersensitivity skin test, increased activity of cytolytic T-lymphocytes, and decreased levels of tumor-specific antigens.

In the present invention, tumor, malignant tumor, cancer, malignant neoplasm, carcinoma, sarcoma, and the like are collectively referred to as "tumor" or "cancer". In addition, the term "tumor" or "cancer" includes those that have recurred after the treatment of cancer. The term "tumor"

includes all malignant or benign neoplastic cell growth and proliferation, as well as pre-cancerous and cancerous cells and tissues.

The term "effective amount" is a dose required to achieve a desired therapeutic or prophylactic result, including the duration and amount of administration. The "effective amount" of the pharmaceutical formulation according to the embodiment of the present invention may vary depending on the disease state, age, sex, and body weight of a subject (or individual), the ability of the pharmaceutical formulation to elicit a desired response in the subject (or individual), and the like.

The term "co-administration" refers to administering a first therapy and a second therapy in a combination therapy at a time interval of about 15 minutes or less, such as any of about 10 minutes, about 5 minutes, or about 1 minute or less. In a case where the first therapy and the second therapy are administered simultaneously, the first therapy and the second therapy can be contained in the same composition (for example, a composition that contains both the first therapy and the second therapy), or can be contained in separate compositions (for example, the first therapy is contained in one composition and the second therapy is contained in another composition).

The term "sequential administration" refers to administering a first therapy and a second therapy in a combination therapy at a time interval of more than about 15 minutes, such as any of about 20 minutes, about 30 minutes, about 40 minutes, about 50 minutes, about 60 minutes or longer (1 day, 2 days, 3 days, 1 week, 2 weeks, 3 weeks, or the like). In the present invention, the sequential administration also includes first administration of the first therapy and first administration of the second therapy. In addition, in the present invention, the sequential administration also includes the administration of the second therapy after the administration of the first therapy (after a predetermined time (for example, after 1 week)). The first therapy and the second therapy may be contained in separate compositions, which may be contained in the same package or kit or may be contained in different packages or kits.

(Pharmaceutical Formulation According to Embodiment of Present Invention)

The pharmaceutical formulation according to the embodiment of the present invention is a pharmaceutical formulation including (A) a liposome composition in combination with (B) an immune checkpoint inhibitor, in which the liposome composition includes liposomes each having an inner water phase, and an aqueous solution constituting an outer water phase and having the liposomes dispersed therein, gemcitabine is encapsulated in a dissolved state in the liposomes, and the liposome composition and the immune checkpoint inhibitor are administered simultaneously or sequentially.

((A) Liposome Composition)

The liposome is a closed vesicular body formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside a closed vesicular body. In the present invention, the liposome composition refers to a composition including a liposome and an aqueous solution, components, and the like contained outside the liposome. The liposome may be single lamellar (which is also referred to as monolayer lamellar or unilamellar, and is a structure having a single bilayer membrane) or may be multilayered lamellar (which is also referred to as multilamellar and is an onion-like structure having multiple bilayer membranes where individual layers are compartmented by aqueous layers). In the present invention, the liposome is preferably a single lamellar liposome from the viewpoint of safety and stability in pharmaceutical applications. The "encapsulated" means taking a form in which a drug is contained in an inner water phase with respect to the liposome.

The size (average particle size) of the liposome is not particularly limited and is 2 to 200 nm, preferably 5 to 150 nm, more preferably 5 to 120 nm, and still more preferably 5 to 100 nm.

In a case of expecting an enhanced permeation and retention effect (EPR effect) described below, the size (average particle size) of the liposome is preferably substantially 50 to 200 nm in diameter, more preferably substantially 50 to 150 nm in diameter, and still more preferably substantially 50 to 100 nm in diameter. The term "substantially" means that at least 75% of the number of liposomes are within a specified diameter range. The "at least 75%" is more preferably at least 80% and still more preferably at least 90%.

In the present invention, the "average particle size of liposome" means an average particle size (preferably a cumulant average particle size) measured using a dynamic light scattering method unless otherwise specified. The "average particle size" can be measured by using an apparatus capable of measuring the average particle size by a light scattering method.

Lipid is included as a component (membrane component) that constitutes the lipid bilayer of the liposome. Any lipid soluble in a mixed solvent of a water-soluble organic solvent and an ester-based organic solvent can be used as the lipid. Examples of the lipid include a phospholipid, a lipid other than phospholipid, cholesterols, and derivatives thereof. These components may be constituted of a single component or a plurality of components.

Examples of the phospholipid include a natural or synthetic phospholipid such as phosphatidylcholine (lecithin), phosphatidyl glycerol, phosphatidic acid, phosphatidyl ethanolamine, phosphatidyl serine, phosphatidyl inositol, sphingomyelin, or cardiolipin, and a hydrogenated product thereof (for example, hydrogenated soy phosphatidylcholine (HSPC)). Above all, the phospholipid is preferably a hydrogenated phospholipid such as hydrogenated soy phosphatidylcholine, sphingomyelin, or the like, and more preferably hydrogenated soy phosphatidylcholine. In the present invention, the term "phospholipid" also includes phospholipid derivatives obtained by modifying a phospholipid.

The lipid other than phospholipid may be, for example, a phosphate-free lipid, examples of which include, but are not limited to, a glycerolipid that does not have a phosphate moiety in the molecule thereof and a sphingolipid that does not have a phosphate moiety in the molecule thereof. In the present invention, the term "lipid other than phospholipid" also includes derivatives of a lipid other than the phospholipid obtained by modifying a lipid other than phospholipid.

In a case where the lipid other than phospholipid contains a basic functional group, for example, in a case where it is a substance in which a compound having a basic functional group is bound to the lipid, the lipid is referred to as a cationized lipid. The cationized lipid can modify, for example, the membrane of the liposome, and can enhance the adhesiveness to the cells which are target sites.

Examples of cholesterols include cholesterol. It is effective to add cholesterol or the like in order to fill the deformation of the membrane caused by lipid. In connection with the liposome composition, the addition of cholesterols is expected to have an effect of lowering the fluidity of the membrane of the liposome, for example, by filling the gaps in the membrane of the liposome.

In the present invention, an unexpected effect was found that the rate of drug release in a mammal can be regulated by controlling the amount of cholesterols in an optimal range under high osmotic pressure conditions of the liposome composition.

In the present invention, the content of cholesterols is 10 to 35 mol %, preferably 15 to 25 mol %, and more preferably 17 to 21 mol % in total moles of the lipid components of the liposome composition (total lipids contained in the liposome composition).

In addition to the foregoing components, a hydrophilic polymer or the like for improving retention in blood, fatty acid, diacetyl phosphate, or the like as a membrane structure stabilizer, or α-tocopherol or the like as an antioxidant may be added to the liposome. In the present invention, it is preferable not to include an additive such as a dispersion aid which is not recognized for use in intravenous injection in pharmaceutical applications, for example, a surfactant.

The liposome according to the embodiment of the present invention preferably contains a phospholipid, a lipid other than phospholipid, cholesterols, and derivatives thereof, in which a phospholipid, a lipid other than phospholipid, and cholesterols are modified with a hydrophilic polymer.

The hydrophilic polymer is not particularly limited, and examples thereof include polyethylene glycols, polyglycerins, polypropylene glycols, polyvinyl alcohols, styrene-maleic acid anhydride alternating copolymers, polyvinylpyrrolidones, and synthetic polyamino acids. The hydrophilic polymers may be used alone or in combination of two or more thereof. Among these, from the viewpoint of retention in blood of a preparation, polyethylene glycols, polyglycerins, and polypropylene glycols are preferable, and polyethylene glycol (PEG), polyglycerin (PG), and polypropylene glycol (PPG) are more preferable. Polyethylene glycol (PEG) is general-purpose and is preferable since it has an effect of improving retention in blood.

The molecular weight of PEG is not particularly limited, but the molecular weight of PEG is 500 to 10,000 daltons, preferably 1,000 to 7,000 daltons, and more preferably 2,000 to 5,000 daltons.

In the liposome according to the embodiment of the present invention, it is preferable to use a lipid modified with PEG (PEG-modified lipid) together with the main lipid included in the liposome.

Examples of the PEG-modified lipid include 1,2-distearoyl-3-phosphatidylethanolamine-polyethylene glycols such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.), and distearoyl glycerol-PEG2000 (manufactured by Nippon Oil & Fats Co., Ltd.).

These PEG-modified lipids may be added so as to be contained in an amount of 0.3% to 50% by mass, preferably 0.5% to 30% by mass, and more preferably 1% to 20% by mass with respect to the total amount of lipids.

In the liposome according to the embodiment of the present invention, a lipid combination of hydrogenated soy phosphatidylcholine (a main lipid included in the liposome), 1,2-distearoyl-3-phosphatidylethanolamine-polyethylene glycol (a lipid used in combination with the main lipid), and cholesterol is preferable.

The liposome composition according to the embodiment of the present invention preferably contains no anionic polymer (polyanion).

The gemcitabine applied to the pharmaceutical formulation according to the embodiment of the present invention will be described. Gemcitabine has a chemical name of (+)-2'-deoxy-2',2'-difluorocytidine and is an anticancer agent having an antimetabolic action. In the present invention, gemcitabine may be gemcitabine itself, a pharmaceutically acceptable salt, or a prodrug that releases gemcitabine in vivo. In the present invention, it is preferable to use gemcitabine hydrochloride.

The gemcitabine encapsulated in the liposome according to the embodiment of the present invention exists in a dissolved state in the inner water phase of the liposome. Here, the term "dissolved state" means that, in a case where the amount of the drug loaded with respect to the volume of the liposome is equal to or lower than the saturated solubility of the drug in the composition liquid of the inner water phase, the drug is considered to be encapsulated in a dissolved state.

In addition, even in a case where the amount of the drug loaded is equal to or higher than the saturated solubility, gemcitabine is considered to be encapsulated in a dissolved state in a case where drug crystals are not observed by Cryo-TEM and a diffraction pattern due to a crystal lattice is not observed by XRD measurement.

(Method for Producing Liposome Composition)

The method for producing the liposome according to the embodiment of the present invention is not particularly limited as long as it is a method capable of producing a liposome composition having gemcitabine encapsulated in a dissolved state in liposomes. Each step of the method for producing a liposome composition described in detail below can be carried out with reference to, for example, WO2015/166985A and WO2015/166986A.

In the present invention, preferred is a method for producing a liposome composition including an emulsifying step of emulsifying a lipid dissolved in an organic solvent to form a liposome without undergoing a drying-solidification step, a drug loading step of encapsulating a water-soluble drug in the liposome obtained in the emulsifying step, and an osmotic pressure adjusting step of adjusting the osmotic pressure of the inner water phase of the liposome to 2 times or more and 8 times or less the osmotic pressure of the outer water phase.

The method for producing a liposome composition may include other steps such as an evaporation step of evaporating the organic solvent used in the emulsifying step, if necessary.

In the emulsifying step of emulsifying a lipid dissolved in an organic solvent to form a liposome without undergoing a drying-solidification step, there is no limitation as long as it is an emulsifying step. Preferably, it is a step of applying high shear and making the particles fine by an emulsifying step including an organic solvent. If necessary, evaporation (desolvation) of the organic solvent used in the emulsifying step may be carried out to form liposomes.

(Emulsifying Step)

In the emulsifying step, an oil phase in which at least one lipid is dissolved in an organic solvent is mixed with a water phase to prepare an aqueous solution containing lipids, which is then emulsified with stirring. An oil phase where lipid has been dissolved in an organic solvent and a water phase are mixed, stirred, and emulsified to thereby prepare an emulsion where the oil phase and the water phase are emulsified in an O/W type. After mixing, liposomes are formed by removing a portion or all of the organic solvent derived from the oil phase by an evaporation step which will be described below. Alternatively, a portion or all of the organic solvent in the oil phase is evaporated in the course of the stirring-emulsification to form liposomes.

As a method of stirring, ultrasonic waves or mechanical shearing force is used for particle miniaturization. In addition, extruder processing or microfluidizer processing of allowing to pass through a filter having a certain pore size can be carried out for uniformity of particle sizes. Use of an extruder or the like can result in decomposition of secondarily formed multivesicular liposomes into univesicular liposomes.

In the present invention, from the viewpoint of simplification of the manufacturing process, it is preferable to use the liposome in a state in which a drug is not loaded in the next step without the extrusion treatment.

(Oil Phase)

As the organic solvent for use as the oil phase, a mixed solvent of a water-soluble organic solvent and an ester-based organic solvent is used. In the present invention, it is preferable to use substantially no organic solvent such as chloroform, methylene chloride, hexane, or cyclohexane as the organic solvent, and it is more preferable not to use any of these organic solvents.

The water-soluble organic solvent is not particularly limited, but is preferably an organic solvent having a property of mixing freely with water. Specific examples of the water-soluble organic solvent include alcohols such as methanol, ethanol, n-propanol, isopropanol, n-butanol, isobutanol, and t-butanol; glycols such as glycerin, ethylene glycol, and propylene glycol; and polyalkylene glycols such as polyethylene glycol. Among these, alcohols are preferred.

The ester-based organic solvent is not particularly limited, but is preferably an ester obtained by the reaction of an organic acid and an alcohol. Specifically, the ester-based organic solvent is preferably at least one selected from ethyl acetate, methyl acetate, isopropyl acetate, t-butyl acetate, or methyl propionate.

The concentration of the lipid is not particularly limited and can be appropriately adjusted. In a case of a solution using a mixed liquid of a water-soluble organic solvent and an ester-based organic solvent as a solvent, the concentration of the lipid may be 40 g/L to 250 g/L and preferably 100 g/L to 200 g/L.

(Water Phase)

The water phase refers to an outer water phase and an inner water phase. The outer water phase in the present invention means an aqueous solution in which liposomes are dispersed. For example, in a case of an injection, a solution occupying the outside of the liposome of a dispersion liquid of liposomes packaged and stored in a vial or prefilled syringe becomes an outer water phase. In addition, similarly for a liquid to be dispersed at the time of use in a case of being administered by means of an attached liquid for dispersion or other dissolution liquid, a solution occupying the outside of the liposome of a dispersion liquid of liposomes becomes an outer water phase.

The inner water phase in the present invention refers to a water phase in the closed vesicle across the lipid bilayer membrane. In a case of producing liposomes, water (distilled water, water for injection, or the like), physiological saline, various buffer solutions, aqueous sugar solutions, and mixtures thereof (aqueous solvents) are preferably used as the aqueous solution (outer water phase) in which the liposomes are dispersed.

The buffer solution is not limited to organic and inorganic buffer solutions, and a buffer solution having a buffering action in the vicinity of a hydrogen ion concentration close to that of the body fluid is suitably used and examples thereof include a phosphate buffer solution, a Tris buffer solution, a citrate buffer solution, an acetate buffer solution, and a Good's buffer solution. The pH of the water phase is not particularly limited, but may be 5 to 9 and preferably 7 to 8. For example, it is preferable to use a phosphate buffer solution (for example, pH=7.4). The inner water phase of the liposome may be an aqueous solution in which the liposomes are dispersed in a case of producing liposomes, or may be water, physiological saline, various buffer solutions, aqueous sugar solutions, and mixtures thereof which are newly added. The water used as an outer water phase or an inner water phase is preferably free from impurities (dust, chemicals, or the like). The physiological saline refers to an inorganic salt solution adjusted to be isotonic with the human body fluid, and may further have a buffering function. Examples of the physiological saline include saline containing 0.9 w/v % of sodium chloride, phosphate-buffered saline (hereinafter, also referred to as PBS), and Tris-buffered saline.

(Evaporation Step)

In the present invention, an evaporation step may be provided if necessary. In the evaporation step, the organic solvent is evaporated from the aqueous solution containing liposomes obtained in the emulsifying step. The evaporation step includes at least one of a step of evaporating and forcibly removing a portion or all of the organic solvent derived from the oil phase, or a step in which a portion or all of the organic solvent in the oil phase evaporates spontaneously during the course of stirring/emulsification.

The aqueous solution containing liposomes prepared through the emulsifying step may be subjected to a post-treatment by a method such as centrifugation, ultrafiltration, dialysis, gel filtration, or freeze-drying, for the purpose of removing components not contained in the liposomes or adjusting the concentration and osmotic pressure. The obtained liposomes can be made uniform in particle size by using dialysis, filtration, extrusion, or the like. In the method for producing the liposome composition according to the embodiment of the present invention, it is preferable to prepare empty liposomes in a state where no drug is loaded without extrusion.

(Extrusion)

The extrusion refers to a step of passing liposomes through a filter having a fine pore to apply a physical shearing force, thereby carrying out microparticulation of the liposomes. In a case where the liposomes are passed through, rapid microparticulation of the liposomes may be achieved by keeping the liposome dispersion liquid and the filter at a temperature higher than or equal to the phase transition temperature of the membrane constituting the liposome.

(Drug Loading Step)

In the drug loading step according to the embodiment of the present invention, in a case of encapsulating a water-soluble drug in liposomes, the drug can be encapsulated in the liposomes such a manner that the drug is dissolved in an aqueous medium that is hydrated and swelled, and the resulting drug solution is heated to a temperature higher than or equal to the phase transition temperature, followed by ultrasonication, extrusion, or the like to encapsulate the drug in the inner water phase of the liposome. Alternatively, the drug may be dissolved in the water phase at the time of lipid emulsification to encapsulate the drug in the inner water phase.

(Osmotic Pressure Adjusting Step)

In the present invention, the osmotic pressure adjusting step makes the inner water phase of the liposome hypertonic (pressure difference), whereby the drug is easily released. The release rate can be controlled by setting the osmotic pressure. The osmotic pressure adjusting step is not particularly limited, but a method such as dialysis can be adopted after the drug loading step. For the osmotic pressure adjusting step, reference can be made to WO2015/166985A or WO2015/166986A.

In the present invention, for example, in a case where the liposome composition according to the embodiment of the present invention is used as a drug delivery system, the required amount of the required drug can be released in a target affected area by controlling the release. Meanwhile, hypertonic liposomes release a drug easily, whereas the drug also easily leaks out of the liposomes during storage thereof, which makes it difficult to achieve both drug releasability and storage stability. The liposome composition according to the embodiment of the present invention has an unexpected effect that both drug releasability and storage stability can be achieved at the same time, by setting for the liposome having an inner water phase, which is obtained from the emulsified lipid, such that the osmotic pressure of the inner water phase is 2 times or more and 8 times or less the osmotic pressure of the outer water phase.

In the liposome composition according to the embodiment of the present invention, the osmotic pressure of the inner water phase is 2 times or more and 8 times or less, preferably 2.5 times to 6 times, and more preferably 3 times to 5 times the osmotic pressure of the outer water phase. It is generally known that, by making the osmotic pressure of the inner water phase 2 times or more the osmotic pressure of the outer water phase, the lipid bilayer membrane of the liposome exhibits a structure such as a bilayer membrane structure or an interlaced finger-like structure. In a case where the osmotic pressure of the inner water phase is 2 times or more that of the outer water phase, the liposomes begin to change from a bilayer membrane structure to an interlaced finger-like structure. In the present invention, various lipid conditions may be set in order to obtain a suitable interlaced finger-like structure, but it is preferable to control by adjusting the cholesterol ratio. As a result, it is possible to obtain a liposome composition capable of achieving both drug releasability and storage stability.

In the liquid obtained after the final drug loading step, the solutes of the outer water phase and the inner water phase are homogenized, and therefore the osmotic pressure at that time can be defined as the osmotic pressure of the inner water phase of the completed liposome composition. However, in the subsequent replacement/osmotic pressure adjusting step by dialysis of the outer water phase, the heating operation is limited to a case where the solute of the inner water phase is sufficiently retained, such as the temperature being kept equal to or lower than the phase transition temperature of the lipid. In addition, the osmotic pressure of the outer water phase can be defined by the osmotic pressure of a dialysis liquid used in the final dialysis step. However, it is limited to a case where the outer water phase can be sufficiently replaced with a dialysis liquid. Alternatively, the osmotic pressure of the inner water phase and the outer water phase can also be obtained in such a manner that the completed solution of the liposome composition is subjected to centrifugation or ultrafiltration to quantify the composition concentration of the solute of the outer water phase and the composition concentration of the solute of the inner water phase and measure the osmotic pressure of the composition liquid.

The osmotic pressure may be measured according to the osmotic pressure measuring method described in the 16th revised Japanese Pharmacopoeia. Specifically, the osmolality can be determined by measuring a degree of freezing point (ice point) depression of water. In addition, the degree of freezing point depression of water is defined by a solute molar concentration, and the osmolality can also be determined from the solute molar concentration.

The osmotic pressure of the outer water phase in the present invention has an important effect on the living body during administration. In a case where the osmotic pressure of the outer water phase greatly deviates from the osmotic pressure of the body fluid, hemolysis and pain occur due to the movement of water in each tissue. Therefore, the osmotic pressure of the outer water phase in the present invention is preferably 200 to 400 mOsmol/L, more preferably 250 to 350 mOsmol/L, and most preferably isotonic with the body fluid.

(Sterile Filtration)

The aqueous solution containing liposomes obtained by the method for producing a liposome composition according to the embodiment of the present invention is preferably subjected to sterile filtration. Regarding the filtration method, it is possible to remove unwanted materials from an aqueous solution containing liposomes by using a hollow fiber membrane, a reverse osmosis membrane, a membrane filter (preferably a 0.2 µm filtration sterilization filter), or the like.

(Additives and the Like for Liposome Composition According to Embodiment of Present Invention)

The liposome composition according to the embodiment of the present invention can be prepared by adding additives including a medium such as an aqueous solution, a salt, a preservative, a buffer, and the like which are pharmaceutically acceptable, for administration to a subject. Examples of an aqueous carrier include water, an alcohol/water solution, physiological saline, and a parenteral medium such as sodium chloride or glucose. Examples of an intravenous medium include water and a nutritional supplement. Examples of the preservative include an antibacterial agent, an antioxidant, a chelating agent, and an inert gas. The pH of the liposome composition and the concentrations of the various components can be adjusted to the desired values.

The administration method of the liposome composition according to the embodiment of the present invention is preferably parenteral administration. For example, intravenous injection such as intravenous drip, intramuscular injection, intraperitoneal injection, subcutaneous injection, intraocular injection, and intrathecal injection can be selected. A specific administration method of the liposome composition may be, for example, administration by syringe or intravenous drip. In a case where the liposome composition according to the embodiment of the present invention is administered simultaneously or sequentially in combination with the immune checkpoint inhibitor according to the embodiment of the present invention, the effective dose and dosing period of the liposome composition can be selected so as to exhibit a therapeutic synergistic effect. However, the present invention is not limited to these doses.

(Container for Liposome Composition According to Embodiment of Present Invention)

The container for the liposome composition according to the embodiment of the present invention is not particularly limited, and it is preferably made out of a material having low oxygen permeability. Examples of the container include a plastic container, a glass container, and a laminated film bag with an aluminum foil, an aluminum vapor deposition film, an aluminum oxide vapor deposition film, a silicon oxide vapor deposition film, a polyvinyl alcohol, an ethylene-vinyl alcohol copolymer, a polyethylene terephthalate, a polyethylene naphthalate, a polyvinylidene chloride, or the like as a gas barrier layer. The container can be shielded from light by employing, for example, a bag using a colored glass, an aluminum foil, an aluminum vapor deposition film, or the like, if necessary. In order to prevent oxidation due to oxygen existing in the space inside the container, it is preferable to replace the gas in the container space and drug solution with an inert gas such as nitrogen. For example, an injection solution is bubbled with nitrogen, whereby the filling of the injection solution into a container can be carried out under a nitrogen atmosphere.

(Release Rate)

The release rate means an amount of drug (here, gemcitabine) that goes out of the liposome per unit time. In the present invention, the release rate in plasma at 37° C. is preferably 10% by mass/24 hr or more and 70% by mass/24 hr or less, more preferably 20% by mass/24 hr or more and 60% by mass/24 hr or less, and still more preferably 20% by mass/24 hr or more and 50% by mass/24 hr or less.

Since the release rate depends on the temperature, it is preferable to measure the release rate under constant temperature conditions. For example, in a case of human, the temperature is not particularly limited, but it is preferable to measure the release rate within the range of body temperature (35° C. or higher and 38° C. or lower).

In a case where the release rate is less than 10% by mass/24 hr, sufficient in vivo exposure time as an anticancer agent may not be obtained, and therefore the expected drug efficacy may not be obtained in many cases; and unexpected toxicity may be manifested in some cases due to unnecessary long-term in vivo retention of liposomes containing an anticancer agent, and accumulation of the liposomes in tissues such as skin where the liposomes are not easily distributed. In addition, in a case where the release rate is more than 70% by mass/24 hr, the amount of drug exposed per unit time increases and the maximum blood concentration of the drug becomes high, resulting in increased toxicity; and the leaked drug is distributed to tissues other than the tumor site or is rapidly metabolized to reduce its retention in blood, which is thus not preferable.

(Tumor Volume)

In the present invention, a tumor can be transplanted into a model animal (preferably a mouse or a rat) in order to measure the tumor volume. Inhibition of tumor volume growth depends on the drug used, the combination of lipids or the like constituting the liposome, and the effective amount. The inhibition of tumor volume growth refers to at least one of inhibiting tumor growth, achieving tumor stasis, or achieving substantial or complete tumor regression.

In a case where the liposome composition according to the embodiment of the present invention is administered to a subject such as a mammal, the administration can be started after assignment of model animals into a treatment group and a control group, and then transplantation of tumor cells into the subject animals, for example, growth of the tumor cells to 100 to 1,000 mm such that the tumor cells settle.

For example, in a case where the model animal is a mouse, mice in each group can be weighed as a whole daily until the animals reach a minimum body weight, as an evaluation of the liposome composition according to the embodiment of the present invention. Tumors can be measured with calipers or the like until final sacrifice of the animals for sampling, until tumors reach 2,000 mm$^3$, or until the animals die. The tumor volume in a mammalian subject can be measured using any method recognized in the related art. For example, caliper measurement can be used to evaluate the tumor volume using the expression: $(a \times b^2) \times 0.5$, where "a" is a maximum diameter and "b" is a minor axis length. In addition, in a case of humans, the tumor volume can be measured by a technique for diagnostic imaging such as computer tomography (CT) scanning or magnetic resonance imaging (MRI) scanning.

Tumors applied to the pharmaceutical formulation according to the embodiment of the present invention are not particularly limited, and the pharmaceutical formulation according to the embodiment of the present invention can be widely applied to treatments of common cancers such as breast cancer, non-small cell lung cancer, small cell lung cancer, colorectal cancer, non-Hodgkin's lymphoma (NHL), renal cell carcinoma, prostate cancer, hepatocellular carcinoma, gastric cancer, pancreatic cancer, soft tissue sarcoma, Kaposi's sarcoma, carcinoid carcinoma, head and neck cancer, melanoma, ovarian cancer, bile duct cancer, mesothelioma, and multiple myeloma. The pharmaceutical formulation according to the embodiment of the present invention is preferably used for treating a tumor disease for which a therapy using gemcitabine is effective, and more preferably for treating a tumor disease resistant to gemcitabine.

The resistance means that cancer cells show resistance to an anticancer agent and includes the natural resistance to which the anticancer agent does not work from the beginning of treatment and a condition in which an initially effective anticancer agent is ineffective or diminishes in effect as the treatment continues. Specifically, the resistance refers to a property that cells did not show an appropriate response to an anticancer agent in that the cells responded to the anticancer agent in the early stage, but then showed a decrease in responsiveness during the treatment, or in that the cells continued to proliferate during the treatment with the anticancer agent.

((B) Immune Checkpoint Inhibitor)

The term "immune checkpoint inhibitor" refers to a drug that inhibits binding of an immune checkpoint to a ligand thereof to inhibit signal transduction by the immune checkpoint. Examples of the immune checkpoint inhibitor include immune checkpoints and ligands thereof that are presented on the surface of T cells, specifically, molecules such as PD-1, CTLA-4, TIM3, LAGS, PD-L1, PD-L2, BTNL2, B7-H3, B7-H4, CD48, CD80, 2B4, BTLA, CD160, CD60, CD86, and VISTA, but the present invention is not limited thereto. In the present invention, the immune checkpoint inhibitor is preferably an agent that inhibits at least one selected from programmed cell death protein 1 (PD-1) or a ligand thereof PD-L1 or PD-L2, or cytotoxic T lymphocyte antigen 4 (CTLA-4). PD-1 (Programmed death-1, CD279) is a 50-55 kDa type I membrane protein belonging to the CD28/CTLA-4 family that acts to enhance and/or suppress lymphocyte activation signals. In addition, PD-L1 (also known as B7-H1 or CD274) and PD-L2 (also known as B7-DC or CD273) are ligands of PD-1 expressed on the surface of antigen-presenting cells.

The immune checkpoint inhibitor may be any substance which is capable of binding to an immune checkpoint and a ligand thereof, which are presented on the surface of T cells. For example, at least one of an anti-PD-L1 antibody, an anti-PD-L2 antibody, or an anti-CTLA-4 antibody known in the related art can be used. An anti-PD-L1 antibody, an anti-PD-L2 antibody, an anti-CTLA-4 antibody, and the like are commercially available from, for example, Bio X Cell. Specific examples of the immune checkpoint inhibitor include, but are not limited to, nivolumab, pembrolizumab, ipilimumab, atezolizumab, durvalumab, avelumab, tremelimumab, and abatacept. In addition, it is also possible to use at least one of an anti-PD-1 antibody, an anti-PD-L1 antibody, or an anti-PD-L2 antibody in combination with an anti-CTLA-4 antibody, as the immune checkpoint inhibitor.

The immune checkpoint inhibitor according to the embodiment of the present invention can be administered to a subject by oral or parenteral administration and preferably parenteral administration. The administration method specifically includes injection administration, nasal administration, pulmonary administration, transdermal administration, and the like. Examples of the injection administration include intravenous injection, intramuscular injection, intraperitoneal injection, and subcutaneous injection. In addition, the administration method can be appropriately selected depending on the age and symptoms of the subject. The dose can be selected, for example, in the range of 0.0001 mg to 1,000 mg per kg subject body weight per administration. Alternatively, the dose can be selected within the range of 0.001 mg/body to 100,000 mg/body per patient. In a case where the immune checkpoint inhibitor according to the embodiment of the present invention is administered simultaneously or sequentially in combination with the liposome composition according to the embodiment of the present invention, the effective dose and dosing period of the immune checkpoint inhibitor can be selected so as to exhibit a therapeutic synergistic effect. However, the present invention is not limited to these doses.

(Additives and the Like for Immune Checkpoint Inhibitor)

The immune checkpoint inhibitor according to the embodiment of the present invention can be prepared by adding additives including a medium such as a pharmaceutically acceptable aqueous solution, a salt, a preservative, a buffer, and the like for administration thereof to a subject, in addition to an anti-PD-1 antibody, an anti-PD-L1 antibody, an anti-PD-L2 antibody, an anti-CTLA-4 antibody, and the like. Specifically, the above-mentioned additives and the like of the liposome composition according to the embodiment of the present invention can be similarly applied.

The pharmaceutical formulation according to the embodiment of the present invention can be used to treat a subject having a cancer that is refractory to treatment with an immune checkpoint inhibitor. For example, a subject for whom a desired drug efficacy was not observed by the administration of the immune checkpoint inhibitor can be treated with the pharmaceutical formulation according to the embodiment of the present invention.

Although the mechanism of action of the pharmaceutical formulation according to the embodiment of the present invention is unknown, it is presumed to be as follows, but the present invention is not limited thereto. It is presumed that the pharmaceutical formulation according to the embodiment of the present invention has an excellent growth inhibitory effect on tumor cells, due to an enhanced permeation and retention effect (EPR effect) in which liposomes encapsulating gemcitabine in a dissolved state permeate through the interstitial spaces of endothelial cells that make up neovascular vessels existing around tumors and are accumulated and retained in tumor tissues.

In addition, it is presumed that the immune checkpoint inhibitor enhances the immunity against cancer by inhibiting the interaction with an immune checkpoint molecule such as PD-1 or a ligand thereof PD-L1, or CTLA-4, whereby the progression of cancer can be suppressed or the cancer can be treated.

Furthermore, the pharmaceutical formulation according to the embodiment of the present invention has a strong antitumor activity even with a small amount of gemcitabine by simultaneously or sequentially administering a liposome composition containing gemcitabine in a dissolved state and an immune checkpoint inhibitor in combination. In addition, the pharmaceutical formulation according to the embodiment of the present invention has a tumor growth inhibitory effect superior to that of the treatment with a liposome composition alone or an immune checkpoint inhibitor alone; or as shown in the Examples, the pharmaceutical formulation according to the embodiment of the present invention has a remarkable and unexpected effect that complete remission is achieved in 2 out of 8 cases of application to mice.

EXAMPLES

Hereinafter, the present invention will be specifically described with reference to Examples, but the present invention is not limited thereto. It is understood that the present invention can be variously changed and modified by those skilled in the art. Unless such changes and modifications depart from the scope of the present invention, those changes and modifications are included in the present invention. Various reagents used in the Examples are commercially available unless otherwise specified.

(Composition of Gemcitabine-Containing Liposome Composition (Hereinafter, Also Referred to as Liposome Composition According to Embodiment of Present Invention or Lipo))

Gemcitabine hydrochloride: 0.57 mg/mL
HSPC (Note 1): 11.3 mg/mL
MPEG-DSPE (Note 2): 2.91 mg/mL
Cholesterol: 1.39 mg/mL
Sucrose: 94 mg/mL
L-histidine: 1.55 mg/mL
Sodium chloride: 0.188 mg/mL
pH adjusting agent: q.s.
(Note 1) hydrogenated soy phosphatidylcholine
(Note 2) N-(carbonyl-methoxypolyethylene glycol 2000)-1,2-distearoyl-sn-glycero-3-phosphoethanolamine sodium salt Gemcitabine hydrochloride was obtained from Teva API, Inc. HSPC and MPEG-DSPE were obtained from NOF Corporation. For other reagents, commercially available products conforming to the United States Pharmacopeia were used.

(Physical Properties of Gemcitabine-Containing Liposome Composition)

The osmotic pressure of the inner water phase of the liposome was 3.8 times the osmotic pressure of the outer water phase.

The release rate of gemcitabine from liposomes was 25%/24 hr at 37° C. in human plasma, the content of cholesterols was 18.9 mol % with respect to the total amount of lipid components of the liposome composition, and the average particle size of the liposome was 77 nm.

As the anti-PD-1 antibody, (Bio X Cell, BE0146) was used. As the anti-PD-L1 antibody, (Bio X Cell, BE0101) was used. As the isotype control antibody, (Bio X Cell, BE0090) was used. 5% glucose solution for injection (5% Glu) is an aqueous solution of glucose 5 g/100 mL. EMT6 tumor cells (ATCC, CRL-2755) are derived from mouse mammary gland and are gemcitabine-resistant tumor cells.

Example 1

Drug efficacy test with combined use of PD-L1 in tumor-bearing model mouse with subcutaneous transplantation of EMT6

An anti-PD-L1 antibody (hereinafter, also referred to as PD-L1), gemcitabine (hereinafter, also referred to as Gem), and gemcitabine-containing liposome composition (hereinafter, also referred to as liposome composition according to the embodiment of the present invention) were used as test substances. Gemcitabine hydrochloride (manufactured by Teva Pharmaceutical Industries Ltd.) dissolved in physiological saline was used as Gem. The liposome composition according to the embodiment of the present invention was diluted with a 5% glucose solution for injection (hereinafter, also referred to as 5% Glu; 0.05 g/mL) prior to use.

$3 \times 10^6$ EMT6 cells, which are a mouse breast cancer cell line, were subcutaneously transplanted into the flank of female Balb mice to form subcutaneous tumors. Using the tumor volume as an index, inhibitory effects of combined administration of PD-L1 and Gem and combined administration of PD-L1 and the liposome composition according to the embodiment of the present invention on subcutaneous tumors were evaluated.

PD-L1 and an isotype control antibody thereof (hereinafter, also referred to as Iso antibody) were intraperitoneally administered twice a week for a total of 3 weeks, and Gem, the liposome composition according to the embodiment of the present invention, and a solvent therefor (5% Glu) were administered once a week by tail vein administration for a total of 3 weeks.

After the 3-week administration was completed, the drug was discontinued, and the tumor volume measurement was continued for 2 weeks. Test subjects with a tumor volume of more than 10% of body weight were euthanized during the test, and drug efficacy analysis was carried out based on the survival rate (tumor-free survival %).

Group configuration was set to a combination of 5% Glu and Iso antibody (10 mg/kg) for Group 1, a combination of 5% Glu and PD-L1 (10 mg/kg) for Group 2, a combination of Gem (240 mg/kg) and Iso antibody (10 mg/kg) for Group 3, a combination of Gem (240 mg/kg) and PD-L1 (10 mg/kg) for Group 4, a combination of the liposome composition according to the embodiment of the present invention (1 mg/kg) and Iso antibody (10 mg/kg) for Group 5, a combination of the liposome composition according to the embodiment of the present invention (1 mg/kg) and PD-L1 (10 mg/kg) for Group 6, a combination of the liposome composition according to the embodiment of the present invention (4 mg/kg) and Iso antibody (10 mg/kg) for Group 7, and a combination of the liposome composition according to the embodiment of the present invention (4 mg/kg) and PD-L1 (10 mg/kg) for Group 8.

Groups 1 to 5 and 7 are Comparative Examples, and Groups 6 and 8 are Examples. The upper limit of the dose of each drug was set as a dose that does not reach the minimum body weight, assuming that the amount at which the weight loss rate does not exceed 20% is a maximum tolerable dose (MTD). The group configuration and dose are shown in Table 1. In Table 1, "Dose" represents an amount as an active form of gemcitabine, "Twice/3W" represents twice-weekly administration for a total of 3 weeks, "Once/3W" represents once-weekly administration for a total of 3 weeks, "Abdomen" represents intraperitoneal administration, "Tail" represents tail vein administration, and "Lipo" represents the liposome composition according to the embodiment of the present invention. In addition, Lipo (1) and Lipo (4) mean that the liposome composition according to the embodiment of the present invention was administered to a subject at a dose of 1 mg/kg and a dose of 4 mg/kg, respectively.

TABLE 1

| Group | Test substance | Dose (mg/kg/administration) PD-L1 | Dose (mg/kg/administration) Gemcitabine | PD-L1 and Iso antibody Administration route | PD-L1 and Iso antibody Administration schedule | Gem, Liposome composition, and 5% Glu Administration route | Gem, Liposome composition, and 5% Glu Administration schedule | Dosage (mL/kg) |
|---|---|---|---|---|---|---|---|---|
| 1 | 5% Glu + Iso antibody | 0 | 0 | Abdomen | Twice/3W | Tail | Once/3W | 10 |
| 2 | 5% Glu + PD-L1 | 10 | 0 | Abdomen | Twice/3W | Tail | Once/3W | 10 |
| 3 | Gem + Iso antibody | 0 | 240 | Abdomen | Twice/3W | Tail | Once/3W | 10 |
| 4 | Gem + PD-L1 | 10 | 240 | Abdomen | Twice/3W | Tail | Once/3W | 10 |
| 5 | Lipo (1) + Iso antibody | 0 | 1 | Abdomen | Twice/3W | Tail | Once/3W | 10 |
| 6 | Lipo (1) + PD-L1 | 10 | 1 | Abdomen | Twice/3W | Tail | Once/3W | 10 |
| 7 | Lipo (4) + Iso antibody | 0 | 4 | Abdomen | Twice/3W | Tail | Once/3W | 10 |
| 8 | Lipo (4) + PD-L1 | 10 | 4 | Abdomen | Twice/3W | Tail | Once/3W | 10 |

Figure 2:
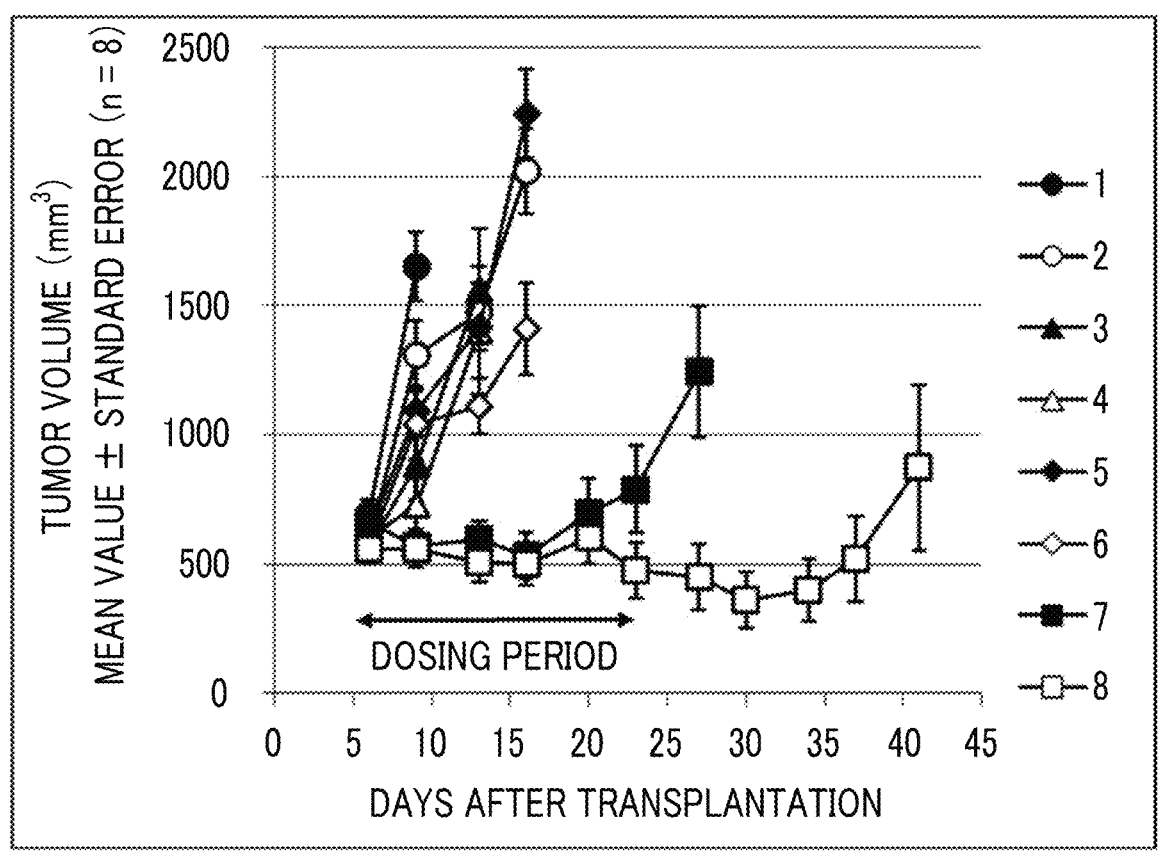
FIG. 2 shows changes in tumor volume in a drug efficacy test using a tumor-bearing model mouse with subcutaneous transplantation of EMT6.
Figure 3:
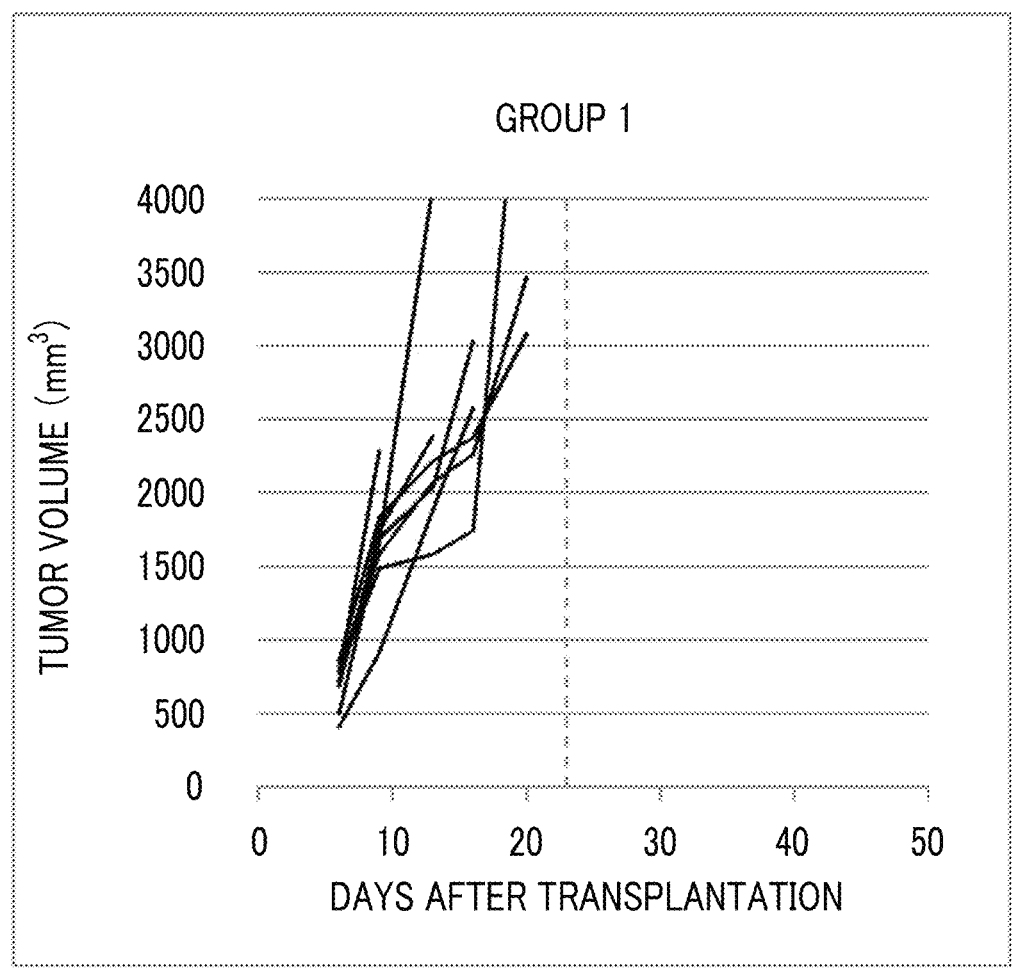
FIG. 3 shows changes in tumor volume by individual in a drug efficacy test using a tumor-bearing model mouse with subcutaneous transplantation of EMT6.
Figure 4:
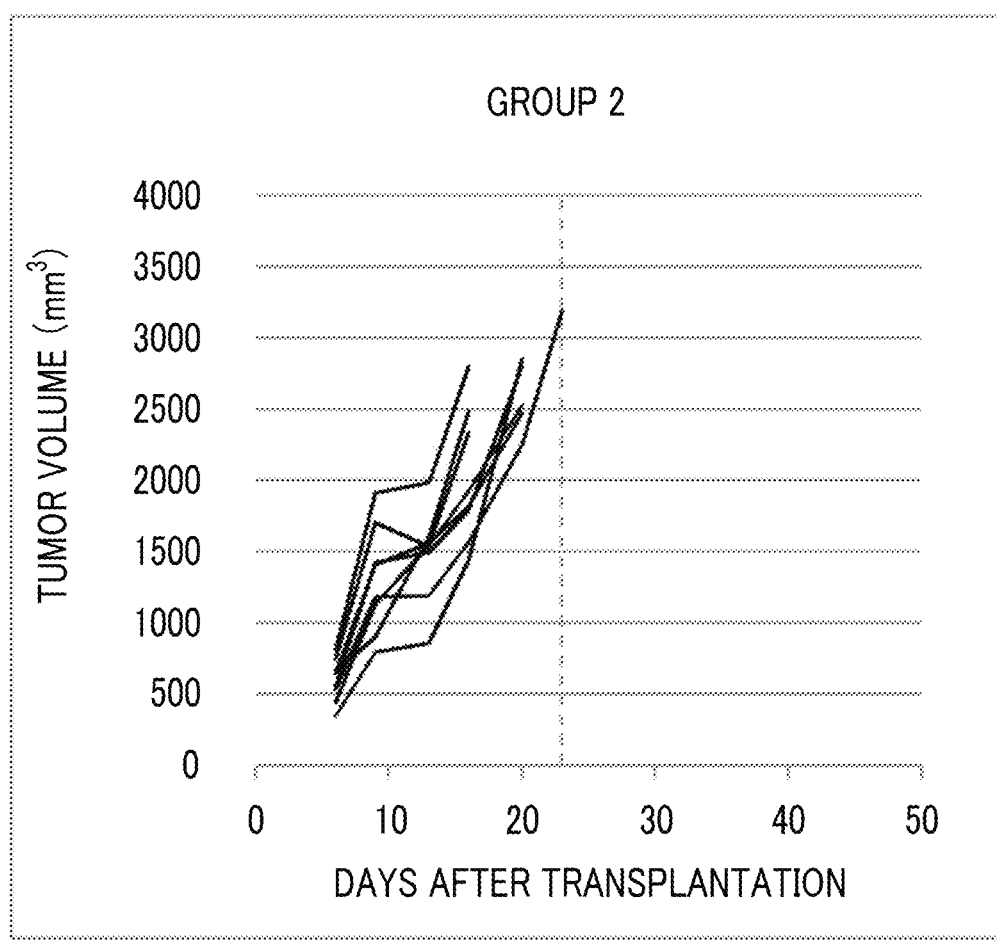
FIG. 4 shows changes in tumor volume by individual in a drug efficacy test using a tumor-bearing model mouse with subcutaneous transplantation of EMT6.
Figure 5:
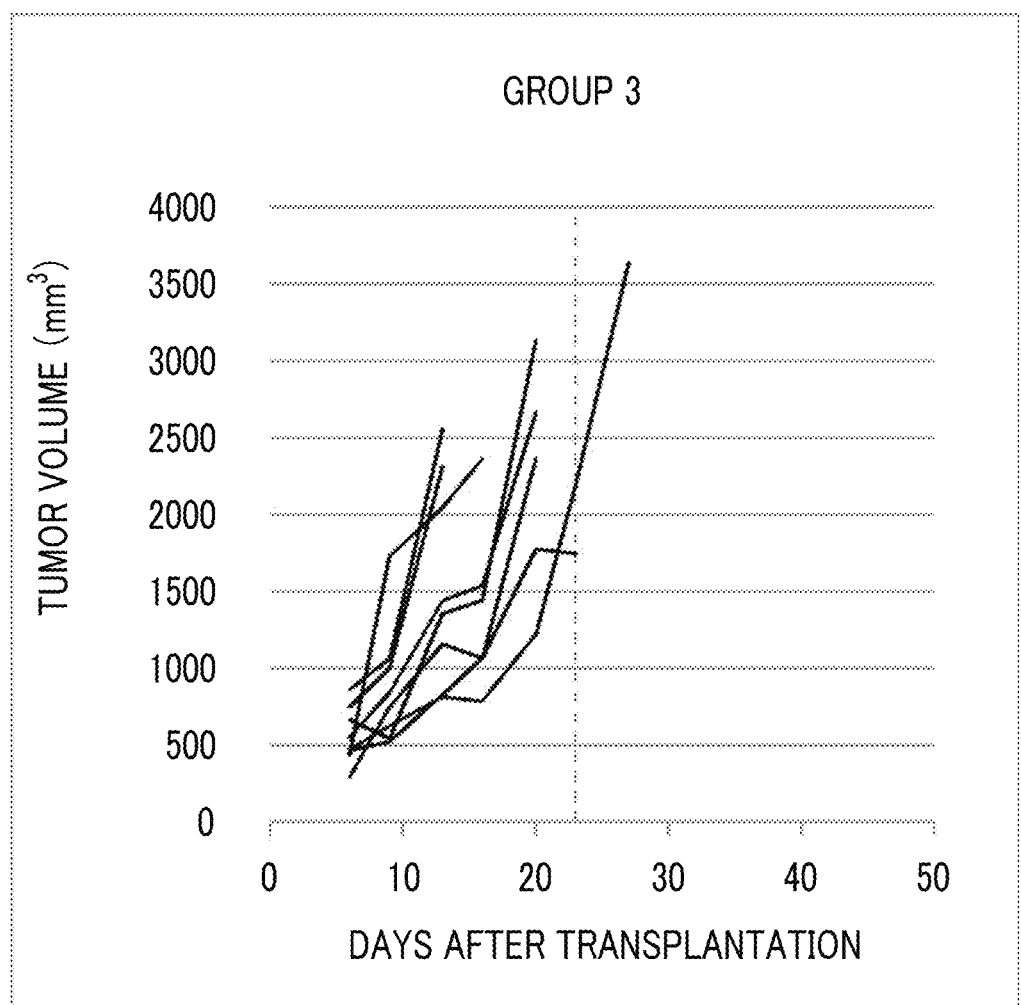
FIG. 5 shows changes in tumor volume by individual in a drug efficacy test using a tumor-bearing model mouse with subcutaneous transplantation of EMT6.
Figure 6:
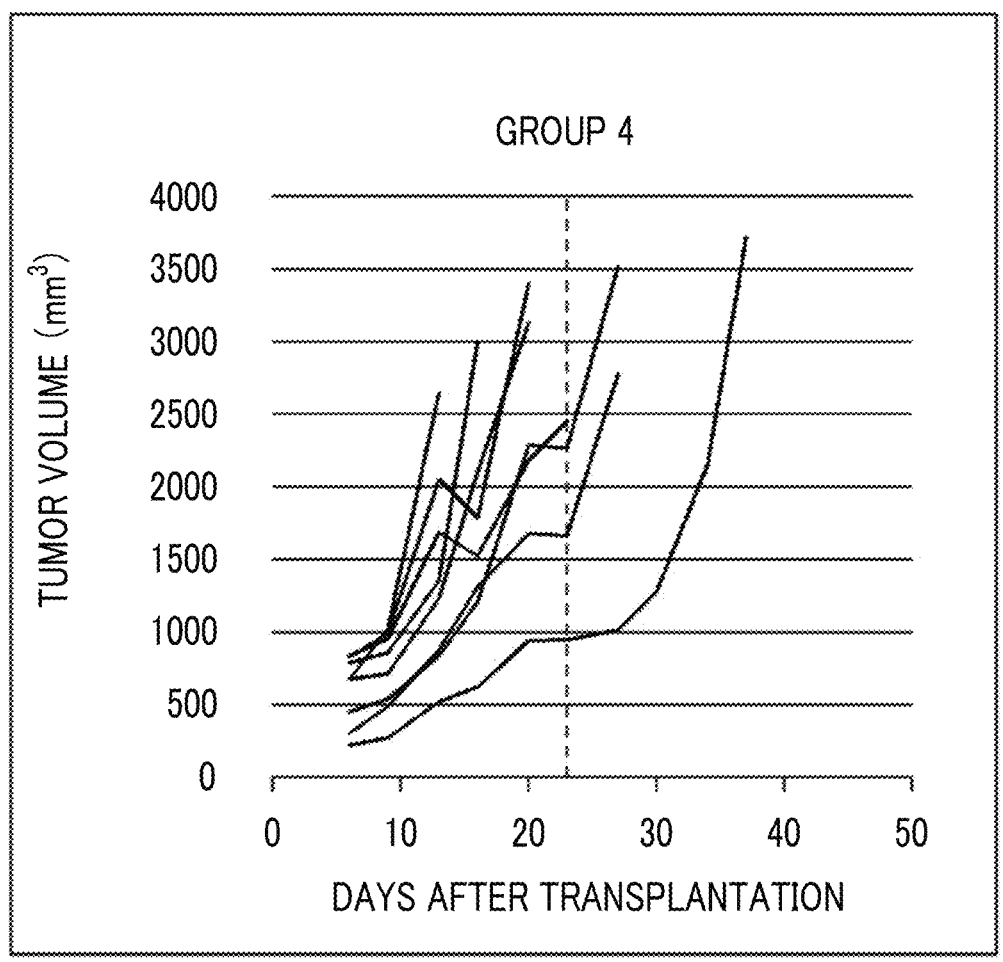
FIG. 6 shows changes in tumor volume by individual in a drug efficacy test using a tumor-bearing model mouse with subcutaneous transplantation of EMT6.
Figure 7:
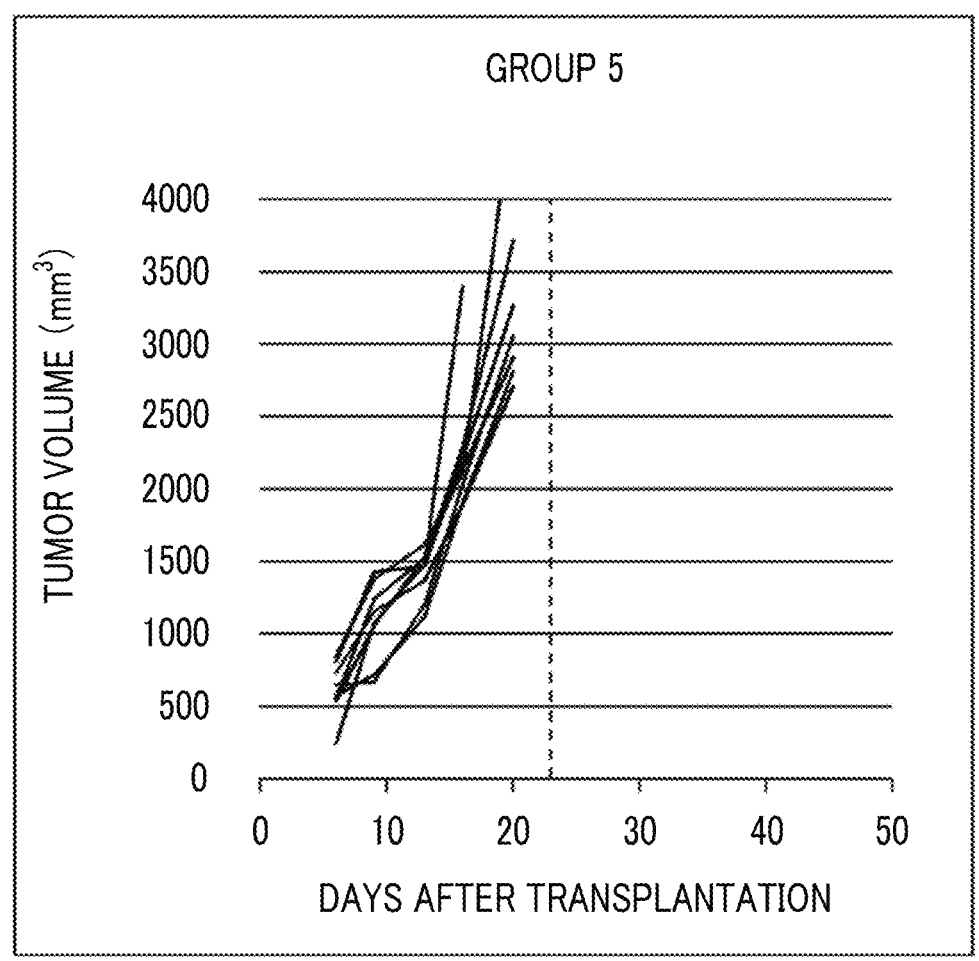
FIG. 7 shows changes in tumor volume by individual in a drug efficacy test using a tumor-bearing model mouse with subcutaneous transplantation of EMT6.
Figure 8:
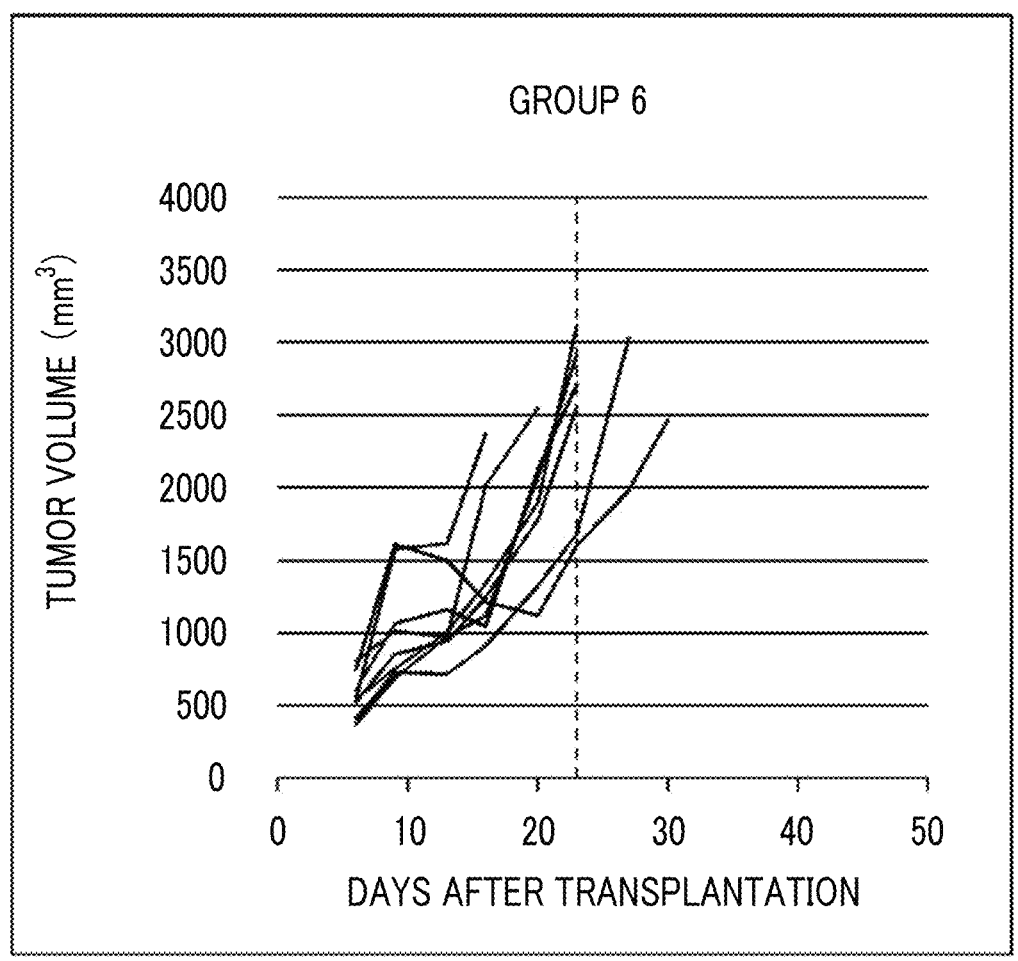
FIG. 8 shows changes in tumor volume by individual in a drug efficacy test using a tumor-bearing model mouse with subcutaneous transplantation of EMT6.
Figure 9:
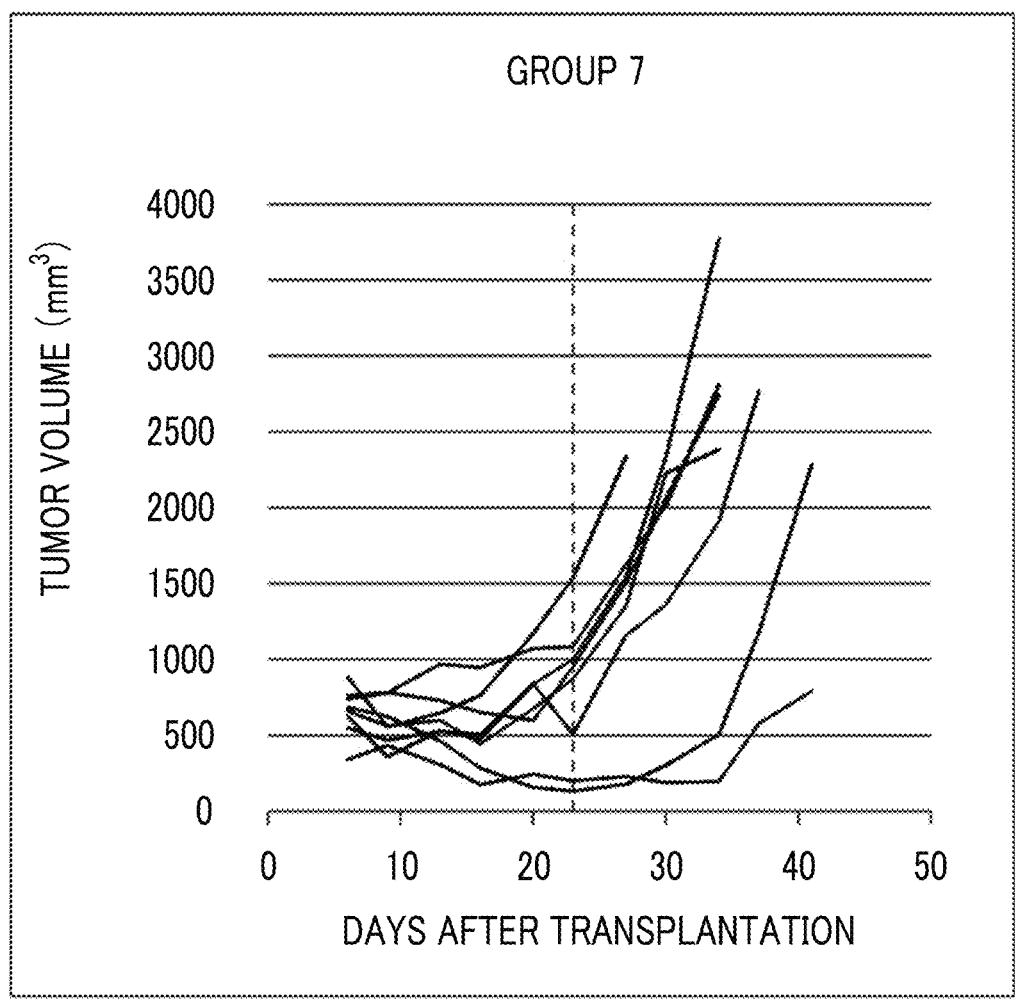
FIG. 9 shows changes in tumor volume by individual in a drug efficacy test using a tumor-bearing model mouse with subcutaneous transplantation of EMT6.
Figure 10:
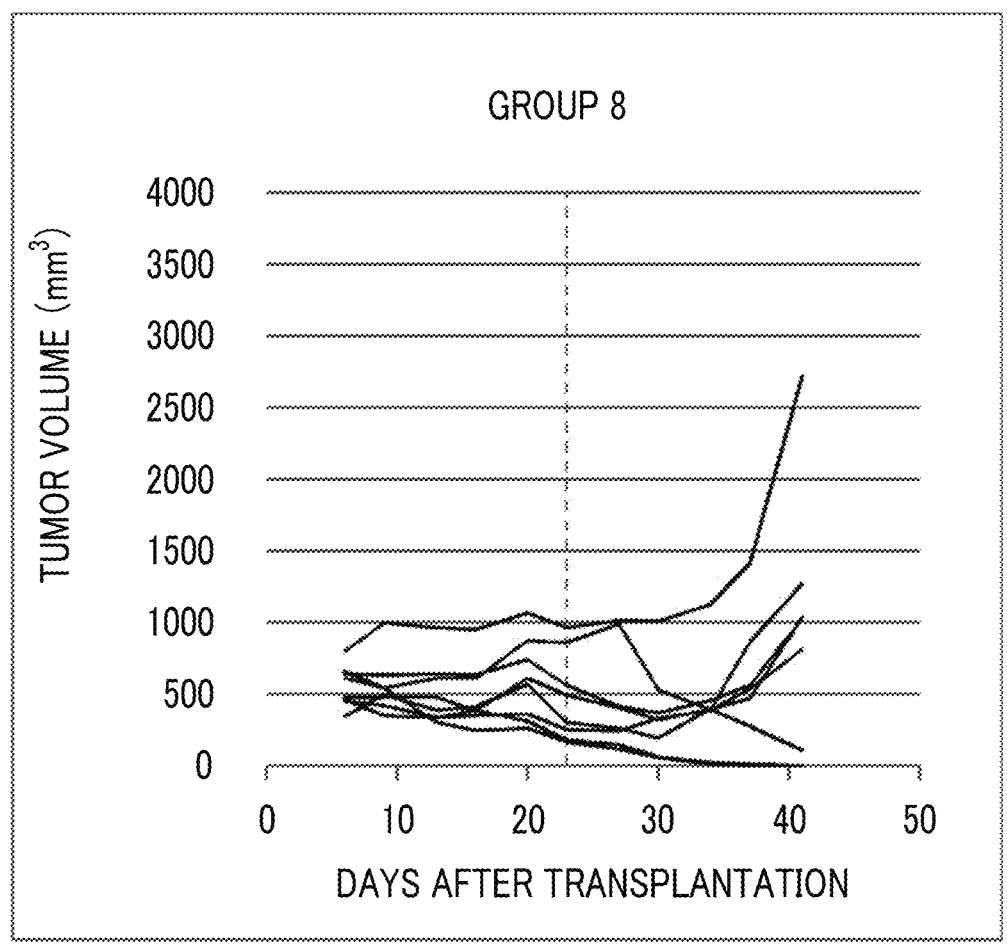
FIG. 10 shows changes in tumor volume by individual in a drug efficacy test using a tumor-bearing model mouse with subcutaneous transplantation of EMT6.

Changes in body weight are shown in FIG. 1. Changes in tumor volume are shown in FIG. 2 (mean value) and FIGS. 3 to 10 (on the basis of an individual). Table 2 shows the number of test subjects in complete remission (test subjects with zero tumor volume) by post-transplantation day 41, the number of test subjects in the group, and the complete remission rate (%).

TABLE 2

| Group | Number of test subjects in complete remission | Number of individuals in group | Complete remission rate (%) |
|---|---|---|---|
| 1 | 0 | 8 | 0 |
| 2 | 0 | 8 | 0 |
| 3 | 0 | 8 | 0 |
| 4 | 0 | 8 | 0 |
| 5 | 0 | 8 | 0 |
| 6 | 0 | 8 | 0 |
| 7 | 0 | 8 | 0 |
| 8 | 2 | 8 | 25 |

In Group 1, Group 2, Group 3, Group 4, Group 5, and Group 6, tumor growth could not be stopped during the dosing period, and all test subjects were subjected to euthanasia by the day of test termination, which is post-transplantation day 41. In Group 7, an excellent growth inhibitory effect was exhibited, but all test subjects were subjected to euthanasia due to re-growth of tumor after cessation of the drug. In Group 8, an excellent growth inhibitory effect was exhibited, a tumor growth inhibitory effect was confirmed even after cessation of the drug, and 2 out of 8 cases were in complete remission.

Figure 11:
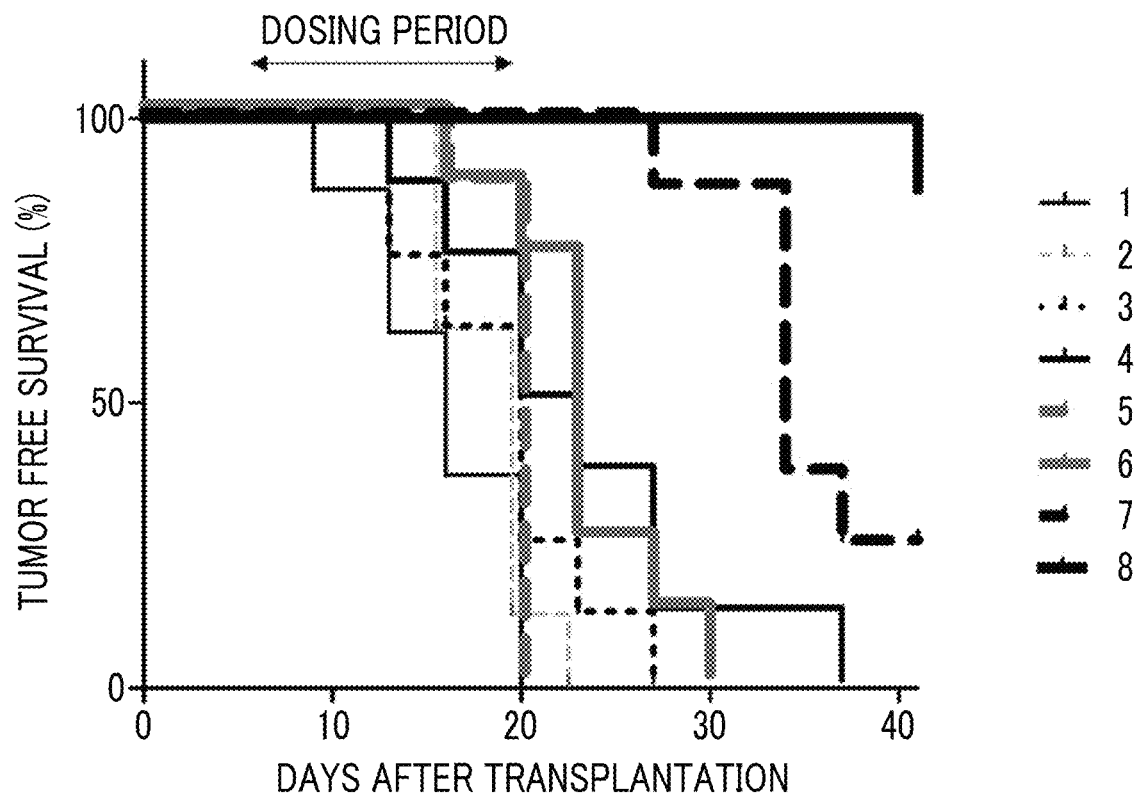
FIG. 11 shows a survival rate (tumor-free survival %) in a case where a test subject having a tumor volume of more than 10% of the body weight is euthanized, and the results of a survival curve by the Kaplan-Meier method.

The survival rate (tumor-free survival %) in a case where a test subject with a tumor volume of more than 10% of body weight was euthanized was calculated, and the results of a survival curve by the Kaplan-Meier method are shown in FIG. 11. In FIG. 11, the numbers represent Group 1 to Group 8. As a statistical analysis of an effect of prolonging the survival time, a log-rank test was carried out, and a p value of less than 5% between the groups was determined to have a statistically significant difference. Graghpad Prism version 5.03 was used for the calculation of median survival calculated from the survival curve by Kaplan-Meier method and the statistical analysis. Table 3 shows the results of analysis of the survival curve by the Kaplan-Meier method.

In the log-rank test of Table 3, "a" indicates $p<0.05$, "b" indicates $p<0.01$, "c" indicates $p<0.0001$, and "ns" indicates no significant difference. "Undefined" indicates that the survival rate did not fall below 50% in the median survival analysis and could not be analyzed.

TABLE 3

|  | Control group | 2 | 3 | 5 | 7 | 4 | 6 | 8 |
|---|---|---|---|---|---|---|---|---|
|  | Comparative group |  | 1 |  |  | 3 | 5 | 7 |
| Log-rank Test | p value | 0.1255 | 0.1562 | 0.0346 | <0.0001 | 0.2223 | 0.0109 | 0.0074 |
|  | Determination | ns | ns | a | c | ns | a | b |
| Median survival | Control group | 20 | 20 | 20 | 34 | 21.5 | 23 | Undefined |
|  | Comparative group | 16 | 16 | 16 | 16 | 20 | 20 | 34 |
|  | Percentage (%) | 1.25 | 1.25 | 1.25 | 2.125 | 1.075 | 1.15 | — |

No significant prolongation of the survival time was observed in Group 2 or Group 3 as compared to Group 1, and PD-L1 or Gem could not exhibit an effect. On the other hand, a statistically significant effect of prolonging the survival time was observed in Group 5 or Group 7 as compared to Group 1. In the verification of the combinational effect, no significant change in effect of prolonging the survival time was confirmed in Group 4 as compared to Group 3, and the effect of prolonging the survival time was significantly enhanced in Group 6 as compared to Group 5. Furthermore, Group 8 exhibited a significant enhancement of the effect of prolonging the survival time as compared to Group 7, and 7 out of 8 cases survived until the day of test termination, which is post-transplantation day 41.

From the above results, it was shown that the liposome composition according to the embodiment of the present invention, in a case of being used in combination with PD-L1, had an excellent growth inhibitory effect on EMT6 tumor cells that are resistant to the effects of Gem or PD-L1, and the growth inhibitory effect was superior to that of the combination of Gem and PD-L1.

Example 2

Drug efficacy test with combined use of PD-1 in tumor-bearing model mouse with subcutaneous transplantation of EMT6

As the test substance, the same substance as in Example 1 was used. $3 \times 10^6$ EMT6 cells, which are a mouse breast cancer cell line, were subcutaneously transplanted into the flank of female Balb mice to form subcutaneous tumors. Using the tumor volume as an index, inhibitory effects of combined administration of PD-1 and Gem and combined administration of PD-1 and Lipo on subcutaneous tumors were evaluated. The test substances PD-1 and a solvent therefor (PBS; phosphate-buffered saline) were intraperitoneally administered twice a week for a total of 3 weeks, and the test substances Gem, the liposome composition according to the embodiment of the present invention, and a solvent therefor (5% Glu) were administered once a week by tail vein administration for a total of 3 weeks. After the 3-week administration was completed, the drug was discontinued, and the tumor volume measurement was continued for 2 weeks.

Group configuration was set to a combination of 5% Glu and PBS for Group 1, a combination of 5% Glu and PD-L1 (10 mg/kg) for Group 2, a combination of Gem (240 mg/kg) and Iso antibody (10 mg/kg) for Group 3, a combination of Gem (240 mg/kg) and PD-1 (10 mg/kg) for Group 4, a combination of Lipo (2 mg/kg) and PBS for Group 5, a combination of Lipo (2 mg/kg) and PD-1 (10 mg/kg) for Group 6, a combination of Lipo (4 mg/kg) and PBS for Group 7, and a combination of Lipo (4 mg/kg) and PD-1 (10 mg/kg) for Group 8. Groups 1 to 5 and 7 are Comparative Examples, and Groups 6 and 8 are Examples. The upper limit of the dose of each drug was set as a dose that does not reach the minimum body weight, assuming that the amount at which the weight loss rate does not exceed 20% is a maximum tolerable dose (MTD). The group configuration and dose are shown in Table 4. In Table 4, "Dose" represents an amount as an active form of gemcitabine, "Twice/3W" represents twice-weekly administration for a total of 3 weeks, "Once/3W" represents once-weekly administration for a total of 3 weeks, "Abdomen" represents intraperitoneal administration, "Tail" represents tail vein administration, and "Lipo" represents the liposome composition according to the embodiment of the present invention. In addition, Lipo (2) and Lipo (4) mean that the liposome composition according to the embodiment of the present invention was administered to a subject at a dose of 2 mg/kg and a dose of 4 mg/kg, respectively.

TABLE 4

| Group | Test substance | Dose (mg/kg/administration) PD-1 | Dose (mg/kg/administration) Gemcitabine | PD-L1 and PBS Administration route | PD-L1 and PBS Administration schedule | Gem, Lipo, and 5% Glu Administration route | Gem, Lipo, and 5% Glu Administration schedule | Dosage (mL/kg) |
|---|---|---|---|---|---|---|---|---|
| 1 | 5% Glu + PBS | 0 | 0 | Abdomen | Twice/3W | Tail | Once/3W | 10 |
| 2 | 5% Glu + PD-1 | 10 | 0 | Abdomen | Twice/3W | Tail | Once/3W | 10 |
| 3 | Gem + PBS | 0 | 240 | Abdomen | Twice/3W | Tail | Once/3W | 10 |
| 4 | Gem + PD-1 | 10 | 240 | Abdomen | Twice/3W | Tail | Once/3W | 10 |
| 5 | Lipo (2) + PBS | 0 | 2 | Abdomen | Twice/3W | Tail | Once/3W | 10 |
| 6 | Lipo (2) + PD-1 | 10 | 2 | Abdomen | Twice/3W | Tail | Once/3W | 10 |
| 7 | Lipo (4) + PBS | 0 | 4 | Abdomen | Twice/3W | Tail | Once/3W | 10 |
| 8 | Lipo (4) + PD1 | 10 | 4 | Abdomen | Twice/3W | Tail | Once/3W | 10 |

Figure 12:
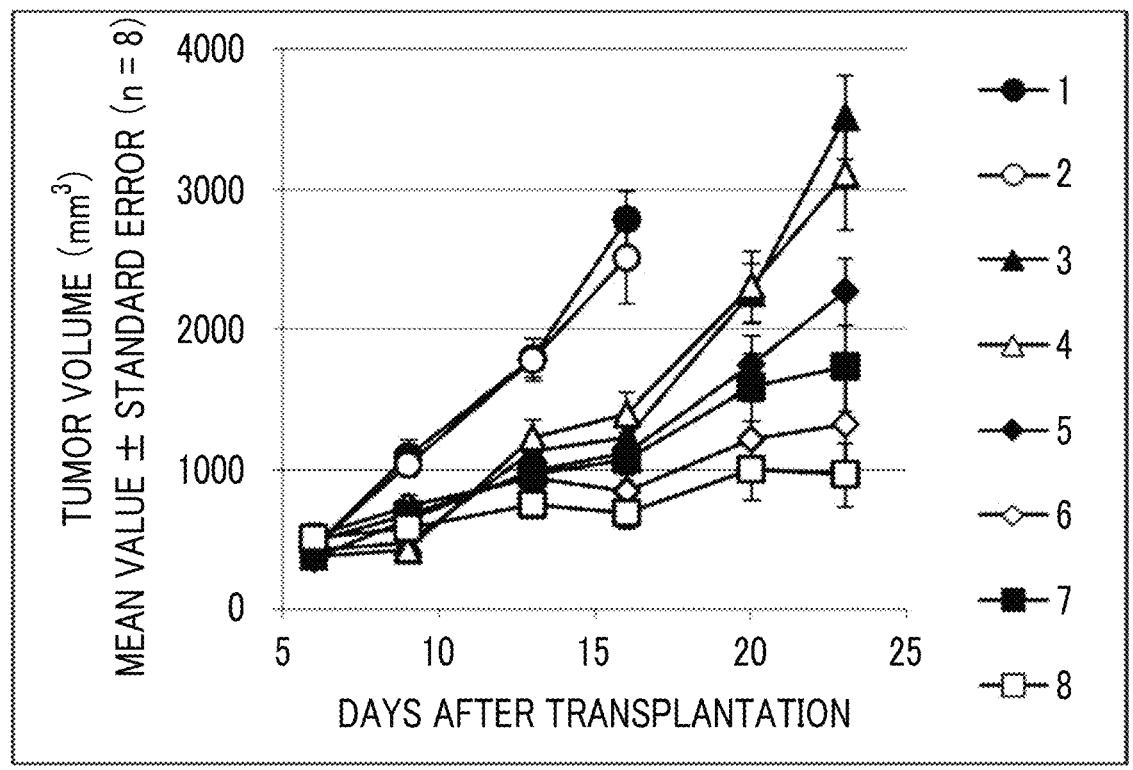
FIG. 12 shows changes in tumor volume in a drug efficacy test using a tumor-bearing model mouse with subcutaneous transplantation of EMT6.
Figure 13:
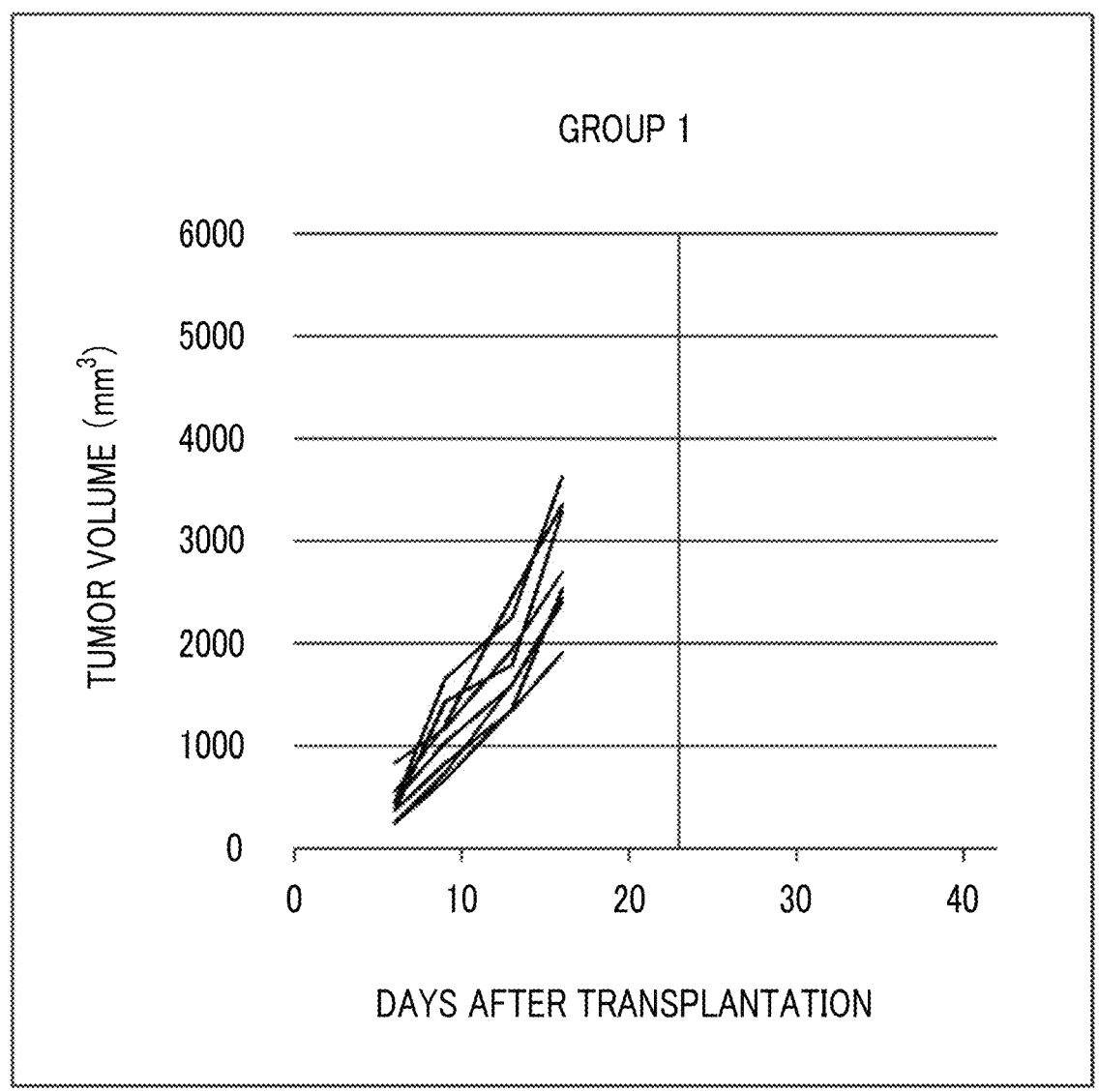
FIG. 13 shows changes in tumor volume by individual in a drug efficacy test using a tumor-bearing model mouse with subcutaneous transplantation of EMT6.
Figure 14:
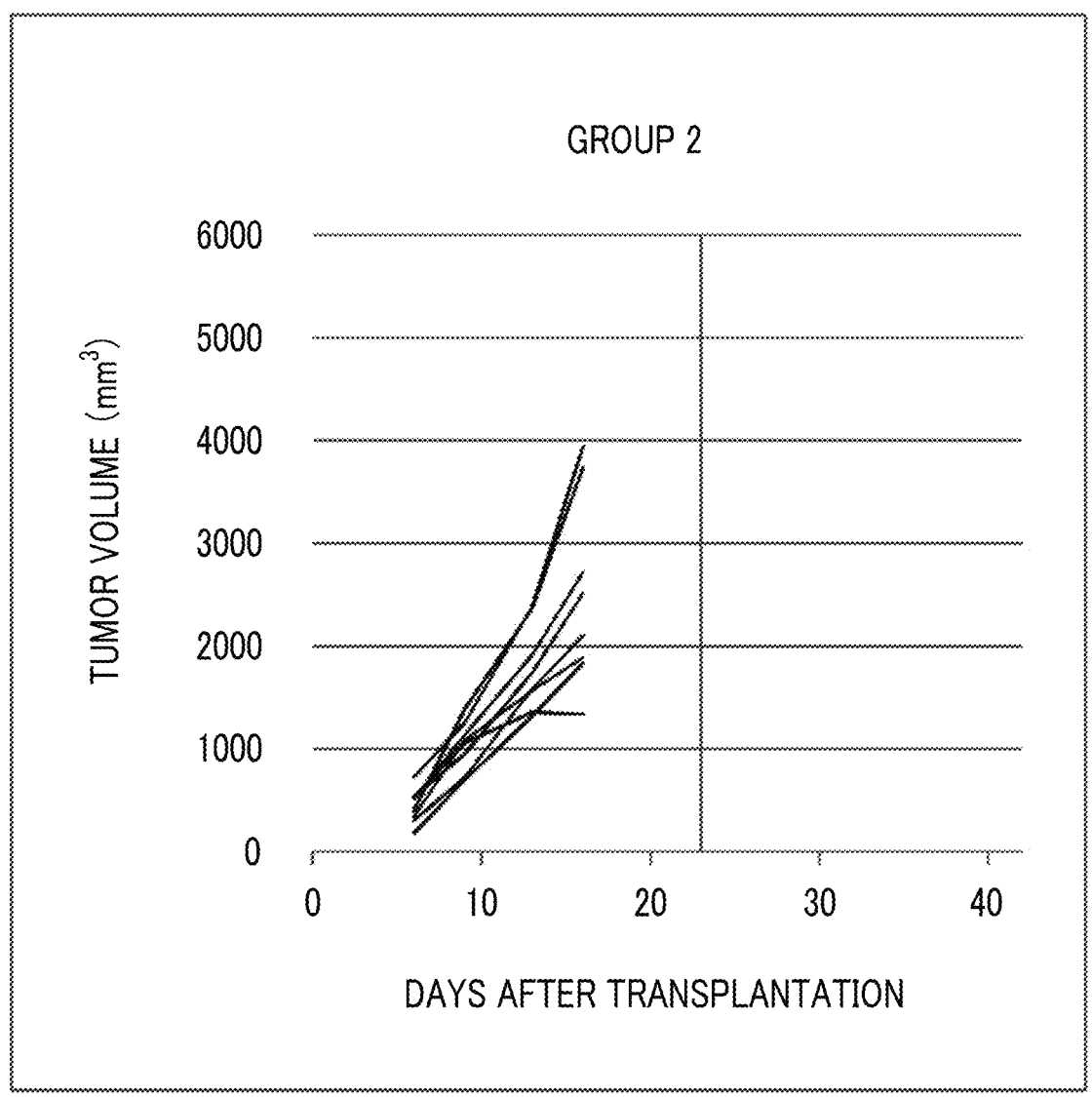
FIG. 14 shows changes in tumor volume by individual in a drug efficacy test using a tumor-bearing model mouse with subcutaneous transplantation of EMT6.
Figure 15:
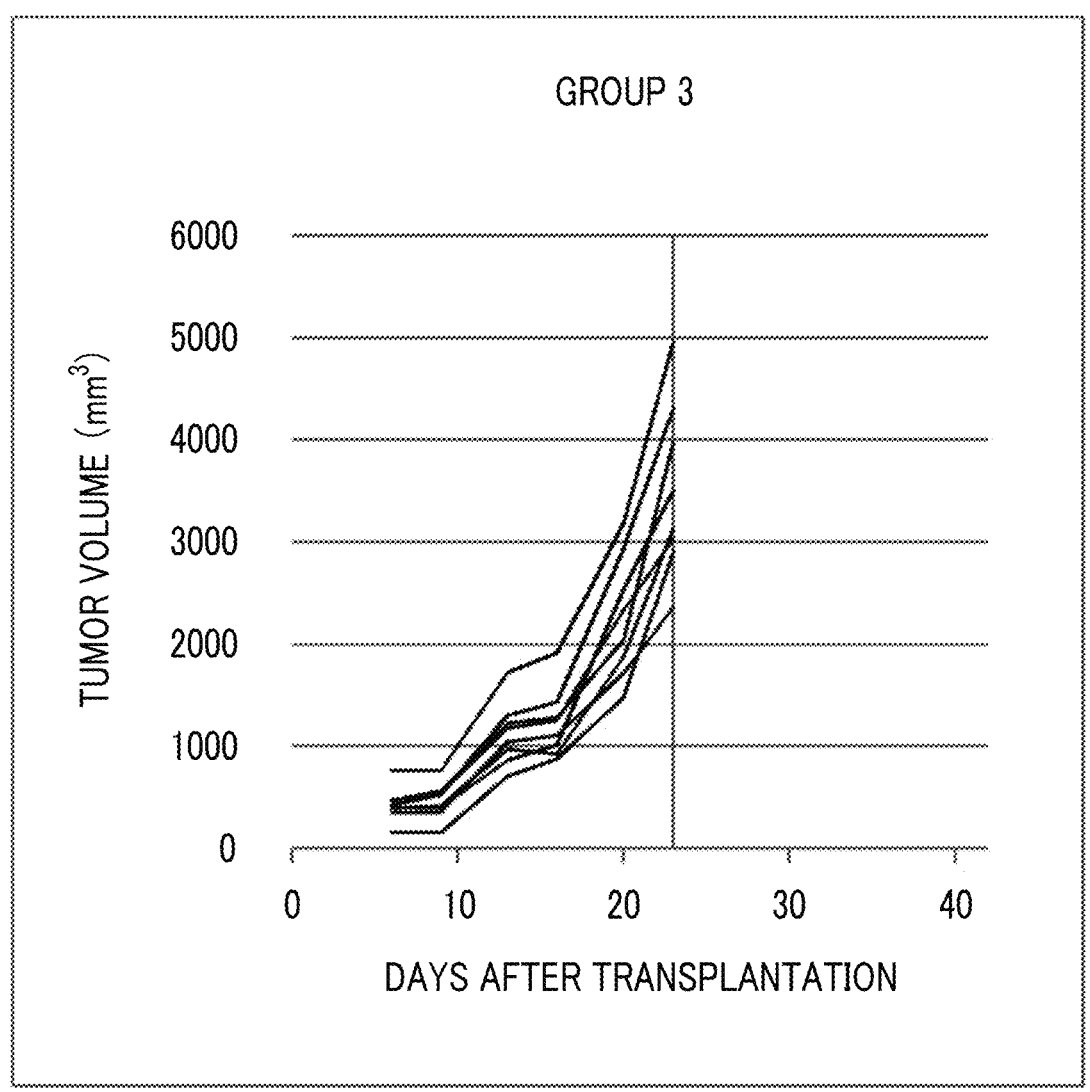
FIG. 15 shows changes in tumor volume by individual in a drug efficacy test using a tumor-bearing model mouse with subcutaneous transplantation of EMT6.
Figure 16:
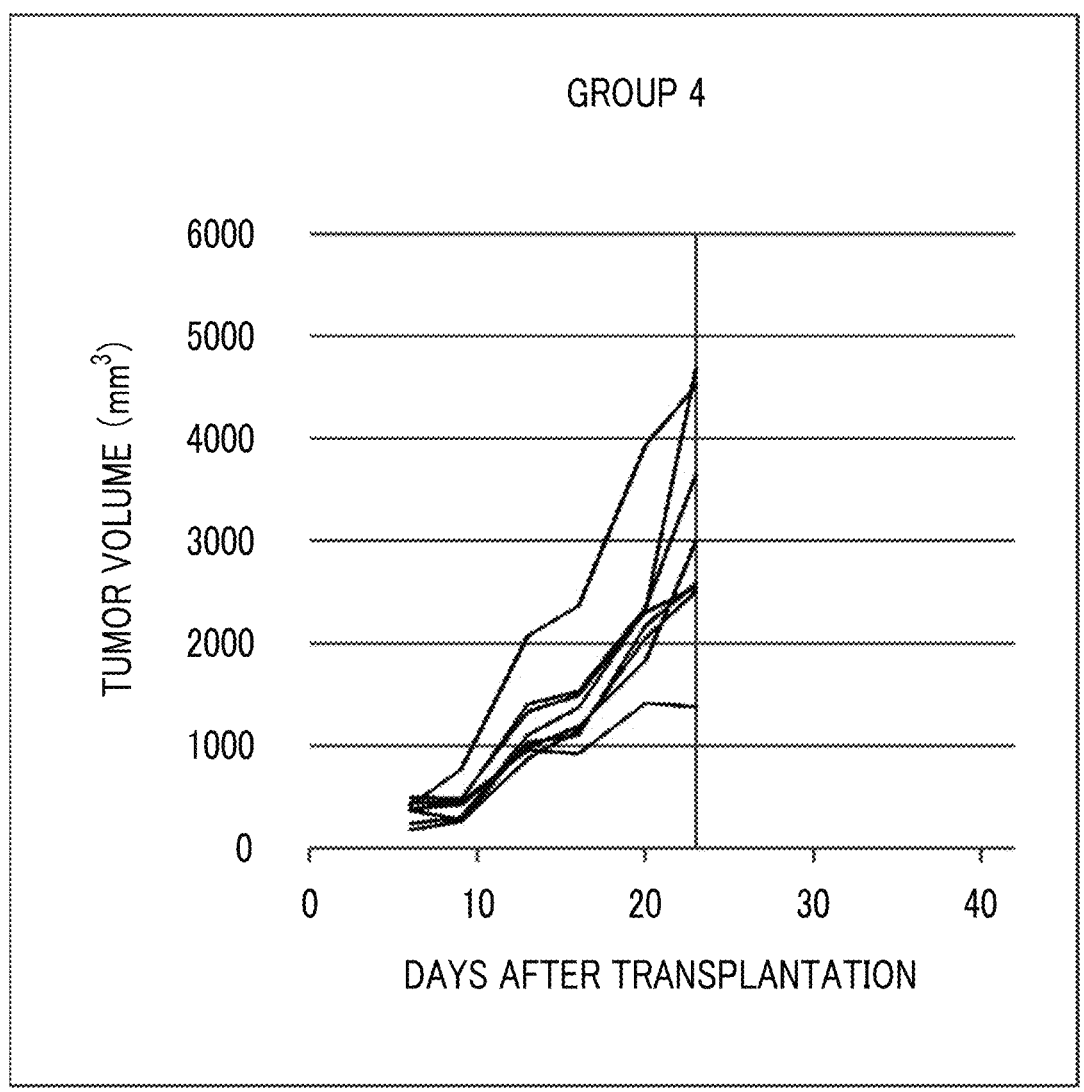
FIG. 16 shows changes in tumor volume by individual in a drug efficacy test using a tumor-bearing model mouse with subcutaneous transplantation of EMT6.
Figure 17:
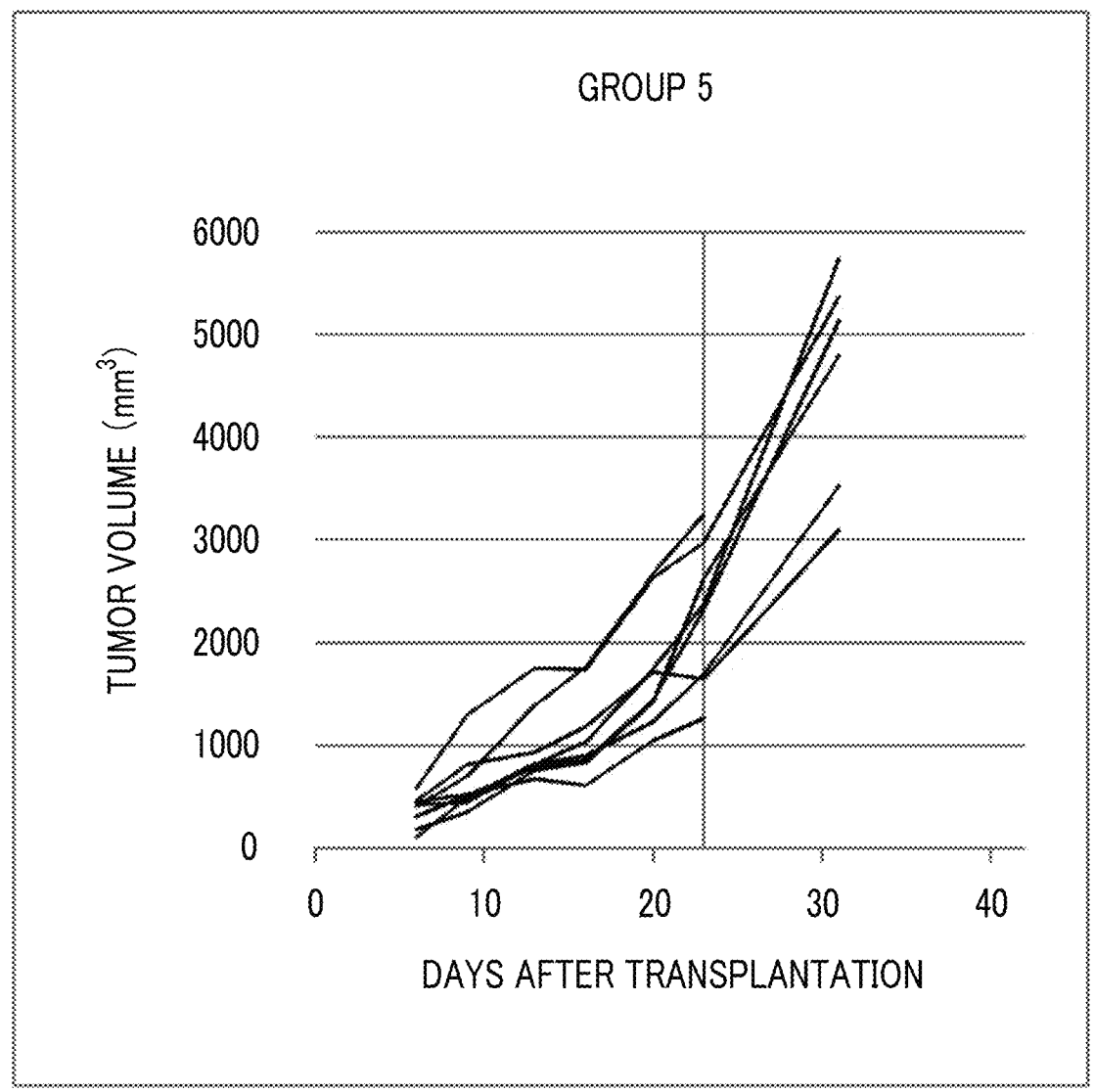
FIG. 17 shows changes in tumor volume by individual in a drug efficacy test using a tumor-bearing model mouse with subcutaneous transplantation of EMT6.
Figure 18:
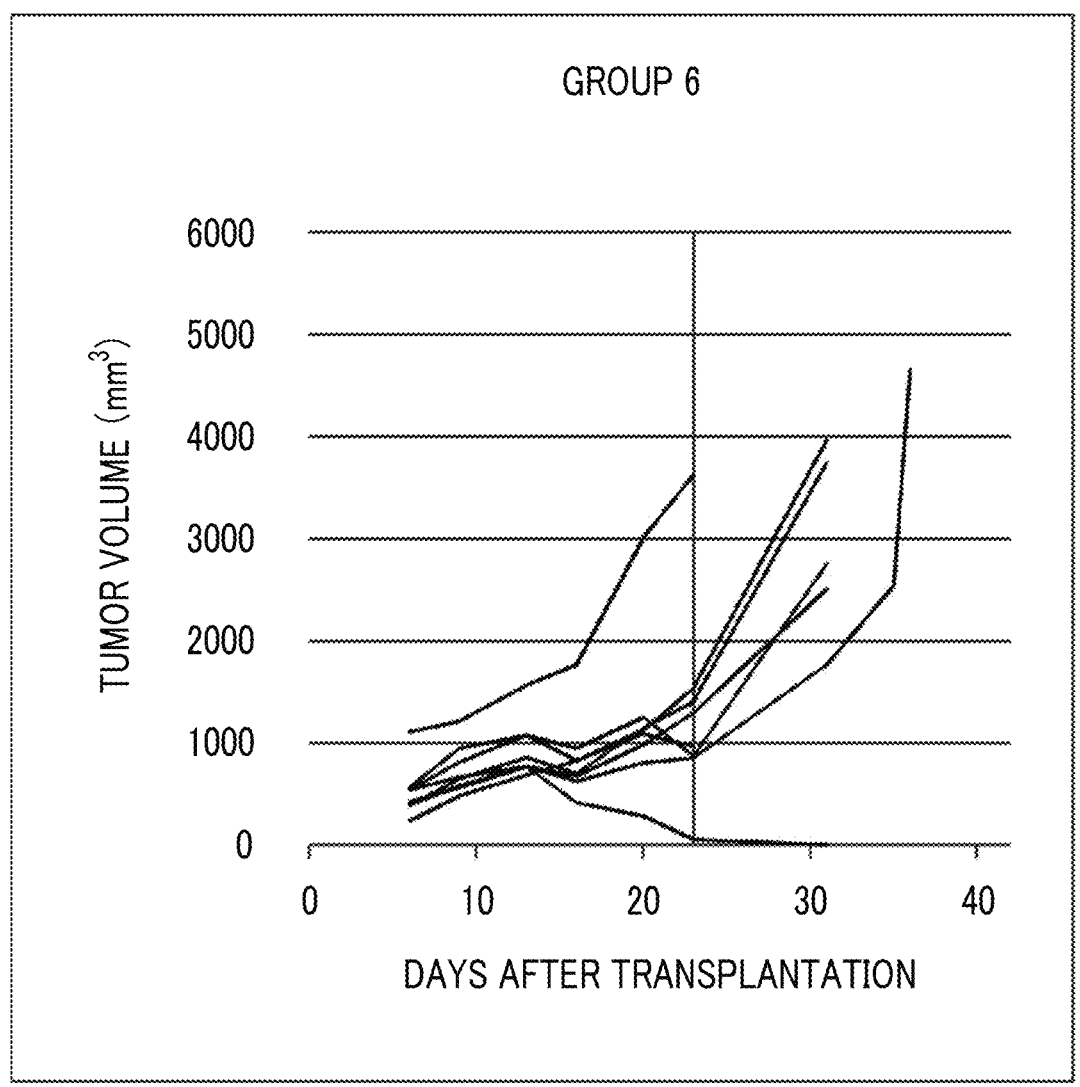
FIG. 18 shows changes in tumor volume by individual in a drug efficacy test using a tumor-bearing model mouse with subcutaneous transplantation of EMT6.
Figure 19:
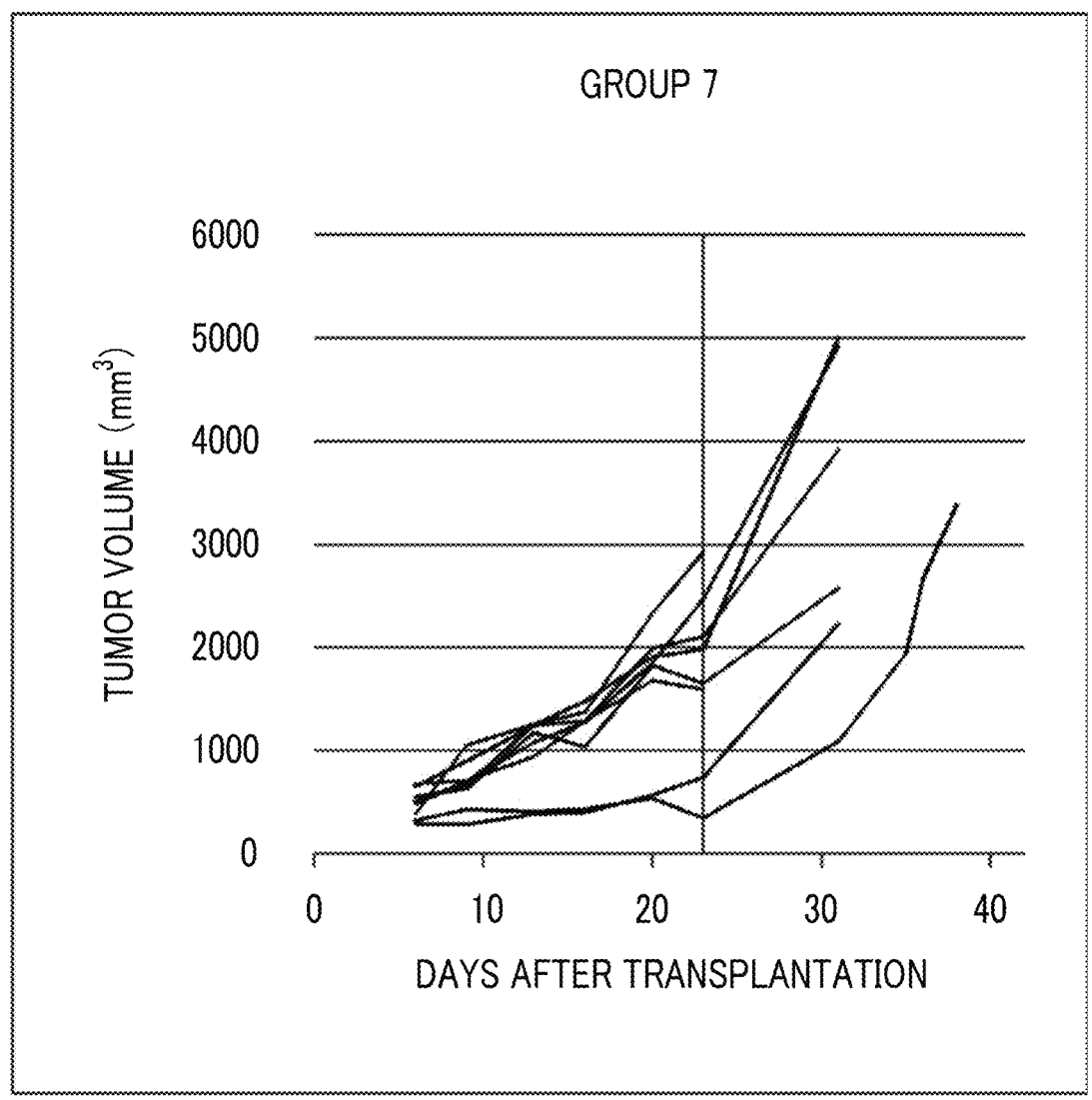
FIG. 19 shows changes in tumor volume by individual in a drug efficacy test using a tumor-bearing model mouse with subcutaneous transplantation of EMT6.
Figure 20:
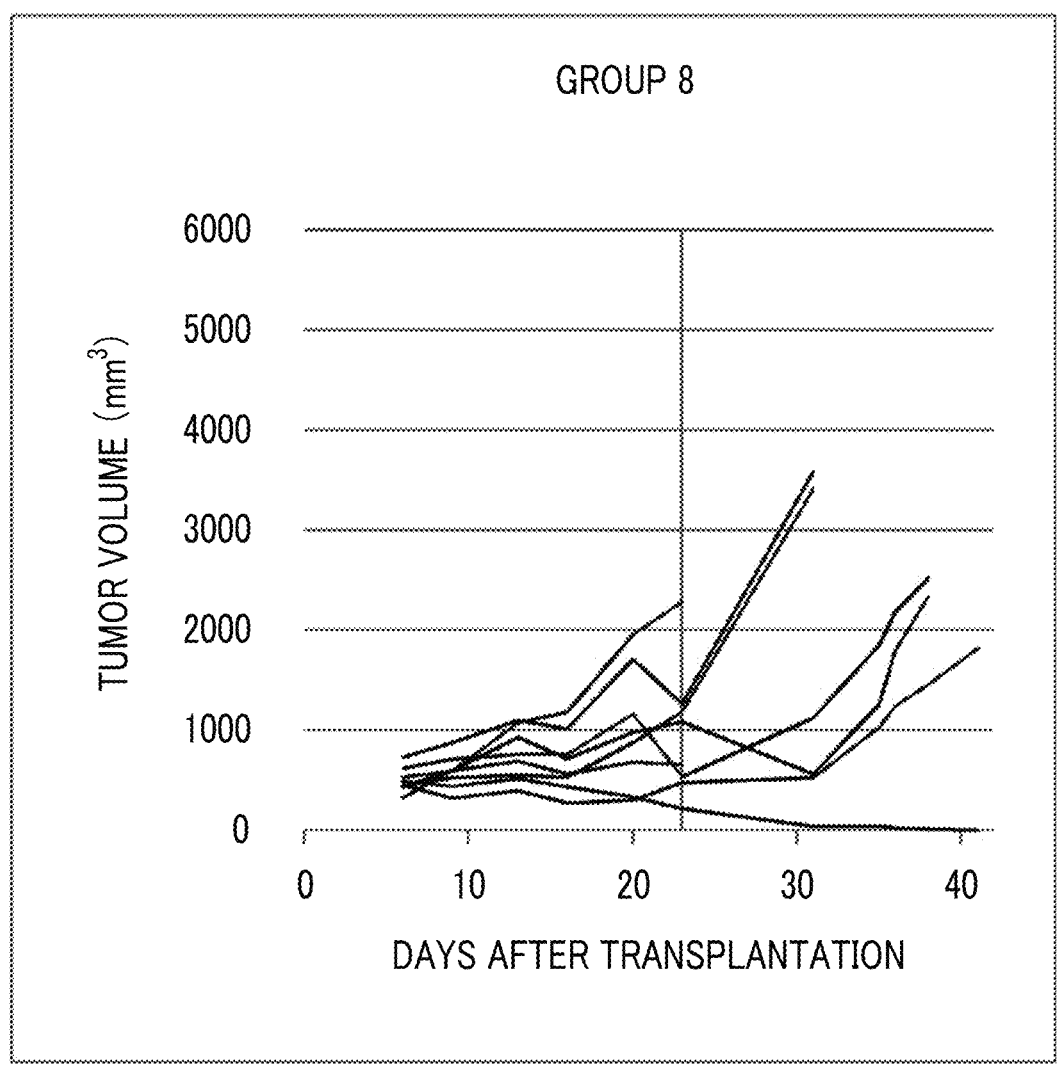
FIG. 20 shows changes in tumor volume by individual in a drug efficacy test using a tumor-bearing model mouse with subcutaneous transplantation of EMT6.
Figure 21:
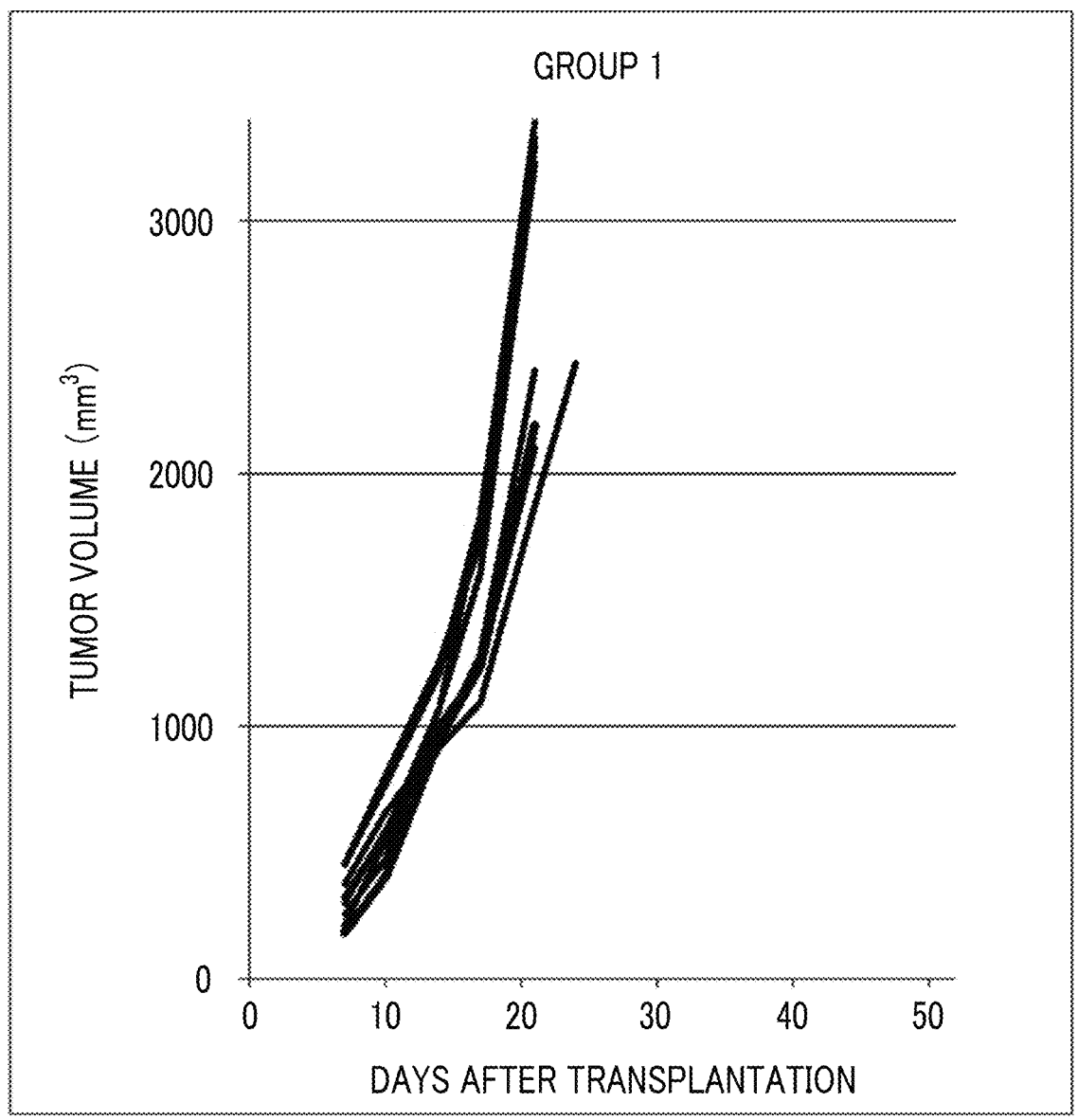
FIG. 21 shows changes in tumor volume by individual in a drug efficacy test using a tumor-bearing model mouse with subcutaneous transplantation of EMT6.
Figure 22:
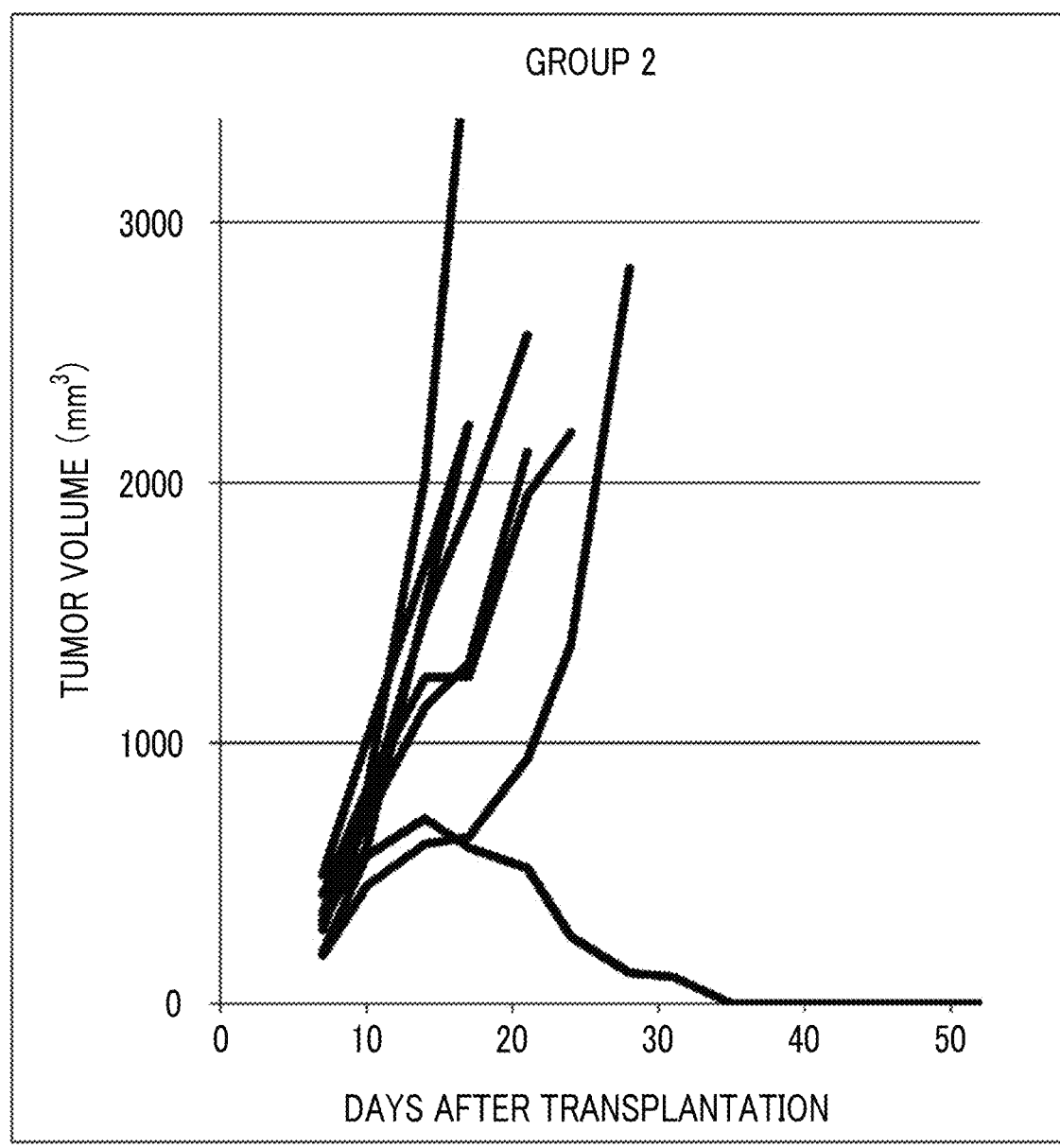
FIG. 22 shows changes in tumor volume by individual in a drug efficacy test using a tumor-bearing model mouse with subcutaneous transplantation of EMT6.
Figure 23:
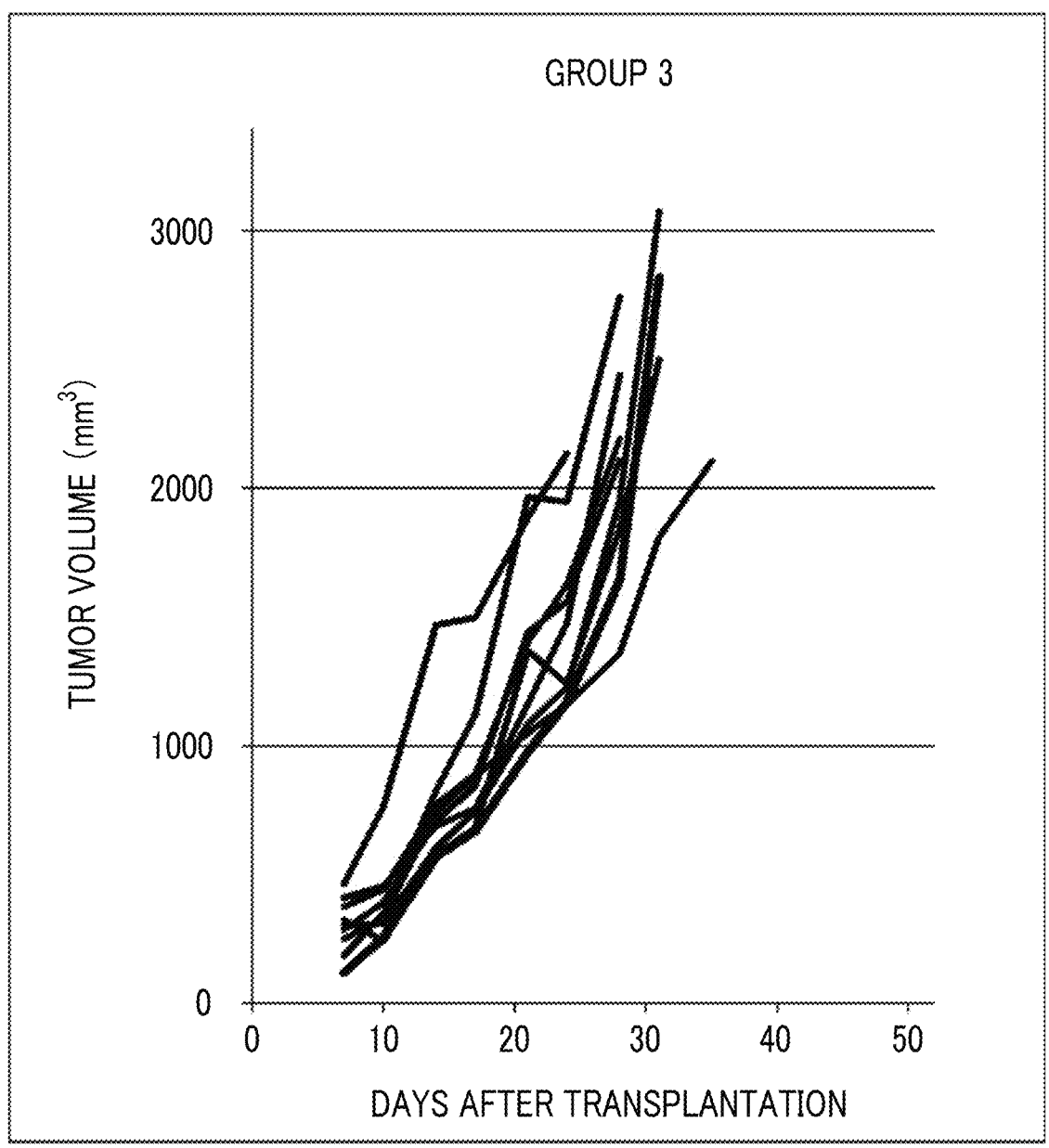
FIG. 23 shows changes in tumor volume by individual in a drug efficacy test using a tumor-bearing model mouse with subcutaneous transplantation of EMT6.
Figure 24:
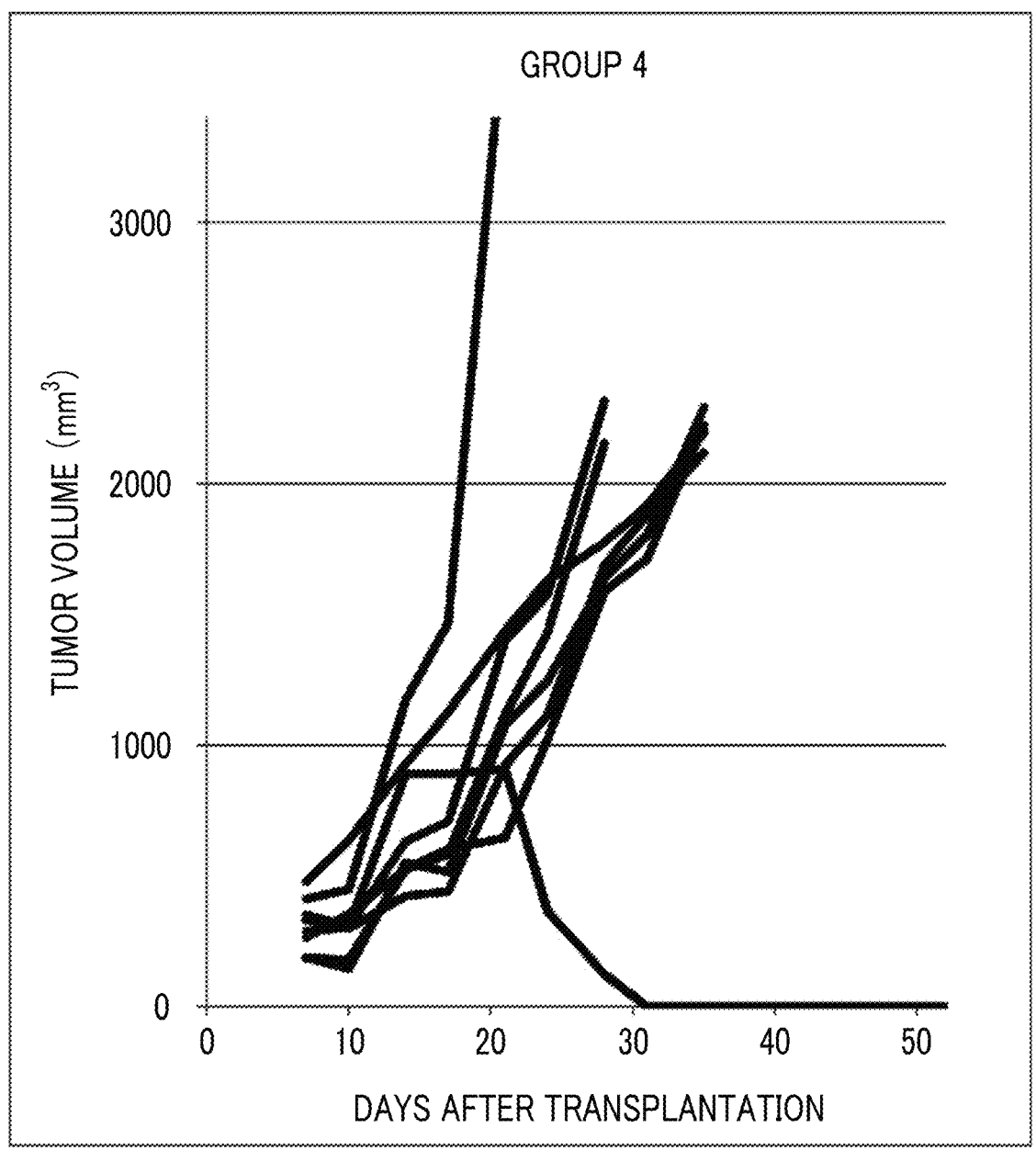
FIG. 24 shows changes in tumor volume by individual in a drug efficacy test using a tumor-bearing model mouse with subcutaneous transplantation of EMT6.
Figure 25:
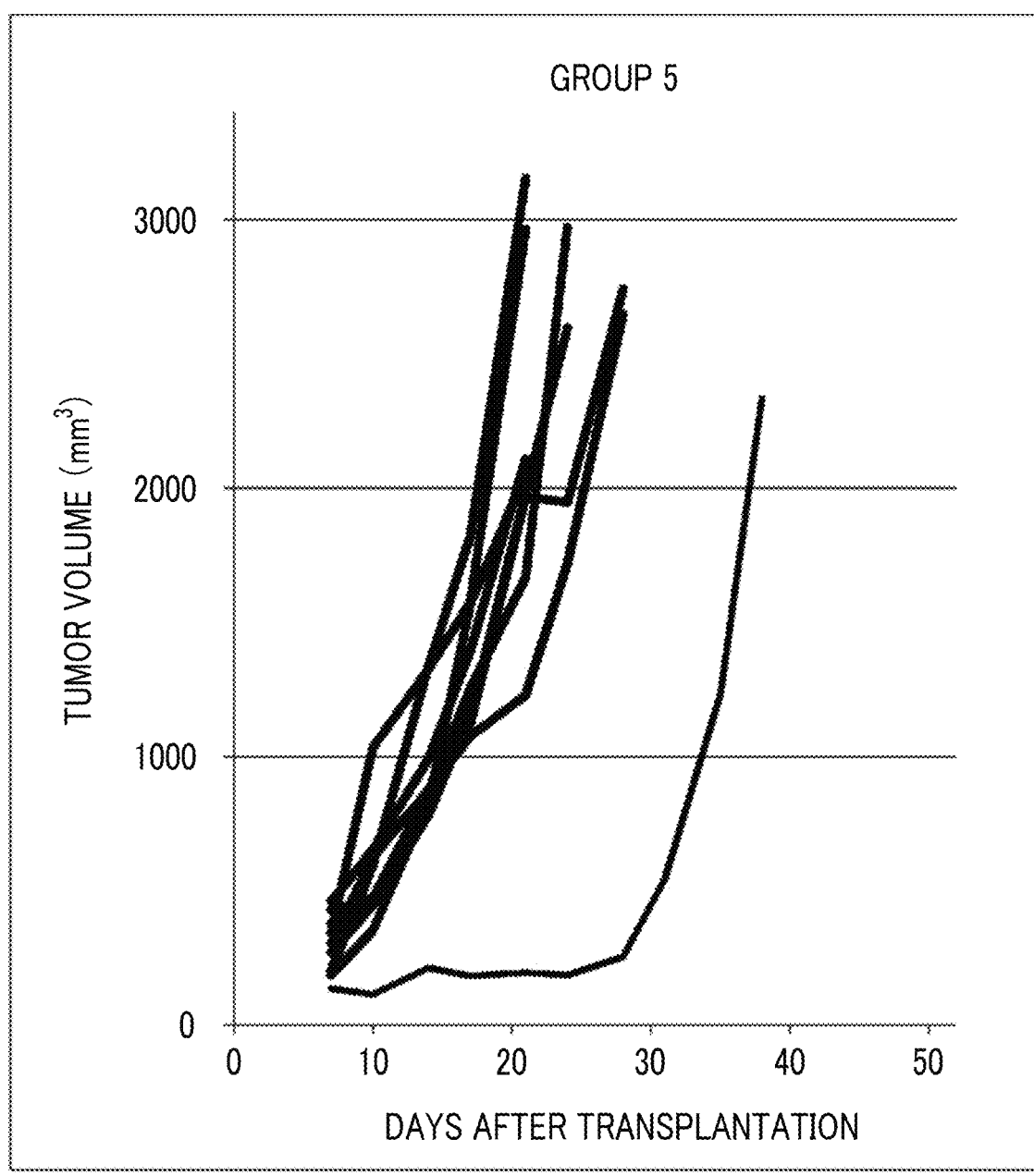
FIG. 25 shows changes in tumor volume by individual in a drug efficacy test using a tumor-bearing model mouse with subcutaneous transplantation of EMT6.
Figure 26:
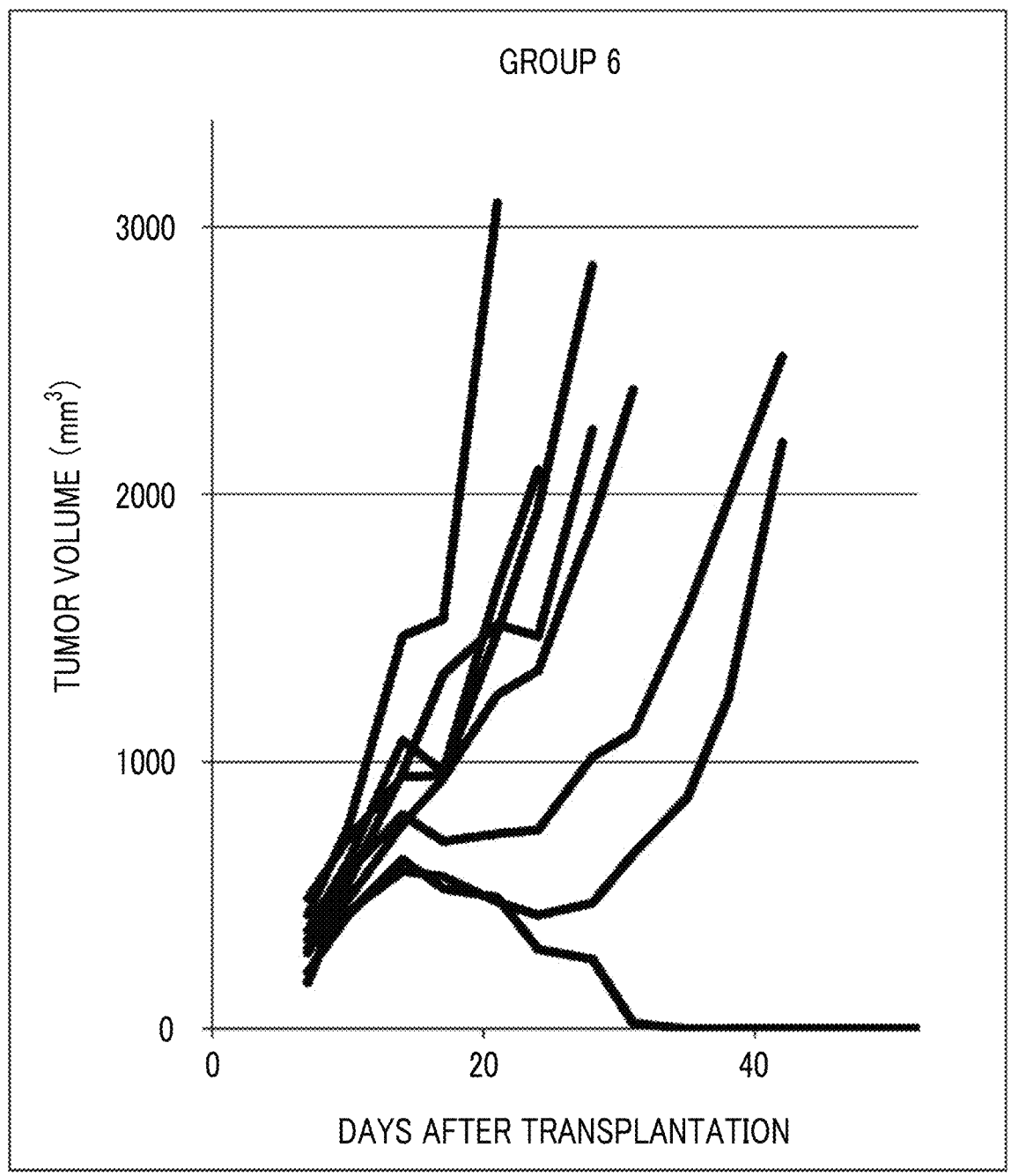
FIG. 26 shows changes in tumor volume by individual in a drug efficacy test using a tumor-bearing model mouse with subcutaneous transplantation of EMT6.
Figure 27:
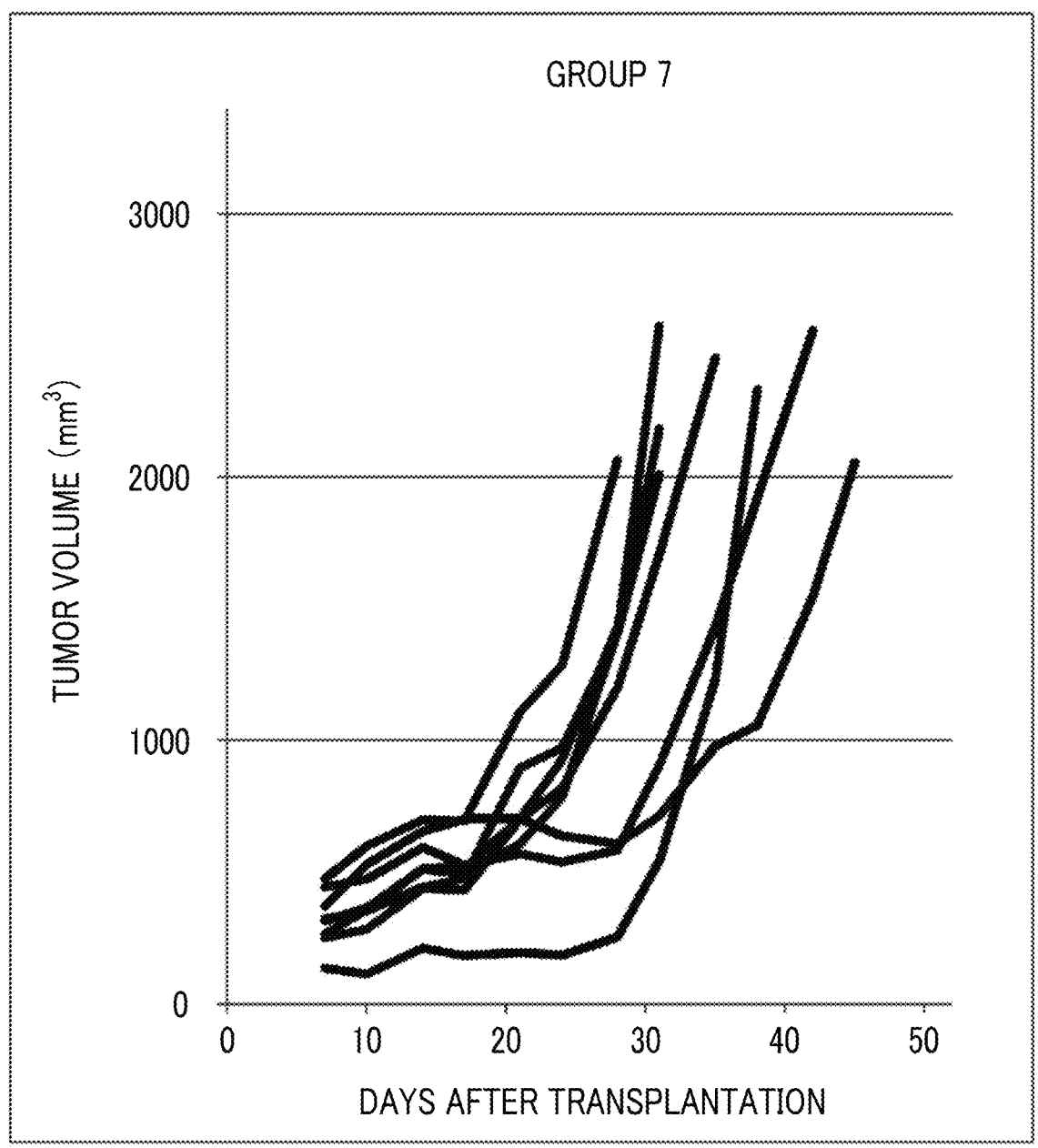
FIG. 27 shows changes in tumor volume by individual in a drug efficacy test using a tumor-bearing model mouse with subcutaneous transplantation of EMT6.
Figure 28:
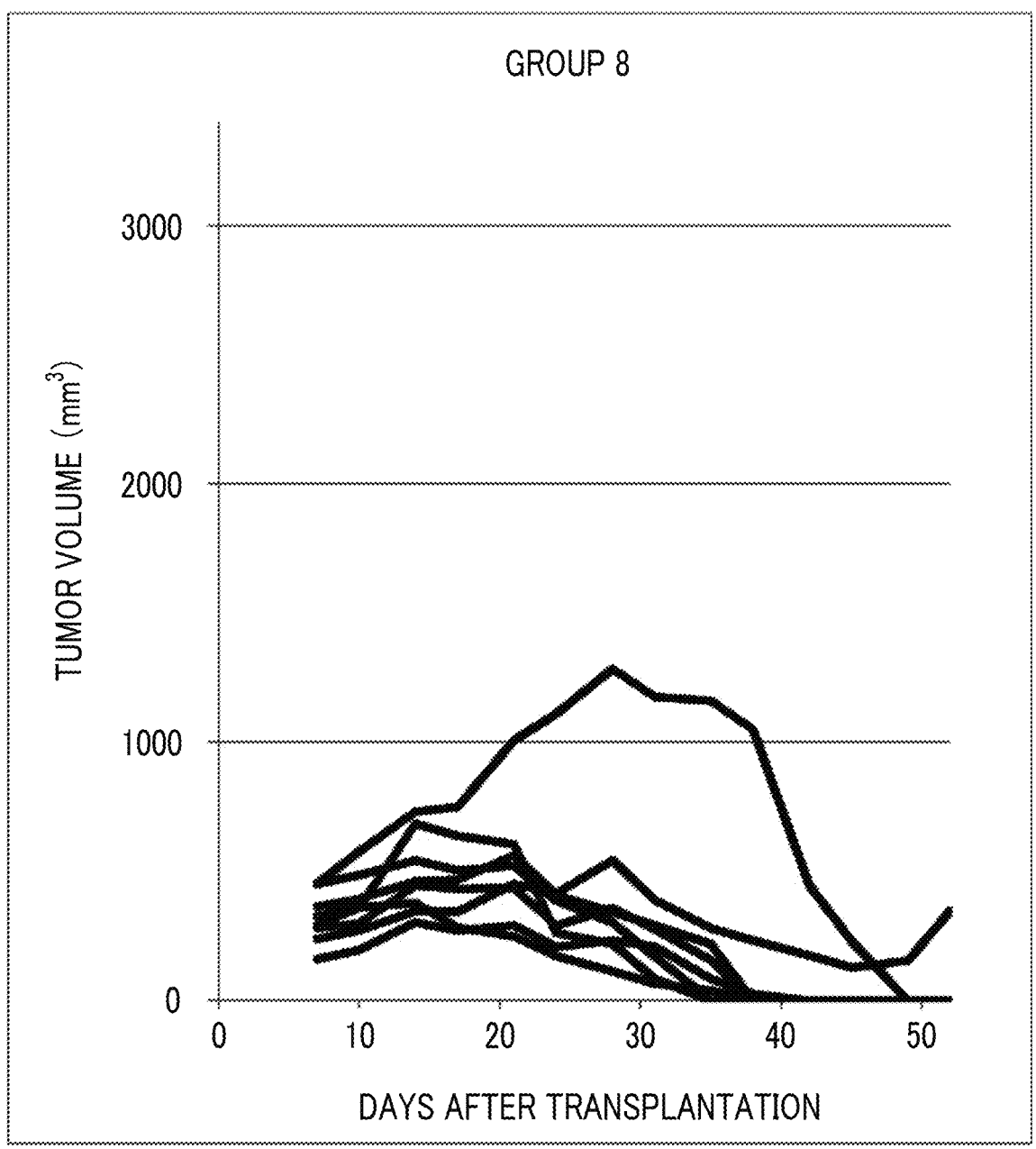
FIG. 28 shows changes in tumor volume by individual in a drug efficacy test using a tumor-bearing model mouse with subcutaneous transplantation of EMT6.

Changes in tumor volume are shown in FIG. 12 (mean value) and FIGS. 13 to 20 (on the basis of an individual). Table 5 shows the number of test subjects in complete remission (test subjects with zero tumor volume) by post-transplantation day 41, the number of test subjects in the group, the complete remission rate (%), and the mean tumor volume on each day after transplantation, and Table 6 shows the tumor volume standard error on each day after transplantation. In Table 5 and Table 6, "Number of test subjects in complete remission" means that the tumor volume was zero. As a statistical analysis of the combinational effect, a Bonferroni multiple comparisons test was carried out, and a p value of less than 5% between the groups with respect to the number of days after transplantation was determined to have a statistically significant difference. Graghpad Prism version 5.03 was used for data processing.

TABLE 5

| Group | Number of test subjects in complete remission | Number of individuals in group | Complete remission rate (%) | Tumor volume mean value ($mm^3$) Days after transplantation 6 | 9 | 13 | 16 | 20 | 23 |
|---|---|---|---|---|---|---|---|---|---|
| 1 | 0 | 8 | 0 | 445 | 1095 | 1798 | 2781 | — | — |
| 2 | 0 | 8 | 0 | 446 | 1040 | 1784 | 2514 | — | — |
| 3 | 0 | 8 | 0 | 432 | 473 | 1129 | 1228 | 2265 | 3521 |
| 4 | 0 | 8 | 0 | 375 | 432 | 1227 | 1395 | 2305 | 3112 |
| 5 | 0 | 8 | 0 | 365 | 644 | 991 | 1117 | 1743 | 2271 |
| 6 | 1 | 8 | 12.5 | 524 | 739 | 946 | 849 | 1212 | 1327 |
| 7 | 0 | 8 | 0 | 486 | 672 | 969 | 1074 | 1590 | 1728 |
| 8 | 1 | 8 | 12.5 | 504 | 582 | 753 | 684 | 1000 | 963 |

TABLE 6

| Group | Number of test subjects in complete remission | Number of individuals in group | Complete remission rate (%) | Tumor volume standard error (±$mm^3$) Days after transplantation 6 | 9 | 13 | 16 | 20 | 23 |
|---|---|---|---|---|---|---|---|---|---|
| 1 | 0 | 8 | 0 | 67 | 121 | 143 | 206 | — | — |
| 2 | 0 | 8 | 0 | 61 | 85 | 147 | 327 | — | — |
| 3 | 0 | 8 | 0 | 60 | 63 | 110 | 119 | 210 | 299 |
| 4 | 0 | 8 | 0 | 38 | 58 | 139 | 157 | 258 | 393 |
| 5 | 0 | 8 | 0 | 56 | 107 | 134 | 151 | 215 | 243 |
| 6 | 1 | 8 | 12.5 | 92 | 85 | 102 | 143 | 278 | 365 |
| 7 | 0 | 8 | 0 | 51 | 85 | 130 | 149 | 235 | 302 |
| 8 | 1 | 8 | 12.5 | 44 | 59 | 93 | 106 | 211 | 230 |

In Table 7, "a" indicates p<0.05, "b" indicates p<0.0001, and "ns" indicates no significant difference.

TABLE 7

| Control group | 4 | | 6 | | 8 | |
|---|---|---|---|---|---|---|
| Comparative group | 3 | | 5 | | 7 | |
| Days after transplantation | p value range | Determination | p value range | Determination | p value range | Determination |
| 6 | p > 0.05 | ns | p > 0.05 | ns | p > 0.05 | ns |
| 9 | p > 0.05 | ns | p > 0.05 | ns | p > 0.05 | ns |
| 13 | p > 0.05 | ns | p > 0.05 | ns | p > 0.05 | ns |
| 16 | p > 0.05 | ns | p > 0.05 | ns | p > 0.05 | ns |
| 20 | p > 0.05 | ns | p <0.05 | a | p > 0.05 | ns |
| 23 | p > 0.05 | ns | p <0.0001 | b | p < 0.05 | a |

In Group 1, Group 2, Group 3, Group 4, and Group 5, tumor growth could not be stopped during the dosing period, and all animals were subjected to euthanasia by the day of test termination, which is post-transplantation day 41. In Group 7, an excellent growth inhibitory effect was exhibited, but all animals were subjected to euthanasia due to re-growth of tumor after cessation of the drug. In Group 6 or Group 8, not only an excellent growth inhibitory effect was exhibited, but also a tumor growth inhibitory effect was confirmed even after cessation of the drug, and 1 out of 8 cases was in complete remission.

In the verification of the combinational effect, it was not possible to show an enhancement of the effect of combined use of PD-1 in Group 4 as compared to Group 3. On the other hand, in Group 6 or Group 8, it was possible to show a significant enhancement of the effect of combined use of PD-1 on post-transplantation day 23.

From the above results, it was found that the liposome composition according to the embodiment of the present invention, in a case of being used in combination with PD-1, had an excellent growth inhibitory effect on EMT6 tumor cells that are resistant to the effects of Gem or PD-1, and exhibited a remarkable and unexpected growth inhibitory effect that is superior to that of the combination of Gem and PD-1.

Example 3

Drug efficacy test with combined use of anti-CTLA-4 antibody in tumor-bearing model mouse with subcutaneous transplantation of EMT6

The anti-CTLA-4 antibody (hereinafter, also referred to as CTLA-4), Gem, and the liposome composition according to the embodiment of the present invention were used as test substances. Gemcitabine hydrochloride (manufactured by Teva Pharmaceutical Industries Ltd.) dissolved in physiological saline was used as Gem. The liposome composition according to the embodiment of the present invention was diluted with 5% Glu prior to use.

$1.7 \times 10^6$ EMT6 cells, which are a mouse breast cancer cell line, were subcutaneously transplanted into the flank of female Balb/c mice to form subcutaneous tumors. Using the tumor volume as an index, inhibitory effects of combined administration of CTLA-4 and Gem and combined administration of CTLA-4 and the liposome composition according to the embodiment of the present invention on subcutaneous tumors were evaluated.

CTLA-4 and a solvent therefor (PBS) were intraperitoneally administered twice a week for a total of 3 weeks, and Gem, the liposome composition according to the embodiment of the present invention, and a solvent therefor (5% Glu) were administered once a week by tail vein administration for a total of 3 weeks.

After the 3-week administration was completed, the drug was discontinued, and the tumor volume measurement was continued for 4 weeks. Test subjects with a tumor volume of more than 10% of body weight were euthanized during the test, and drug efficacy analysis was carried out based on the survival rate (tumor-free survival %).

Group configuration was set to a combination of 5% Glu and PBS for Group 1, a combination of 5% Glu and CTLA-4 (10 mg/kg) for Group 2, a combination of Gem (240 mg/kg) and PBS for Group 3, a combination of Gem (240 mg/kg) and CTLA-4 (10 mg/kg) for Group 4, a combination of the liposome composition according to the embodiment of the present invention (1 mg/kg) and PBS for Group 5, a combination of the liposome composition according to the embodiment of the present invention (1 mg/kg) and CTLA-4 (10 mg/kg) for Group 6, a combination of the liposome composition according to the embodiment of the present invention (4 mg/kg) and PBS for Group 7, and a combination of the liposome composition according to the embodiment of the present invention (4 mg/kg) and CTLA-4 (10 mg/kg) for Group 8.

Groups 1 to 5 and 7 are Comparative Examples, and Groups 6 and 8 are Examples. The group configuration and dose are shown in Table 8. In Table 1, "Dose" represents an amount as an active form of gemcitabine, "Twice/3W" represents twice-weekly administration for a total of 3 weeks, "Once/3W" represents once-weekly administration for a total of 3 weeks, "Abdomen" represents intraperitoneal administration, "Tail" represents tail vein administration, and "Lipo" represents the liposome composition according to the embodiment of the present invention. In addition, Lipo (1) and Lipo (4) mean that the liposome composition according to the embodiment of the present invention was administered to a subject at a dose of 1 mg/kg and a dose of 4 mg/kg, respectively.

TABLE 8

| Group | Test substance | Dose (mg/kg/ administration) CTLA-4 | Gem and Lipo | CTLA-4 and PBS Administration route | Administration schedule | Gem, Liposome composition, and 5% Glu Administration route | Administration schedule | Dosage (mL/kg) |
|---|---|---|---|---|---|---|---|---|
| 1 | 5% Glu + PBS | 0 | 0 | Abdomen | Twice/3W | Tail | Once/3W | 10 |
| 2 | 5% Glu + CTLA-4 | 10 | 0 | Abdomen | Twice/3W | Tail | Once/3W | 10 |
| 3 | Gem + PBS | 0 | 240 | Abdomen | Twice/3W | Tail | Once/3W | 10 |
| 4 | Gem + CTLA-4 | 10 | 240 | Abdomen | Twice/3W | Tail | Once/3W | 10 |
| 5 | Lipo (1) + PBS | 0 | 1 | Abdomen | Twice/3W | Tail | Once/3W | 10 |
| 6 | Lipo (1) + CTLA-4 | 10 | 1 | Abdomen | Twice/3W | Tail | Once/3W | 10 |
| 7 | Lipo (4) + PBS | 0 | 4 | Abdomen | Twice/3W | Tail | Once/3W | 10 |
| 8 | Lipo (4) + CTLA-4 | 10 | 4 | Abdomen | Twice/3W | Tail | Once/3W | 10 |

Changes in tumor volume for each individual in each group are shown in FIGS. 21 to 28. Table 9 shows the number of test subjects in complete remission (test subjects with zero tumor volume) by post-transplantation day 52, the number of test subjects in the group, and the complete remission rate (%).

TABLE 9

| Group | Number of test subjects in complete remission | Number of individuals in group | Complete remission rate (%) |
|---|---|---|---|
| 1 | 0 | 8 | 0 |
| 2 | 1 | 8 | 12.5 |
| 3 | 0 | 8 | 0 |

TABLE 9-continued

| Group | Number of test subjects in complete remission | Number of individuals in group | Complete remission rate (%) |
|---|---|---|---|
| 4 | 1 | 8 | 12.5 |
| 5 | 0 | 8 | 0 |
| 6 | 1 | 8 | 12.5 |
| 7 | 0 | 8 | 0 |
| 8 | 7 | 8 | 87.5 |

In Group 1, Group 2, Group 3, Group 4, Group 5, and Group 6, tumor growth could not be stopped during the dosing period. All test subjects in Group 1, Group 3, and Group 5, and 7 out of 8 test subjects in Group 2, Group 4, and Group 6 were subjected to euthanasia by the day of test termination, which is post-transplantation day 52. In Group 7, an excellent growth inhibitory effect was exhibited, but tumors increased after the dosing period and therefore all test subjects were subjected to euthanasia. In Group 8, an excellent growth inhibitory effect was exhibited, a tumor growth inhibitory effect was confirmed even after the dosing period, and 7 out of 8 cases were in complete remission.

Figure 29:
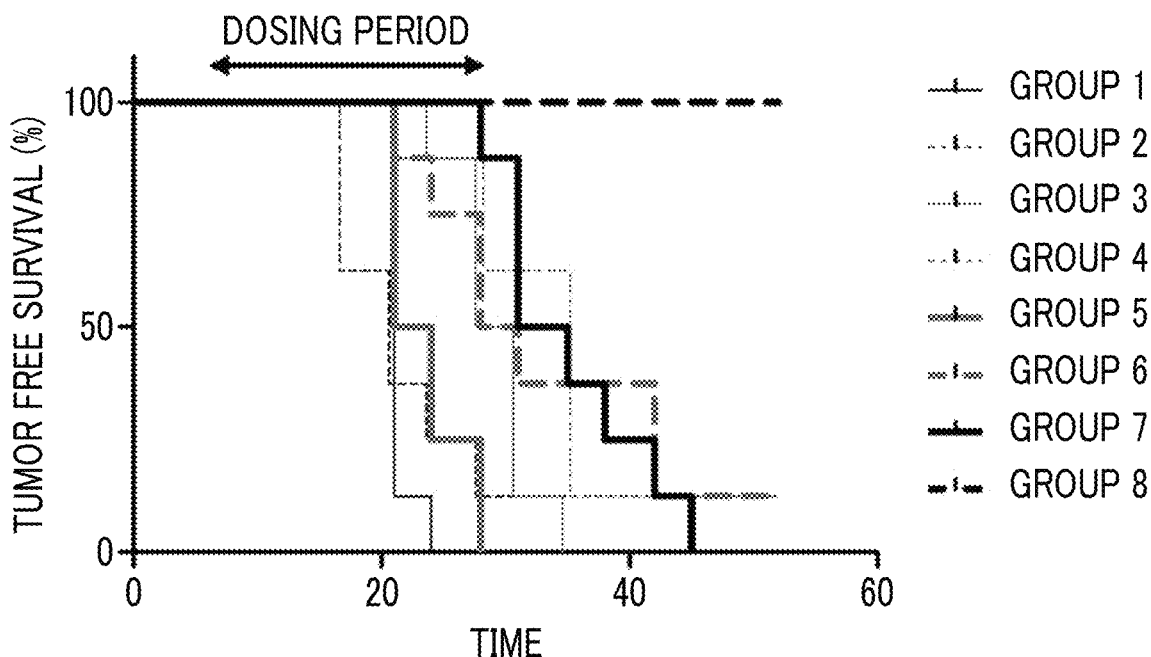
FIG. 29 shows a survival rate (tumor-free survival %) in a case where a test subject having a tumor volume of more than 10% of the body weight is euthanized, and the results of a survival curve by the Kaplan-Meier method.

The survival rate (tumor-free survival %) in a case where a test subject with a tumor volume of more than 10% of body weight was euthanized was calculated, and the results of a survival curve by the Kaplan-Meier method are shown in FIG. 29. In FIG. 29, Group 1 to Group 8 mean Group 1 to Group 8. As a statistical analysis of an effect of prolonging the survival time, a log-rank test was carried out, and a p value of less than 5% between the groups was determined to have a statistically significant difference. Graghpad Prism version 5.03 was used for the calculation of median survival calculated from the survival curve by Kaplan-Meier method and the statistical analysis. Table 10 shows the results of analysis of the survival curve by the Kaplan-Meier method.

In the log-rank test of Table 10, "a" indicates $p<0.05$, "b" indicates $p<0.001$, "c" indicates $p<0.0001$, and "ns" indicates no significant difference. "Undefined" indicates that the survival rate did not fall below 50% in the median survival analysis and could not be analyzed.

TABLE 10

| Control group | | 2 | 3 | 5 | 7 | 4 | 6 | 8 |
|---|---|---|---|---|---|---|---|---|
| Comparative group | | | 1 | | | 3 | 5 | 7 |
| Log-rank Test | p value | 0.7161 | 0.001 | 0.0773 | <0.0001 | 0.1089 | 0.0134 | <0.0001 |
| | Determination | ns | b | ns | c | ns | a | c |
| Median survival | Control group | 21 | 29.5 | 22.5 | 33 | 35 | 29.5 | Undefined |
| | Comparative group | 21 | 21 | 21 | 21 | 29.5 | 22.5 | 33 |
| | Percentage | 1.00 | 1.40 | 1.07 | 1.57 | 1.19 | 1.31 | — |

No significant prolongation of the survival time was observed in Group 2 or Group 5 as compared to Group 1, and a statistically significant effect of prolonging the survival time was observed in Group 3 or Group 7 as compared to Group 1. In the verification of the combinational effect, no significant change in effect of prolonging the survival time was confirmed in Group 4 as compared to Group 3, and the effect of prolonging the survival time was significantly enhanced in Group 6 as compared to Group 5. Furthermore, Group 8 exhibited a significant enhancement of the effect of prolonging the survival time as compared to Group 7, and 7 out of 8 cases survived until the day of test termination, which is post-transplantation day 52.

From the above results, it was shown that the liposome composition according to the embodiment of the present invention, in a case of being used in combination with CTLA-4, had an excellent growth inhibitory effect on EMT6 tumor cells that are resistant to the effects of Gem or CTLA-4, and the growth inhibitory effect was superior to that of the combination of Gem and CTLA-4.

Example 4

Changes in immune cell composition in tumor in tumor-bearing model mouse with subcutaneous transplantation of EMT6

Various immune cells infiltrate the tumor and affect tumor growth. The immune cells coexist in a mixture of cytotoxic CD8-positive T cells that play a central role in antitumor activity, antitumor immune cells centering on NK cells and M1 macrophages, and tumor-promoting immune cells centering on regulatory T cells (Tregs) and M2 macrophages that suppress these immune cells.

There are two types of subsets (M1 and M2) in macrophages. M1 macrophages exhibit an antibacterial or antiviral activity and an antitumor activity. M2 macrophages exhibit actions of tissue repair, neoangiogenesis, tumor growth promotion, and immunosuppression. It is considered that macrophages infiltrating tumor tissues in association with the progression of tumor (tumor-associated macrophages: TAM) shift from M1 macrophages to M2 macrophages. From this, the predominance of M1 macrophages is considered to be important for the antitumor action, and changing the balance of M1 macrophages and M2 macrophages may be a new therapeutic approach.

Cytotoxic CD8-positive T cells, which play a major role in tumor immunity, are cells that have differentiated and proliferated by sensitizing unsensitized CD8-positive T cells by antigenic stimulation or the like, and play a role of removing virus-infected cells, cancer cells, and the like. Cancer cells considered non-self by CD8-positive T cells are induced to cell death. On the other hand, it is known that cancer cells attract immunosuppressive cells such as Tregs and M2 macrophages therearound to thereby suppress the attack from CD8-positive T cells, and escape from the immune surveillance (reference: Immunology. 2013; 138 (2): 105-115).

It is said that a high percentage of CD8-positive T cells in the tumor and a high ratio of M1 macrophages compared to M2 macrophages result in an antitumor environment (reference: J Clin Invest. 2012; 122(3); 787-95). Therefore, whether the state of intratumoral immune cells in the combined administration of the anti-CTLA-4 antibody and Gem, and the combined administration of the anti-CTLA-4 antibody and the liposome composition according to the embodiment of the present invention was in an antitumor environment or a tumor growth environment was evaluated based on the percentage of CD8-positive T cells and the percentage of M1 macrophages showing an antitumor activity and M2 macrophages showing a tumor growth promoting activity as indices.

$3.0 \times 10^6$ EMT6 cells, which are a mouse breast cancer cell line, were subcutaneously transplanted into the flank of female Balb/c mice to form subcutaneous tumors.

The anti-CTLA-4 antibody (hereinafter, also referred to as CTLA-4), Gem, and the liposome composition according to the embodiment of the present invention were used as test substances. Gemcitabine hydrochloride (manufactured by Teva Pharmaceutical Industries Ltd.) dissolved in physiological saline was used as Gem. The liposome composition according to the embodiment of the present invention was diluted with 5% Glu prior to use. Individuals were used to whom CTLA-4 and a solvent therefor (PBS) were intraperitoneally administered twice a week for a total of 5 times, and Gem, the liposome composition according to the embodiment of the present invention, and a solvent therefor (5% Glu) were administered once a week by tail vein administration for a total of 3 times. Tumors were excised on Days 16 and 17 after the start of administration and used for analysis of intratumoral immune cells.

The excised tumor was made into a cell-dispersed state using Tumor Dissociation Kit, mouse (catalog number 130-096-730, manufactured by Miltenyi Biotec GmbH), and intratumoral immune cells were isolated using CD45 (TIL) MicroBeads (catalog number 130-110-618, manufactured by Miltenyi Biotec GmbH). Dead cells were stained using LIVE/DEAD (trademark) Fixable Yellow Dead Cell Stain Kit (catalog number L34968, manufactured by Invitrogen Corporation), and various immune cell markers were stained using the following fluorescently labeled antibodies. CD3 used was CD3 Antibody, Alexa Fluor (registered trademark) 700 (catalog number 56-0032-82, manufactured by eBioscience, Inc.), CD8 used was CD8a-PE-Vio 770, mouse (catalog number 130-102-358, manufactured by Miltenyi Biotec GmbH), CD11b used was CD11b Monoclonal Antibody (M1/70), eFluor 450 (catalog number 48-0112-82, manufactured by eBioscience, Inc.), F4/80 used was F4/80-APC, mouse (catalog number 130-102-379, manufactured by Miltenyi Biotec GmbH), MHC Class II used was MHC Class II-APC-Vio 770, mouse (catalog number 130-112-233, manufactured by Miltenyi Biotec GmbH), and CD206 used was PE/Cy7 anti-mouse CD206 (MMR) Antibody (catalog number 141720, manufactured by BioLegend, Inc.). The samples were analyzed using a flow cytometer (Attune NxT, manufactured by Invitrogen Corporation). CD8-positive T cells (CD3-positive, CD8-positive), M1 macrophages (CD11b-positive, F4/80-positive, MHC Class II-positive, CD206-negative), and M2 macrophages (CD11b-positive, F4/80-positive, MHC Class II-negative, CD206-positive) were identified, and the percentage of each cell group was calculated.

Group configuration was set to a combination of 5% Glu and PBS for Group 1, a combination of Gem (240 mg/kg) and PBS for Group 2, a combination of the liposome composition according to the embodiment of the present invention (4 mg/kg) and PBS for Group 3, a combination of Gem (240 mg/kg) and CTLA-4 (10 mg/kg) for Group 4, and a combination of the liposome composition according to the embodiment of the present invention (4 mg/kg) and CTLA-4 (10 mg/kg) for Group 5.

Groups 1, 2, and 4 are Comparative Examples, and Groups 3 and 5 are Examples. Group configuration and dose are shown in Table 11.

In Table 11, "Dose" represents an amount as an active form of gemcitabine, "5 times" represents twice-weekly administration for a total of 5 times, "3 times" represents once-weekly administration for a total of 3 times, "Abdomen" represents intraperitoneal administration, "Tail" represents tail vein administration, and "Lipo" represents the liposome composition according to the embodiment of the present invention. In addition, Lipo (4) means that the liposome composition according to the embodiment of the present invention was administered to a subject at a dose of 4 mg/kg.

TABLE 11

| Group | Test substance | Dose (mg/kg/administration) | | CTLA-4 and PBS | | Gem, Liposome composition, and 5% Glu | | Dosage (mL/kg) |
|---|---|---|---|---|---|---|---|---|
| | | CTLA-4 | Gem and Lipo | Administration route | Administration schedule | Administration route | Administration schedule | |
| 1 | 5% Glu + PBS | 0 | 0 | Abdomen | 5 times | Tail | 3 times | 10 |
| 2 | Gem + PBS | 0 | 240 | Abdomen | 5 times | Tail | 3 times | 10 |
| 3 | Lipo (4) + PBS | 0 | 4 | Abdomen | 5 times | Tail | 3 times | 10 |
| 4 | Gem + CTLA-4 | 10 | 240 | Abdomen | 5 times | Tail | 3 times | 10 |
| 5 | Lipo (4) + CTLA-4 | 10 | 4 | Abdomen | 5 times | Tail | 3 times | 10 |

Figure 30:
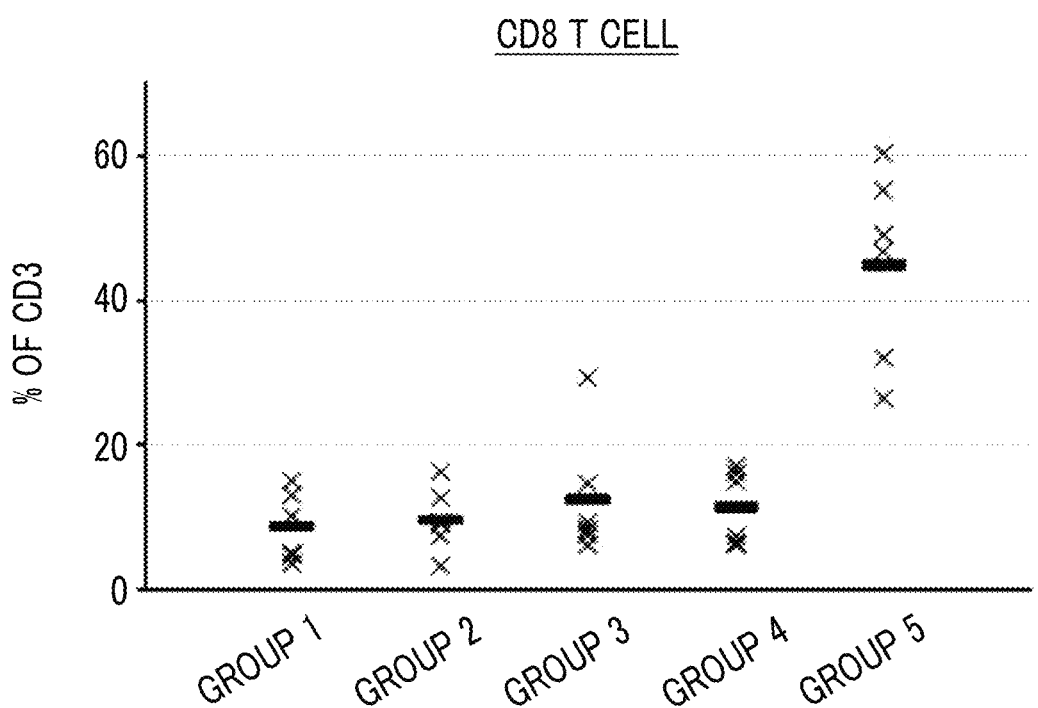
FIG. 30 shows a mean value of a percentage of CD8-positive T cells in each group in a drug efficacy test using a tumor-bearing model mouse with subcutaneous transplantation of EMT6.
Figure 31:
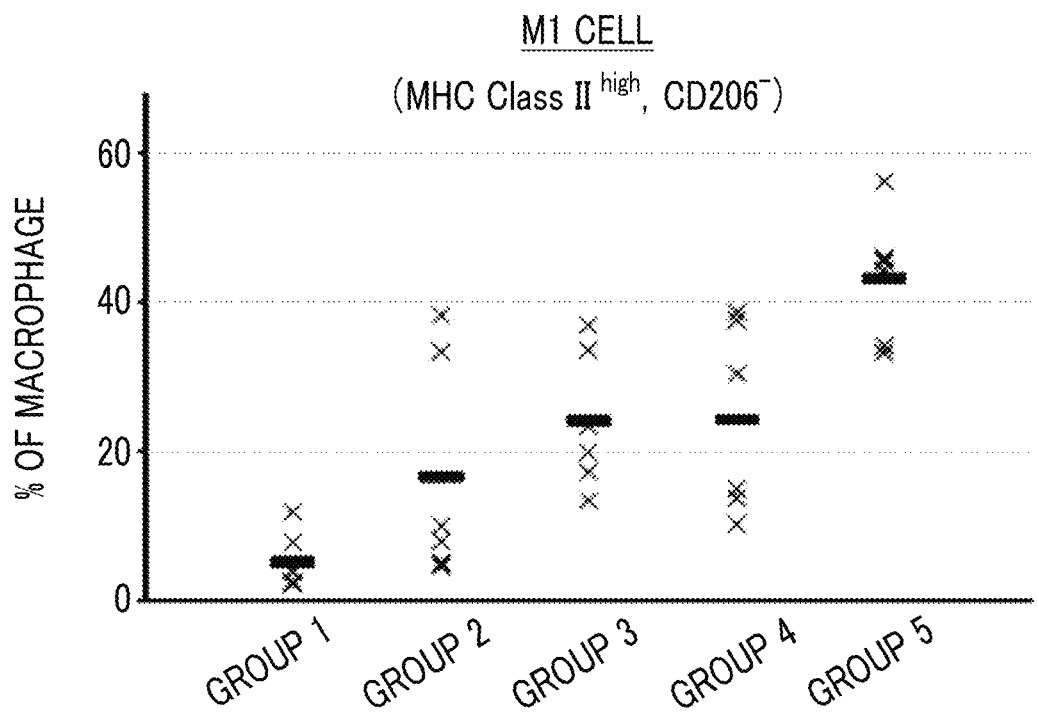
FIG. 31 shows a mean value of a percentage of M1 cells in each group in a drug efficacy test using a tumor-bearing model mouse with subcutaneous transplantation of EMT6.
Figure 32:
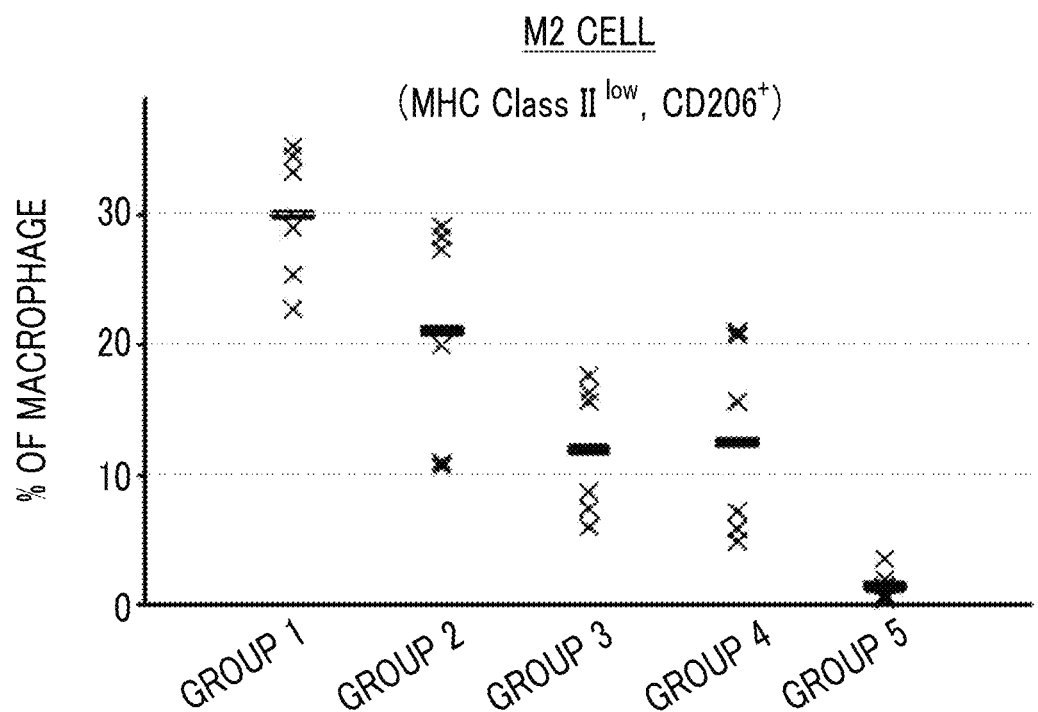
FIG. 32 shows a mean value of a percentage of M2 cells in each group in a drug efficacy test using a tumor-bearing model mouse with subcutaneous transplantation of EMT6.

The percentage of each individual in each group and the mean value of each group are shown in FIG. 30 (CD8-positive T cells), FIG. 31 (M1 macrophages), and FIG. 32 (M2 macrophages).

The percentage of CD8-positive T cells in the tumor was not changed in Group 1, Group 2, Group 3, and Group 4, but the infiltration of CD8-positive T cells was significantly increased in Group 5. In addition, in a case where the percentage of M1 macrophages and the percentage of M2 macrophages were compared, M1 macrophages were significantly increased and M2 macrophages were decreased in Group 5.

From the above results, it was suggested that the liposome composition according to the embodiment of the present invention, in a case of being used in combination with CTLA-4, shifts the balance of M1 macrophages and M2 macrophages in a tumor to an inflammatory state and induces the infiltration of CD8-positive T cells, thus leading to an antitumor effect.

Example 5

Verification of effect of combinational effect of anti-CTLA-4 antibody on CD8-positive T cells in tumor-bearing model mouse with subcutaneous transplantation of EMT6

The anti-CTLA-4 antibody (hereinafter, also referred to as CTLA-4), the anti-CD8 antibody, and the liposome composition according to the embodiment of the present invention were used as test substances. The liposome composition according to the embodiment of the present invention was diluted with 5% Glu prior to use.

$0.5 \times 10^6$ EMT6 cells, which are a mouse breast cancer cell line, were subcutaneously transplanted into the flank of female Balb/c mice to form subcutaneous tumors. Using the tumor volume as an index, CD8-positive T cells were removed by anti-CD8 antibodies to evaluate the effect of the combined administration of CTLA-4 and the liposome composition according to the embodiment of the present invention on an antitumor effect.

The anti-CD8 antibody, CTLA-4, and a solvent therefor (PBS) were intraperitoneally administered twice a week for a total of 6 times, and the liposome composition according to the embodiment of the present invention and a solvent therefor (5% Glu) were administered once a week by tail vein administration for a total of 3 times.

Group configuration was set to a combination of CTLA-4 and the liposome composition according to the embodiment of the present invention for Group 1, and a combination of anti-CD8 antibody, CTLA-4, and the liposome composition according to the embodiment of the present invention for Group 2.

Figure 33:
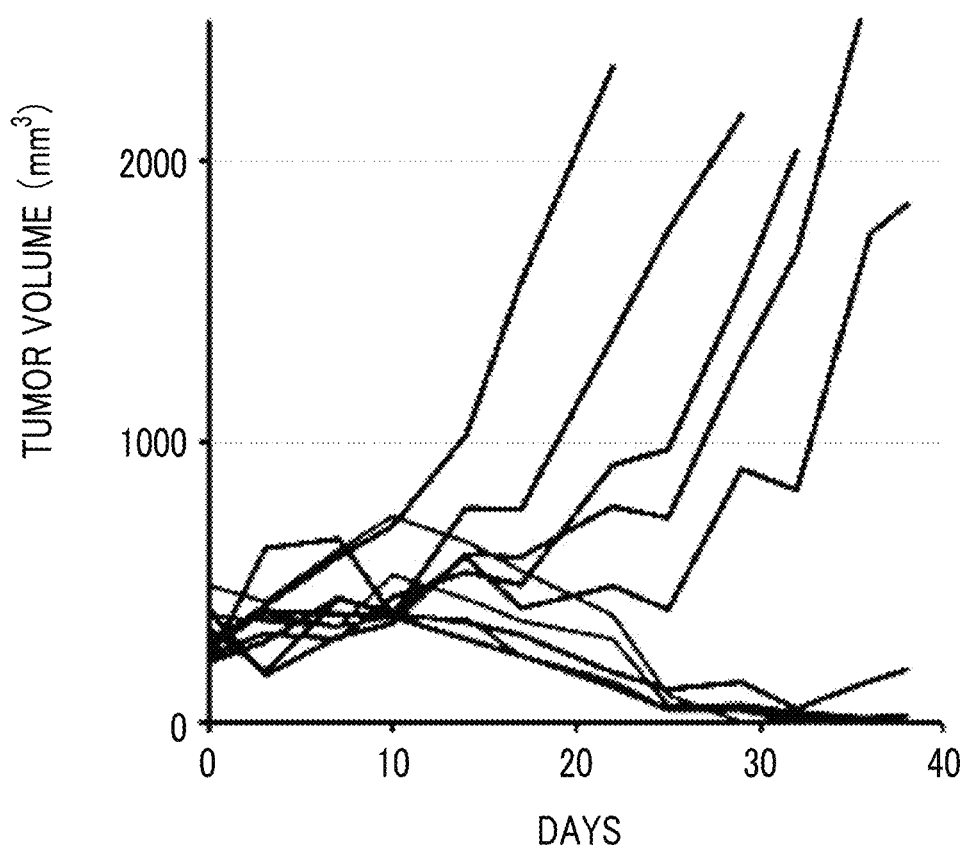
FIG. 33 shows changes in tumor volume by individual in a control group in a test for verifying an effect on CD8-positive T cells using a tumor-bearing model mouse with subcutaneous transplantation of EMT6.
Figure 34:
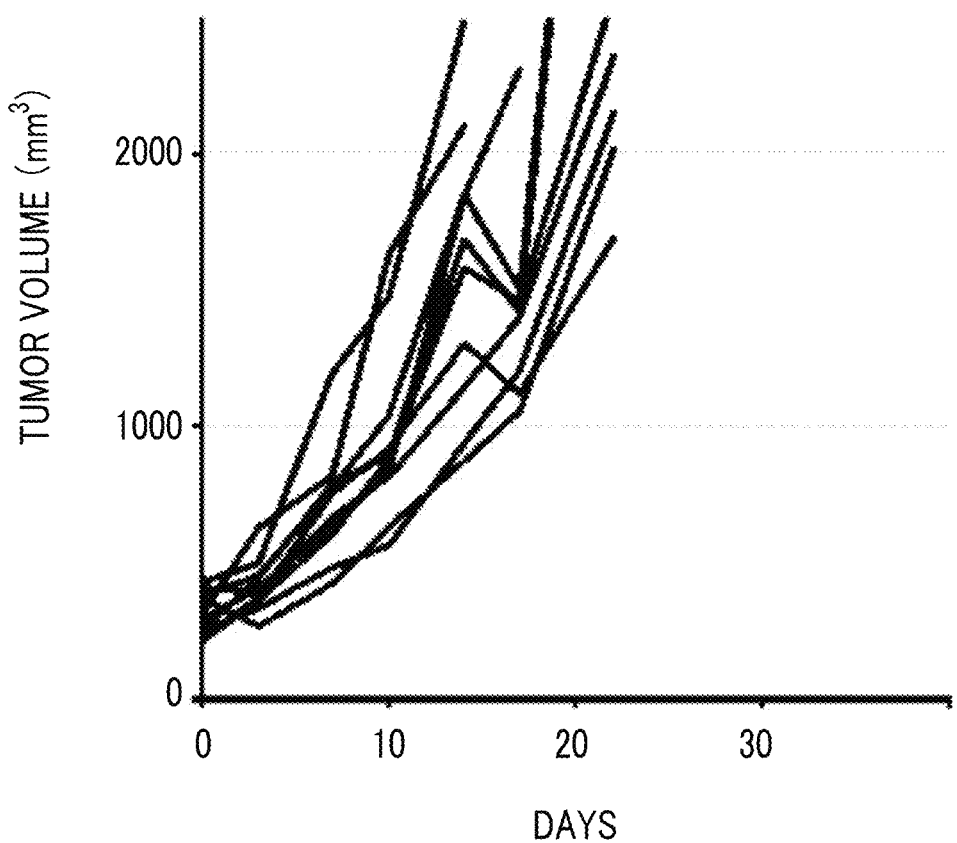
FIG. 34 shows changes in tumor volume by individual in an anti-CD8 antibody-administered group in a test for verifying an effect on CD8-positive T cells using a tumor-bearing model mouse with subcutaneous transplantation of EMT6.

The tumor volume of each individual in each group is shown in FIG. 33 (Group 1) and FIG. 34 (Group 2).

The antitumor effect observed in Group 1 was completely abolished in Group 2 by removing CD8-positive T cells.

From the above results, it was suggested that, in the combinational effect of the liposome composition according to the embodiment of the present invention and CTLA-4, the infiltration of CD8-positive T cells in the tumor acts as the essential aspect of the antitumor effect.

Reference Example

Changes in immune cell composition in circulating blood and tumor in human

It has been reported that Tregs and immunosuppressive myeloid-derived suppressor cells (MDSCs) are increased in the peripheral blood of cancer patients, which is thus associated with malignancy of cancer. Regulatory T cells (Tregs) play an important role in "immune tolerance" that avoids an immune response to self but also participate in "immune evasion" of cancer cells and therefore suppress an antitumor immune response (reference: J Transl Med. 2016; 14; 282). MDSCs are progenitor cells of granulocytes, dendritic cells, macrophages, or the like, and are highly diverse cell populations that are induced in response to oncogenic factors such as cytokines and have different degrees of differentiation. It is known that the most important function of MDSCs is suppression of immune response, and its suppression mechanism is also extremely diverse. Based on these findings, MDSCs, along with regulatory T cells, are cells that play an important role in an immunosuppressive condition of cancer patients, and have recently attracted attention as cells that interfere with cancer immunotherapy (reference: Journal of Japan Society of Immunology & Allergology in Otolaryngology (JJIAO) 2013; 30(4): 271-278).

Therefore, in a phase 1 trial of the liposome composition according to the embodiment of the present invention, changes in CD8-positive T cells and immunosuppressive Tregs and MDSCs in circulating blood, as well as MDSCs in tumors were evaluated for cancer patients administered with the liposome composition according to the embodiment of the present invention.

The liposome composition according to the embodiment of the present invention was used as a test substance. The dose and dosing schedule are shown in Table 12.

TABLE 12

| Cohort | Test substance | Number of patients | Dose (mg/m$^2$) | Administration schedule |
|---|---|---|---|---|
| 1 | Liposome composition | 3 | 1.2 mg/m$^2$ | Once for 2 weeks |
| 2 | Liposome composition | 4 | 2.4 mg/m$^2$ | Once for 2 weeks |

TABLE 12-continued

| Cohort | Test substance | Number of patients | Dose (mg/m²) | Administration schedule |
|---|---|---|---|---|
| 3 | Liposome composition | 3 | 4.8 mg/m² | Once for 2 weeks |

Analysis of immune cells in peripheral blood was carried out before the test substance administration (C1D1), 7 days after the first administration (C1D8), 14 days after the first administration (C1D15), and 14 days after the second administration (C2D1), and single-cell analysis was carried out before the test substance administration (pre-dose) and 15 days after the second administration (C2D2).

Figure 35:
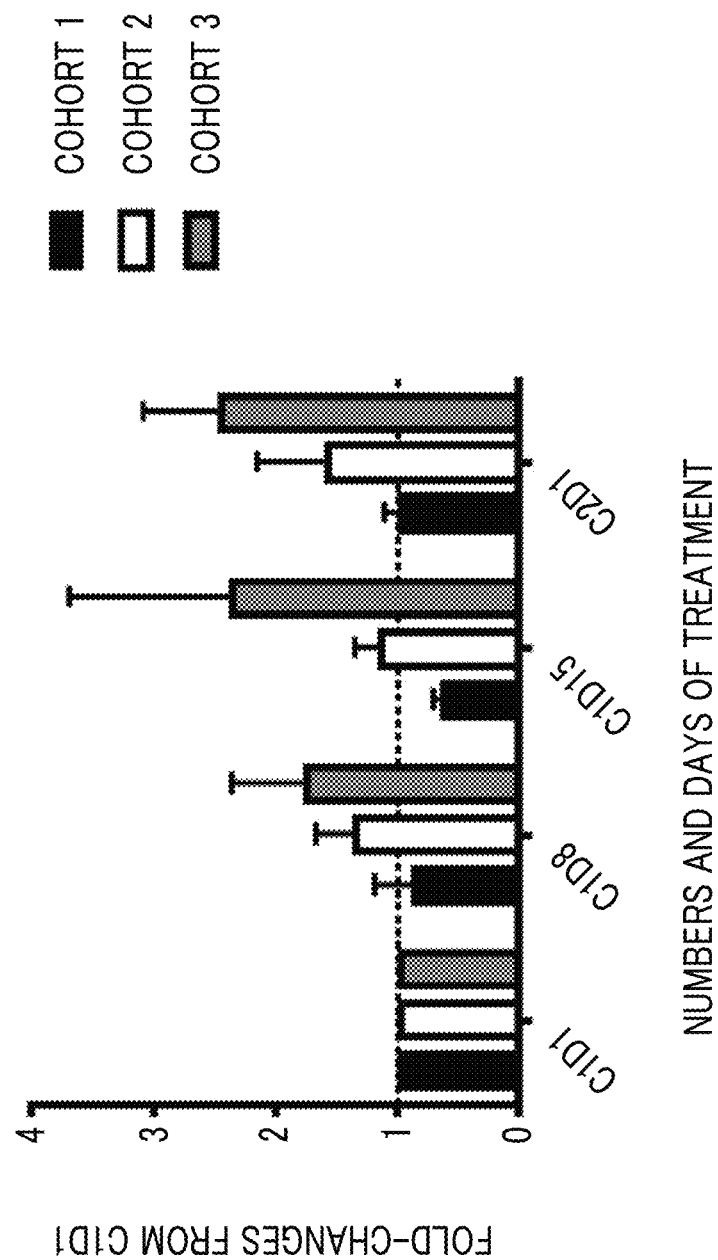
FIG. 35 shows changes in percentage of Ki67-positive cells in CD8-positive T cells from before administration of a test substance in circulating blood in a test for verifying changes in immune cell composition in circulating blood and tumors in humans.
Figure 36:
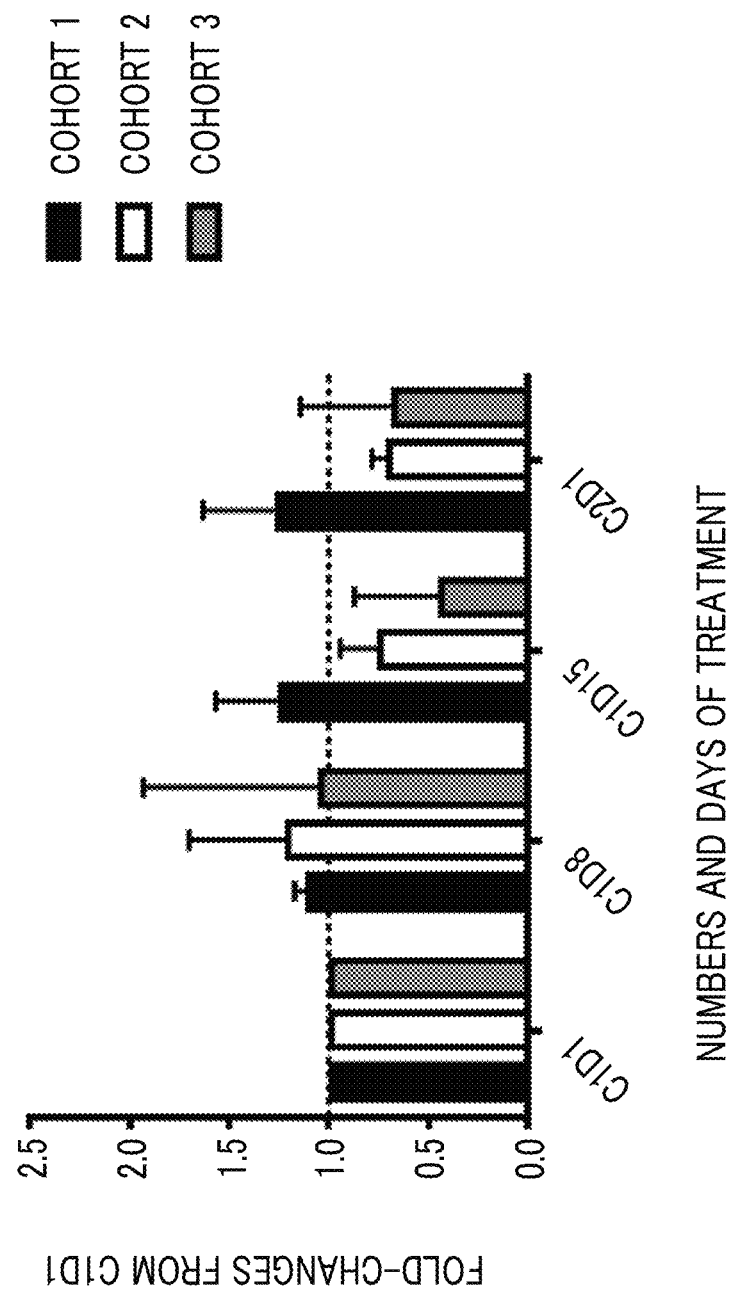
FIG. 36 shows changes in percentage of Ki67-positive Tregs in Tregs from before administration of a test substance in circulating blood in a test for verifying changes in immune cell composition in circulating blood and tumors in humans.
Figure 37:
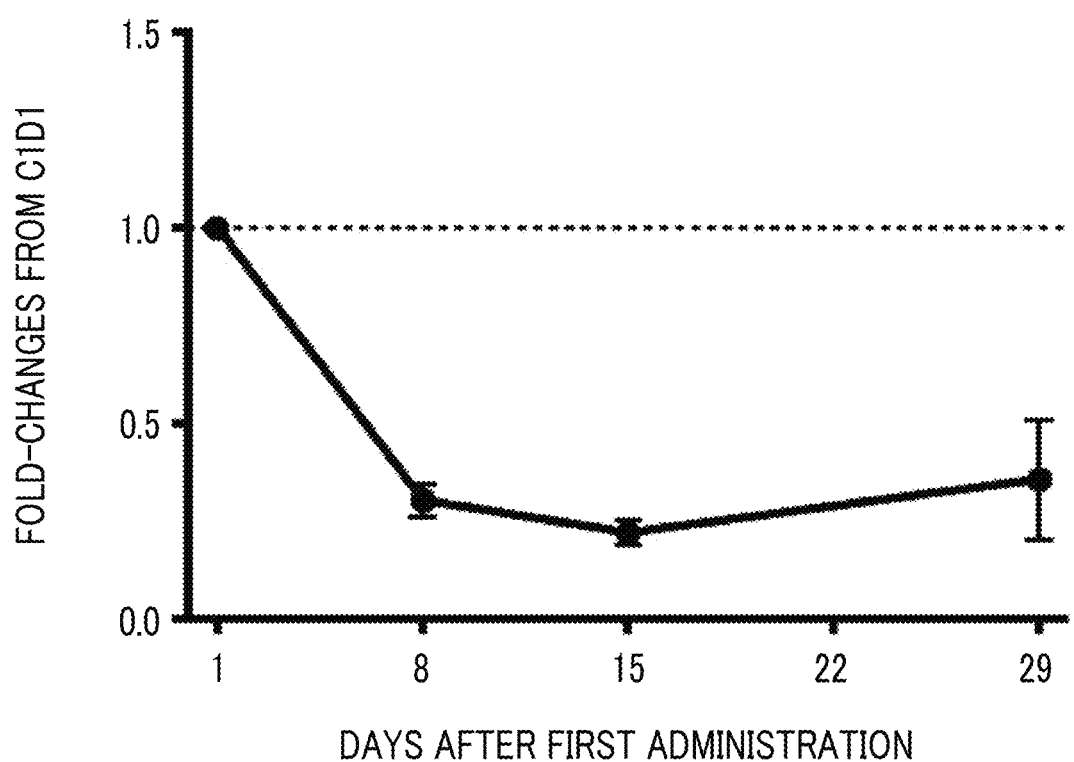
FIG. 37 shows changes in percentage of M-MDSCs in total MDSCs from before administration of a test substance in circulating blood in a test for verifying changes in immune cell composition in circulating blood and tumors in humans.
Figure 38:
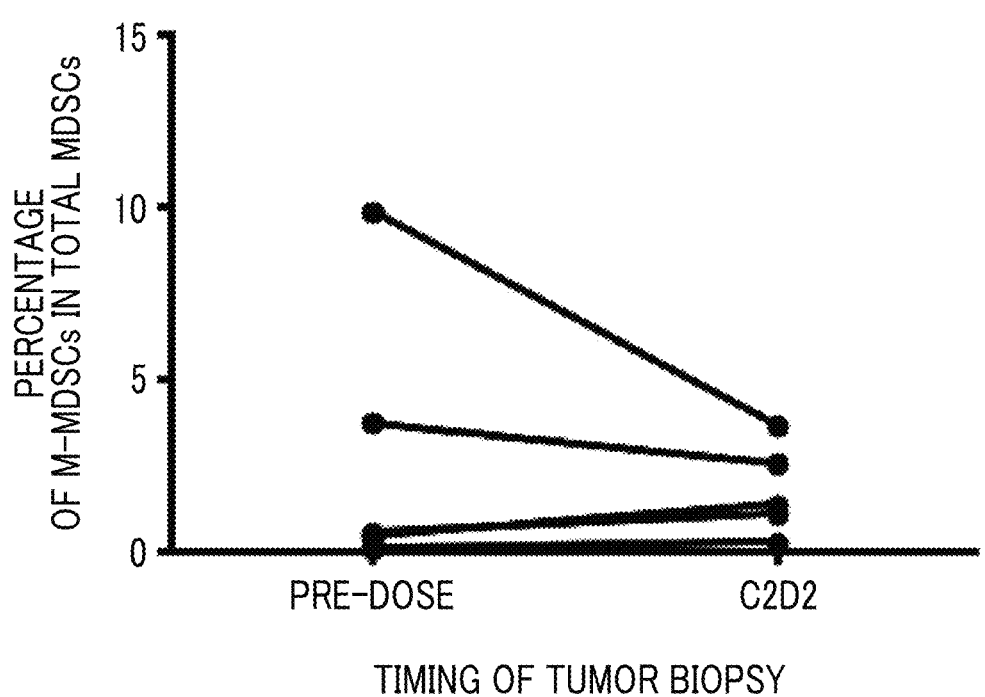
FIG. 38 shows a value obtained by comparing percentages of M-MDSCs in total MDSCs in tumors between before administration of a test substance and 15 days after a second administration of the test substance, in a test for verifying changes in immune cell composition in circulating blood and tumors in humans.

FIG. 35 shows changes from C1D1 in the percentage of Ki67-positive CD8-positive T cells, which is an index of growth, with respect to total CD8-positive T cells (CD3-positive, CD8-positive) in circulating blood of patients. FIG. 36 shows changes from C1D1 in Ki67-positive Tregs with respect to total Tregs (CD3-positive, CD25-positive, CD127-negative, foxp3-positive) in circulating blood. FIG. 37 shows changes from C1D1 in M-MDSCs (CD14-positive, CD15-negative MDSCs) with respect to total MDSCs (CD3-negative, CD19-negative, CD56-negative, HLA-DR-negative, CD11b-positive, CD33-positive) in circulating blood. FIG. 38 shows the values obtained by comparing M-MDSCs between before the test substance administration and C2D2, with respect to total MDSCs in tumors in 5 patients with tumor samples from Cohorts 1 to 3.

In FIG. 35, an increase in Ki67-positive CD8-positive T cells was observed in the group of Cohort 3.

In FIG. 36, a decrease in Ki67-positive Tregs was observed in the group of Cohort 3. In FIG. 37, a decrease in the percentage of M-MDSCs was observed in the group of Cohort 3.

In FIG. 38, a decrease in the percentage of M-MDSCs was observed in the group of Cohort 3.

From the above results, it was suggested that the liposome composition according to the embodiment of the present invention has an effect of decreasing immunosuppressive Ki67-positive Tregs and M-MDSCs and an effect of increasing Ki67-positive CD8-positive T cells having an antitumor effect. Due to these effects, the liposome composition according to the embodiment of the present invention alone and a combination thereof with an immune checkpoint inhibitor may be a novel therapeutic approach through an immune activating effect.

The pharmaceutical formulation according to the embodiment of the present invention is useful as a pharmaceutical formulation for preventing or treating cancer. The administration method according to the embodiment of the present invention is useful as a method for administering a pharmaceutical formulation for preventing or treating cancer. Furthermore, the treatment method according to the embodiment of the present invention is useful as a treatment method for preventing or treating cancer.

What is claimed is:

1. A method for treating a tumor disease that is refractory to treatment with an immune checkpoint inhibitor, the method consisting of:
   simultaneously or sequentially administering (A) a liposome composition and (B) an immune checkpoint inhibitor in combination to the subject at an effective dose and for an effective dosing period that exhibit a therapeutic synergistic effect,
   wherein the immune checkpoint inhibitor includes at least one selected from an anti-PD-1 antibody and an anti-PD-L1 antibody,
   the liposome composition includes liposomes each having an inner water phase, and an aqueous solution constituting an outer water phase and having the liposomes dispersed therein, and gemcitabine is encapsulated in a dissolved state in the liposomes, and
   the tumor disease that is refractory to treatment with an immune checkpoint inhibitor is one or more of breast cancer, non-small cell lung cancer, small cell lung cancer, colorectal cancer, renal cell carcinoma, prostate cancer, hepatocellular carcinoma, gastric cancer, pancreatic cancer, soft tissue sarcoma, Kaposi's sarcoma, carcinoid carcinoma, head and neck cancer, melanoma, ovarian cancer, bile duct cancer and mesothelioma.

2. The treatment method according to claim 1, in which the liposome composition is a liposome composition in which an osmotic pressure of the inner water phase of the liposome is 2 times or more and 8 times or less an osmotic pressure of the outer water phase, and a release rate of gemcitabine from the liposome is 10% by mass/24 hr or more and 70% by mass/24 hr or less at 37° C. in human plasma.

3. The treatment method according to claim 1, in which the liposome composition is a liposome composition in which a content of cholesterols is 10 mol % or more and 35 mol % or less with respect to a total amount of lipid components of the liposome composition, and an osmotic pressure of the inner water phase is 2 times or more and 8 times or less an osmotic pressure of the outer water phase.

4. The treatment method according to claim 1, in which the immune checkpoint inhibitor is an anti-PD-1 antibody.

5. The treatment method according to claim 1, in which the state of intratumoral immune cells shifts from a tumor growth environment to an antitumor environment.

6. The treatment method according to claim 1, in which M1 macrophages are increased and M2 macrophages are decreased.

* * * * *